US005981277A

United States Patent [19]

Fransen et al.

[11] Patent Number: 5,981,277

[45] Date of Patent: Nov. 9, 1999

[54] POLYPEPTIDES AND PEPTIDES, NUCLEIC ACIDS CODING FOR THEM, AND THEIR USE IN THE FIELD OF TUMOR THERAPY, INFLAMMATION OR IMMUNOLOGY

[75] Inventors: Lucia Fransen, Nazareth-Eke; Kathleen Devos, Destelbergen; André Van De Voorde, Lokeren; Hugo Van Heuverswyn, Kalken, all of Belgium

[73] Assignee: N.V. Innogenetics S.A., Belgium

[21] Appl. No.: 08/318,837

[22] PCT Filed: Apr. 28, 1993

[86] PCT No.: PCT/EP93/01022

§ 371 Date: Oct. 13, 1994

§ 102(e) Date: Oct. 13, 1994

[87] PCT Pub. No.: WO93/22437

PCT Pub. Date: Nov. 11, 1993

[30] Foreign Application Priority Data

Jun. 30, 1992 [EP] European Pat. Off. .............. 92401231

[51] Int. Cl.[6] .............................. C12N 5/02; C12N 5/06; C07N 21/04

[52] U.S. Cl. ...................... 435/325; 435/320.1; 435/455; 435/364; 435/367; 435/252.3; 435/252.33; 435/254.11; 536/23.1; 536/23.5; 536/24.33; 536/24.1; 935/9; 935/10; 935/11; 935/32; 935/66

[58] Field of Search ............................. 435/320.1, 172.3, 435/240.2, 252.3, 252.33, 254.11, 325, 455, 364, 365, 367; 536/23.1, 23.5, 24.33, 24.1; 935/9, 10, 11, 32, 66

[56] References Cited

U.S. PATENT DOCUMENTS 5,049,659 9/1991 Cantor et al. .......................... 530/351

FOREIGN PATENT DOCUMENTS 0310056 4/1989 European Pat. Off. .

OTHER PUBLICATIONS

Webster's II New Riverside University Dictionary, 1984, Soukhanov et al., eds., Houghton Mifflin Company, Boston, MA, p. 67.

Reeck et al. 1987 Cell 50: 667.

Watson et al. 1987 in: Molecular Biology Of The Gene, Fourth Edition, Benjamin/Cummings Publ. Co., Inc., Menlo Park Ca, p. 313.

Bosman et al. 1989 Downstream Processing in Biotechnol. II (2.29–2.36). (Abstract).

*Primary Examiner*—Christopher S. F. Low
*Attorney, Agent, or Firm*—Bierman, Muserlian and Lucas

[57] ABSTRACT

An isolated and purified nucleic acid comprising:

a nucleotide sequence which has at least 50% sequence identity, with any of the nucleotide sequences coding for polypeptides containing in their pepridic chains:
the amino acid sequence of 311 amino acids of FIGS. 2 or 3,
or a fragment of this sequence being such that it is able to produce antibodies capable of forming a complex with the amino acid sequence of FIG. 2 or 3,
or an amino acid sequence having a percentage of homology of at least 50%, with the amino acid sequence of FIG. 2 or 3,
or a sequence able to form a complex with antibodies raised against the amino acid sequence of FIG. 2 or 3,
or against pep1(m) or pep1(h)
or against pep2(m) or pep2(h)
or against pep3(m) or pep3(h)

a nucleotide sequence which hybridizes with nucleotide sequence coding for said polypeptides,
or the above-indicated nucleotide sequences wherein T is replaced by U,
or the complementary sequences of the above-mentioned nucleotide sequences and vectors containing necessary elements to promote the expression in a cellular host of polypeptides coated by nucleic acids thereof.

5 Claims, 31 Drawing Sheets

```
GGTACCTGCA GTGATGGGGG TGGGGGGAGG TGCACTCCTA GAGCAGAGGG GGGTGGGTGG 60
GGCAGTCTCC AAGCTCCGAA ATGCACCTCC ACCAGATCTT GAGCCTCAGG GTGATGTCAC 120
TTGATGTGCT GGGCAAGGTC CTGGCTCCAG GCTTTCGATG GGGTGGGTGC TCTGAACACA 180
TCCTTACAAT GAAACTACCT TCAGTGGTCA CTGTCATCGC CTTCCAGTTC TTCAGACCCT 240
CACCCTTGTC CCAGCTTTCC TGGGCTGGGG GCTGGGCTCC ACCTGCCTTT GCCGGTGACT 300
TCCGTCCCTG CAGACTCACA ATTTTCAAAG CCCTCTCCCC GCCTCCTCTG GTAGTCACAA 360
CCCAGTTATT CAGACTTGCA CAGGTCGTTC GCAAGTCCTC CTGGAAGGTA TCTTGGCTGG 420
AAAAGGGGAC AAGGCCAAGC TTCCCCACCG CTGGATGCTG CGCTCGGCTC TGGAACTGAC 480
ACCAGGCGTC TCGGGCAGGG CCACTGACCC GCAGCACACA GAAGCCAGCT TTGCCATCGC 540
AGCGGGGACCGC(C)GGGCGGGCCASSTCCGC CCTCTCCTGC CTGGGGGGCC CTCGGCACCC 600
TCTGGCTCCC CTTCTCTGGC CTGAGTCTCT AGGGCCTCCC CAGTCCGGGC GGGGGTCTCC 660
GCTGTCCCCC CAACTGGGTC AGGCACGTGG TGGCCGCGGT GACCACCTGG GGAAGGCGCC 720
GACTCCGAGG AACACACTCG AGCAGGACGC TCCGCAGGTG ATTCTGCCCC GCGGGCACGG 780
GGTGGGGGCG GGATTTGGCC AAATCTGCAG AGAGTTTAGG TTGTCAAAGC TGGGGCGGGG 840
GTTGCTACTG ATACCCAGAG TGCGGGGGCC AGGGTGCTGC CAACATCCCA CCATGCGCAG 900
GACGTCCCCA CCCCAAGAAC CACCCGGCCC CGCGTATCCG GAGCGAGGAG TGGGCAGCGC 960
TCGGCAGAGG CCCCGGCGCG GCGGCTGCAC GTCCTCCGGG AGGAGGGAGG GAAGCCGGGC 1020
TCACCGCCGG GCCTCCCCCC CGGTCAGGAG GGAGCCGGGA ACTCCCGAGG CACCAACTCT 1080
GCGGAACGCG GGGCGCCCGG ATCGCCCCTG ATCACCGCCC GCTGGCGAGG CGCGGGGGAC 1140
CCAGAACCGG CGGGGCCGGG AGCCTCCTTT ACCGCTCCGC GCCGGGGCTG CCCGCAGGAT 1200
GGGGCGCAGG ATGGGGCGCA GGATGCGGCC CCGGCACCGC CTCGCGGGGG TCTGCGGGGG 1260
GCGACCGCGG CTCGCGTCGG CCACTACTTG GGGGTCTCGG GTTTCCGCCC CGCCCTCGCC 1320
TTGCAACCCC TCCGGCCCCG GACTCCGCTT TCCAGGCCGG GCTCTTCCCT CCGGACCCCG 1380
CTCGCCGCCC GGCGCGGCCC CCTCCTCCTG CAGCGCCCCC CGCCCCGGCG CCCGCGCCCC 1440
CGATTCGCTG CTGACTCGGT GTCTGCGCGT CCGGCCGGGC GCCCCGGGAG GAGTTTCCGG 1500
CGCGGGGCGG GGTCGGGGGC GGGGTCGGGG GCGGGGCGGG GCGGCGGGTG GGCCCCACCC 1560
CCCAGCTGAG CCCCGCCGGG CGGACTCGGA CTCGCCAACT TCAGAGGCTC GGCGGCGGCG 1620
GCGGGCGCGG AGCTCTGCGC GCGGCTCCAG CGGGCCGGGA TGGGCGGGCG GCCGCGCGGA 1680
GGACGCGGGG GGCGCGCGAC GTGACCACCC GGACTCGAAG CCCGCCCCGC CCCCGCCCGG 1740
CTCGCCGGCT CCGGGGTCTG CTCCGGGGGT CGCGGACGCG GGGCCGGGCG GCGGAGCCGG 1800
```

FIG. 1A

```
CGCCAGAGC ATG CGG GGC GCG GCG CGG GCG GCC TGG GGG CGC GCG GGG CAG   1851
          MET Arg Gly Ala Ala Arg Ala Ala Trp Gly Arg Ala Gly Gln
                          5                   10
CCG TGG CCG CGA CCC CCC GCC CCG GGC CCG CCC CCG CCG CCG CTC CCG     1899
Pro Trp Pro Arg Pro Pro Ala Pro Gly Pro Pro Pro Pro Pro Leu Pro
 15                  20                  25                  30
CTG CTG CTC CTG CTC CTG GCC GGG CTG CTG GGC GGC GCG GGC GCG CAG     1947
Leu Leu Leu Leu Leu Leu Ala Gly Leu Leu Gly Gly Ala Gly Ala Gln
                 35                  40                  45
TAC TCC AGC GAC CGG TGC AGC TGG AAG GGG AG GTGAGTGTGC GCGGCGCGAC    1999
Tyr Ser Ser Asp Arg Cys Ser Trp Lys Gly Ser
             50                  55

CCCGGCCCGG CCCCCTCCCC TCGCGTCCCC TCCCGTCCCG GGCCGGCCGA GCGTGCGGGG   2059
GCGCGGCCGG GGGCGGGCGC GGGGCAGGGG CTCCGGGGGC CGCTCTCCAG GCCCAGTCCG   2119
GTGCCCGCTG TCCCCCGCCC CCGGTTCTAG A-----------------------------     2150

GAGCTCCGGG CCTGGCTGAC AGTGTCTCTC CTCTGCAG C GGS CTG ACG CAC GAG     2204
                                            Gly Leu Thr His Glu
                                                         60
GCA CAC AGG AAG GAG GTG GAG CAG GTG TAT CTG CGC TGT GCG GCG GGT     2252
Ala His Arg Lys Glu Val Glu Gln Val Tyr Leu Arg Cys Ala Ala Gly
         65                  70                  75
GCC GTG GAG TGG ATG TAC CCA ACA GGT GCT CTC ATC GTT AAC CTG CGG     2300
Ala Val Glu Trp MET Tyr Pro Thr Gly Ala Leu Ile Val Asn Leu Arg
     80                  85                  90
CCC AAC ACM TTC TCG CCT GCC CGG CAC CTG ACC GTG TGC ATC AGG TCC     2348
Pro Asn Thr Phe Ser Pro Ala Arg His Leu Thr Val Cys Ile Arg Ser
 95                 100                 105                 110
```

FIG. 1B

```
TTC ACG GAC TCC TCG GGG GCC AAT ATT TAT TTG GAA AAA ACT GGA GAA      2396
Phe Thr Asp Ser Ser Gly Ala Asn Ile Tyr Leu Glu Lys Thr Gly Glu
                115                 120                 125
CTG AGA CTG CTG GTA CCA GAC GGG GAC GGC AGG CCC GGC CGG GTG CAG      2444
Leu Arg Leu Leu Val Pro Asp Gly Asp Gly Arg Pro Gly Arg Val Gln
            130                 135                 140
TGT TTT GGC CTG GAG CAG GGC GGC CTG TTC GTG GAG GCC ACG CCG CAG      2492
Cys Phe Gly Leu Glu Gln Gly Gly Leu Phe Val Glu Ala Thr Pro Gln
        145                 150                 155
CAG GAT ATC GGC CGG AGG ACC ACA GGC TTC CAG TAC GAG CTG GTT AGG      2540
Gln Asp Ile Gly Arg Arg Thr Thr Gly Phe Gln Tyr Glu Leu Val Arg
    160                 165                 170
AGG CAC AGG GCG TCG GAC CTG CAC GAG CTG TCT G GTGAGTGTCC TGCCTG      2590
Arg His Arg Ala Ser Asp Leu His Glu Leu Ser
175                 180                 185

--------------------- CCTCCAGCAC GTGCCGCCAA CTCACATTTG AAGTGGCGTT    2630
GGTCACAAAG GTGCCTTGAC GTGGACACCC TCCCTGACTT GGCTTTGCTG AGTGTGAGGA    2690
TCCTTTGACG GTGGTGGGCG GCGTTCCAGA GCCTGTCCCG TCCAGGCTGC TTCCTGACTC    2750

TGCCTTTCTT CTCCAG CG CCG TGC CGT CCC TGC AGT GAC ACC GAG GTG CTC     2801
                  Ala Pro Cys Arg Pro Cys Ser Asp Thr Glu Val Leu
                                  190                 195
CTA GCC GTC TGC ACC AGC GAC TTC G GTGAGTGTCT CCTCGGCAGC TTCTACC      2853
Leu Ala Val Cys Thr Ser Asp Phe

        200                 205
```

FIG. 1C

```
------------------- CCCCATCTCC TTCCCCGCAC AG CC GTT CGA GGC TCC       2889
                                            Ala Val Arg Gly Ser
                                                            210
ATC CAG CAA GTT ACC CAC GAG CCT GAG CGG CAG GAC TCA GCC ATC CAC       2937
Ile Gln Gln Val Thr His Glu Pro Glu Arg Gln Asp Ser Ala Ile His
                215                 220                 225
CTG CGC GTG AGC AGA CTC TAT CGG CAG AAA AGC AGG GTC TTC GAG CCG       2985
Leu Arg Val Ser Arg Leu Tyr Arg Gln Lys Ser Arg Val Phe Glu Pro
            230                 235                 240
GTG CCC GAG GGT GAC GGC CAC TGG CAG GGG CGC GTC AGG ACG CTG CTG       3033
Val Pro Glu Gly Asp Gly His Trp Gln Gly Arg Val Arg Thr Leu Leu
        245                 250                 255
GAG TGT GGC GTG CGG CCG GGG CAT GGC GAC TTC CTC TTC ACT GGC CAC       3081
Glu Cys Gly Val Arg Pro Gly His Gly Asp Phe Leu Phe Thr Gly His
    260                 265                 270
ATG CAC TTC GGG GAG GCG CGG CTC GGC TGT GCC CCA CGC TTC AAG GAC       3129
MET His Phe Gly Glu Ala Arg Leu Gly Cys Ala Pro Arg Phe Lys Asp
275                 280                 285                 290
TTC CAG AGG ATG TAC AGG GAT GCC CAG GAG AGG GGG CTG AAC CCT TGT       3177
Phe Gln Arg MET Tyr Arg Asp Ala Gln Glu Arg Gly Leu Asn Pro Cys
                295                 300                 305
GAG GTT GGC ACG GAC TGA CTCCGTGGGC CGCTGCCCTT CCTCTCCTGA              3225
Glu Val Gly Thr Asp
            310

TGAGTCACAG GCTGCGGTGG GCGCTGCGGT CCTGGTGGGG CCGTGCGGTG AGGGCCRCGC     3285
GCTGGGAGCC GCRTGCCCTG GGCCCAGKCC TGACCCTGGT ACCGAAGCTG TGGACGTTCT     3345
CGCCACACTC AACCCCATGA GCTTCCAGCC AAGGATGCCC TGGCCGATTG GAAATGCTGT     3405
AAAATGCAAA CTAAGTTATT ATATTTTTTT TTGGTAAAAA AGAAATGTCC ATAGGAAACA     3465
AATTCCYGTG TCTTAAAACG CCTTGGTGTG CCGTCTGATA CTGTTCTCTA AAGACGTTAG     3525
GAGTCACGGC ATCTGGCCTG CGGTTGGGTG AAGCACTGGC CGTTGGGCAC AGTGGATGTG     3585
TGAAAAGGTG CCATTCAGAG TTGTTATTCT CATGACGGAA GTTTTGGAGC CAAATAATAC     3645
GTTTTTTATT TTCATTTTAT TTTTAAAGGA TGAGCTTTGG TCCTTTTCAG GCCGCCGGTT     3705
GTTTCCGTTC CCGAGAATAA AGACGAGGAT CCGACC                               3741
```

FIG. 1D

```
GGAGC ATG CGG GGC GCG GCG CGG GCG GCA TGG GGG CGC GCG GGG CAG CCG   50
      MET Arg Gly Ala Ala Arg Ala Ala Trp Gly Arg Ala Gly Gln Pro
                      5                   10                  15
TGG CCG CGA CCC CCC GCC CCG GGC CCG CCC CCG CCG CCG CTC CCG CTG     98
Trp Pro Arg Pro Pro Ala Pro Gly Pro Pro Pro Pro Pro Leu Pro Leu
                 20                  25                  30
CTG CTC CTG CTC CTG GCC GGG CTG CTG GGC GGC GCG GGC GCG CAG TAC    146
Leu Leu Leu Leu Leu Ala Gly Leu Leu Gly Gly Ala Gly Ala Gln Tyr
             35                  40                  45
TCC AGC GAC CGG TGC AGC TGG AAG GGG AGC GGG CTG ACG CAC GAG GCA    194
Ser Ser Asp Arg Cys Ser Trp Lys Gly Ser Gly Leu Thr His Glu Ala
         50                  55                  60
CAC AGG AAG GAG GTG GAG CAG GTG TAT CTG CGC TGT GCG GCG GGT GCC    242
His Arg Lys Glu Val Glu Gln Val Tyr Leu Arg Cys Ala Ala Gly Ala
     65                  70                  75
GTG GAG TGG ATG TAC CCA ACA GGT GCT CTC ATC GTT AAC CTG CGG CCC    290
Val Glu Trp MET Tyr Pro Thr Gly Ala Leu Ile Val Asn Leu Arg Pro
 80                  85                  90                  95
AAC ACC TTC TCG CCT GCC CGG CAC CTG ACC GTG TGC ATC AGG TCC TTC    338
Asn Thr Phe Ser Pro Ala Arg His Leu Thr Val Cys Ile Arg Ser Phe
                100                 105                 110
ACG GAC TCC TCG GGG GCC AAT ATT TAT TTG GAA AAA ACT GGA GAA CTG    386
Thr Asp Ser Ser Gly Ala Asn Ile Tyr Leu Glu Lys Thr Gly Glu Leu
            115                 120                 125
AGA CTG CTG GTA CCG GAC GGG GAC GGC AGG CCC GGC CGG GTG CAG TGT    434
Arg Leu Leu Val Pro Asp Gly Asp Gly Arg Pro Gly Arg Val Gln Cys
        130                 135                 140
```

FIG. 2A

```
TTT GGC CTG GAG CAG GGC GGC CTG TTC GTG GAG GCC ACG CCG CAG CAG      482
Phe Gly Leu Glu Gln Gly Gly Leu Phe Val Glu Ala Thr Pro Gln Gln
    145                 150                 155
GAT ATC GGC CGG AGG ACC ACA GGC TTC CAG TAC GAG CTG GTT AGG AGG      530
Asp Ile Gly Arg Arg Thr Thr Gly Phe Gln Tyr Glu Leu Val Arg Arg
160                 165                 170                 175
CAC AGG GCG TCG GAC CTG CAC GAG CTG TCT GCG CCG TGC CGT CCC TGC      578
His Arg Ala Ser Asp Leu His Glu Leu Ser Ala Pro Cys Arg Pro Cys
                180                 185                 190
AGT GAC ACC GAG GTG CTC CTA GCC GTC TGC ACC AGC GAC TTC GCC GTT      626
Ser Asp Thr Glu Val Leu Leu Ala Val Cys Thr Ser Asp Phe Ala Val
            195                 200                 205
CGA GGC TCC ATC CAG CAA GTT ACC CAC GAG CCT GAG CGG CAG GAC TCA      674
Arg Gly Ser Ile Gln Gln Val Thr His Glu Pro Glu Arg Gln Asp Ser
        210                 215                 220
GCC ATC CAC CTG CGC GTG AGC AGA CTC TAT CGG CAG AAA AGC AGG GTC      722
Ala Ile His Leu Arg Val Ser Arg Leu Tyr Arg Gln Lys Ser Arg Val
    225                 230                 235
TTC GAG CCG GTG CCC GAG GGT GAC GGC CAC TGG CAG GGG CGC GTC AGG      770
Phe Glu Pro Val Pro Glu Gly Asp Gly His Trp Gln Gly Arg Val Arg
240                 245                 250                 255
ACG CTG CTG GAG TGT GGC GTG CGG CCG GGG CAT GGC GAC TTC CTC TTC      818
Thr Leu Leu Glu Cys Gly Val Arg Pro Gly His Gly Asp Phe Leu Phe
                260                 265                 270
ACT GGC CAC ATG CAC TTC GGG GAG GCG CGG CTC GGC TGT GCC CCA CGC      866
Thr Gly His MET His Phe Gly Glu Ala Arg Leu Gly Cys Ala Pro Arg
            275                 280                 285
TTC AAG GAC TTC CAG AGG ATG TAC AGG GAT GCC CAG GAG AGG GGG CTG      914
Phe Lys Asp Phe Gln Arg MET Tyr Arg Asp Ala Gln Glu Arg Gly Leu
        290                 295                 300
AAC CCT TGT GAG GTT GGC ACG GAC TGA CTCCGTGGGC CGCTGCCCTT            961
Asn Pro Cys Glu Val Gly Thr Asp
    305                 310
```

FIG. 2B

```
CCTCTCCTGA TGAGTCACAG GCTGCGGTGG GCGCTGCGGT CCTGGTGGGG CCGTGCGGTG 1021
AGGGCCACGC GCTGGGAGCC GCGTGCCCTG GGCCCAGTCC TGACCCTGGT ACCGAAGCTG 1081
TGGACGTTCT CGCCACACTC AACCCCATGA GCTTCCAGCC AAGGATGCCC TGGCCGATTG 1141
GAAATGCTGT AAAATGCAAA CTAAGTTATT ATATTTTTTT TTGGTAAAAA AGAAATGTCC 1201
ATAGGAAACA AATTCCTGTG TCTTAAAACG CCTTGGTGTG CCGTCTGATA CTGTTCTCTA 1261
AAGACGTTAG GAGTCACGGC ATCTGGCCTG CGGTTGGGTG AAGCACTGGC CGTTGGGCAC 1321
AGTGGATGTG TGAAAAGGTG CCATTCAGAG TTGTTATTCT CATGACGGAA GTTTTGGAGC 1381
CAAATAATAC GTTTTTTATT TTCATTTTAT TTTTAAAGGA TGAGCTTTGG TCCTTTTCAG 1441
GCCGCCGGTT GTTTCCGTTC CCGAGAATAA AGACGAGGAT CCGACC 1487
```

FIG. 2C

```
GCAGCCGGCG CGCTTCTCTA GTTGCAGCTT GGGCGGCTCC TGTGGTGGGC GGCTAGGGGC      60
GAGCCGGGAT GGGCTATAGA CGCGCGACGT GATCAGTTCG CACGCGGACC CACGCCTCCC     120
ATCGCTCTGC CTCAAGAGCC TATTCTGTGG GTGCAGGCAC GCACCGGACG CAGACCCGGC     180

CGGAGC ATG CGG GGT GCG GTG TGG GCG GCC CGG AGG CGC GCG GGG CAG        228
       MET Arg Gly Ala Val Trp Ala Ala Arg Arg Arg Ala Gly Gln
                        5                  10
CAG TGG CCT CGG TCC CCG GGC CCT GGG CCG GGT CCG CCC CCG CCG CCA       276
Gln Trp Pro Arg Ser Pro Gly Pro Gly Pro Gly Pro Pro Pro Pro Pro
 15                 20                  25                  30
CCG CTG CTG TTG CTG CTA CTA CTG CTG CTG GGC GGC GCG AGC GCT CAG       324
Pro Leu Leu Leu Leu Leu Leu Leu Leu Leu Gly Gly Ala Ser Ala Gln
                35                  40                  45
TAC TCC AGC GAC CTG TGC AGC TGG AAG GGG AGT GGG CTC ACC CGA GAG       372
Tyr Ser Ser Asp Leu Cys Ser Trp Lys Gly Ser Gly Leu Thr Arg Glu
            50                  55                  60
GCA CGC AGC AAG GAG GTG GAG CAG GTG TAC CTG CGC TGC TCC GCA GGC       420
Ala Arg Ser Lys Glu Val Glu Gln Val Tyr Leu Arg Cys Ser Ala Gly
        65                  70                  75
TCT GTG GAG TGG ATG TAC CCA ACT GGG GCG CTC ATT GTT AAC CTA CGG       468
Ser Val Glu Trp MET Tyr Pro Thr Gly Ala Leu Ile Val Asn Leu Arg
    80                  85                  90
CCC AAC ACC TTC TCA CCT GCC CAG AAC TTG ACT GTG TGC ATC AAG CCT       516
Pro Asn Thr Phe Ser Pro Ala Gln Asn Leu Thr Val Cys Ile Lys Pro
 95                 100                 105                 110
TTC AGG GAC TCC TCT GGA GCC AAT ATT TAT TTG GAA AAA ACT GGA GAA       564
Phe Arg Asp Ser Ser Gly Ala Asn Ile Tyr Leu Glu Lys Thr Gly Glu
                115                 120                 125
CTA AGA CTG TTG GTG CGG GAC ATC AGA GGT GAG CCT GGC CAA GTG CAG       612
Leu Arg Leu Leu Val Arg Asp Ile Arg Gly Glu Pro Gly Gln Val Gln
            130                 135                 140
```

FIG. 3A

```
TGC TTC AGC CTG GAG CAG GGA GGC TTA TTT GTG GAG GCG ACA CCC CAA        660
Cys Phe Ser Leu Glu Gln Gly Gly Leu Phe Val Glu Ala Thr Pro Gln
        145                 150                 155
CAG GAC ATC AGC AGA AGG ACC ACA GGC TTC CAG TAT GAG CTG ATG AGT        708
Gln Asp Ile Ser Arg Arg Thr Thr Gly Phe Gln Tyr Glu Leu MET Ser
    160                 165                 170
GGG CAG AGG GGA CTG GAC CTG CAC GTG CTG TCT GCC CCC TGT CGG CCT        756
Gly Gln Arg Gly Leu Asp Leu His Val Leu Ser Ala Pro Cys Arg Pro
175                 180                 185                 190
TGC AGT GAC ACT GAG GTC CTC CTT GCC ATC TGT ACC AGT GAC TTT GTT        804
Cys Ser Asp Thr Glu Val Leu Leu Ala Ile Cys Thr Ser Asp Phe Val
                195                 200                 205
GTC CGA GGC TTC ATT GAG GAC GTC ACA CAT GTA CCA GAA CAG CAA GTG        852
Val Arg Gly Phe Ile Glu Asp Val Thr His Val Pro Glu Gln Gln Val
            210                 215                 220
TCA GTC ATC TAC CTG CGG GTG AAC AGG CTT CAC AGG CAG AAG AGC AGG        900
Ser Val Ile Tyr Leu Arg Val Asn Arg Leu His Arg Gln Lys Ser Arg
        225                 230                 235
GTC TTC CAG CCA GCT CCT GAG GAC AGT GGC CAC TGG CTG GGC CAT GTC        948
Val Phe Gln Pro Ala Pro Glu Asp Ser Gly His Trp Leu Gly His Val
    240                 245                 250
ACA ACA CTG CTG CAG TGT GGA GTA CGA CCA GGG CAT GGG GAA TTC CTC        996
Thr Thr Leu Leu Gln Cys Gly Val Arg Pro Gly His Gly Glu Phe Leu
255                 260                 265                 270
TTC ACT GGA CAT GTG CAC TTT GGG GAG GCA CAA CTT GGA TGT GCC CCA       1044
Phe Thr Gly His Val His Phe Gly Glu Ala Gln Leu Gly Cys Ala Pro
                275                 280                 285
CGC TTT AGT GAC TTT CAA AGG ATG TAC AGG AAA GCA GAA GAA ATG GGC       1092
Arg Phe Ser Asp Phe Gln Arg MET Tyr Arg Lys Ala Glu Glu MET Gly
            290                 295                 300
ATA AAC CCC TGT GAA ATC AAT ATG GAG TGA CTTGCAGGGT GACACAGTAC         1142
Ile Asn Pro Cys Glu Ile Asn MET Glu
        305                 310

TGTTGTCCTT CAGATGAGCC ATGTTTTGTG GGCTCAGTCG CTCTATCATA TCCTGATAGA     1202
GATTGCAGAC TGGTGGCATG GGCCCAGCCT GGTGCTAGAA CTGGGAAGGT ACATGCTGCT     1262
CTGACCCCTT AGGTCCCAGC CAAGGATGCC CTGACCCATT GGAACTGCTG TAAAATGCAA     1322
ACTAAGTTAT TATATTTTTT TTGTAAAAGA AAAAAAAAAA                           1362
```

FIG. 3B

```
human   Met Arg Gly Ala Ala Arg Ala Ala Trp Gly Arg Ala Gly Gln Pro   15
         |   |   |   |           |   |           |   |   |   |
mouse   Met Arg Gly Ala Val Trp Ala Ala Arg Arg Arg Ala Gly Gln Gln   15

human   Trp Pro Arg Pro Pro Ala Pro Gly Pro Pro Pro Pro Pro Leu Pro   30
         |   |   |       |       |   |   |       |   |   |       |
mouse   Trp Pro Arg Ser Pro Gly Pro Gly Pro Gly Pro Pro Pro Pro Pro   30

human   Leu Leu Leu Leu Leu Leu Ala Gly Leu Leu Gly Gly Ala Gly Ala   45
             |   |   |   |   |           |   |   |   |   |       |
mouse   Pro Leu Leu Leu Leu Leu Leu Leu Leu Leu Gly Gly Ala Ser Ala   45

human   Gln Tyr Ser Ser Asp Arg Cys Ser Trp Lys Gly Ser Gly Leu Thr   60
         |   |   |   |   |       |   |   |   |   |   |   |   |   |
mouse   Gln Tyr Ser Ser Asp Leu Cys Ser Trp Lys Gly Ser Gly Leu Thr   60

human   His Glu Ala His Arg Lys Glu Val Glu Gln Val Tyr Leu Arg Cys   75
             |   |           |   |   |   |   |   |   |   |   |   |
mouse   Arg Glu Ala Arg Ser Lys Glu Val Glu Gln Val Tyr Leu Arg Cys   75
```

FIG. 5A

```
human   Ala Ala Gly Ala Val Glu Trp Met Tyr Pro Thr Gly Ala Leu Ile    90
mouse   Ser Ala Gly Ser Val Glu Trp Met Tyr Pro Thr Gly Ala Leu Ile    90

human   Val Asn Leu Arg Pro Asn Thr Phe Ser Pro Ala Arg His Leu Thr   105
mouse   Val Asn Leu Arg Pro Asn Thr Phe Ser Pro Ala Gln Asn Leu Thr   105

human   Val Cys Ile Arg Ser Phe Thr Asp Ser Ser Gly Ala Asn Ile Tyr   120
mouse   Val Cys Ile Lys Pro Phe Arg Asp Ser Ser Gly Ala Asn Ile Tyr   120

human   Leu Glu Lys Thr Gly Glu Leu Arg Leu Leu Val Pro Asp Gly Asp   135
mouse   Leu Glu Lys Thr Gly Glu Leu Arg Leu Leu Val Arg Asp Ile Arg   135

human   Gly Arg Pro Gly Arg Val Gln Cys Phe Gly Leu Glu Gln Gly Gly   150
mouse   Gly Glu Pro Gly Gln Val Gln Cys Phe Ser Leu Glu Gln Gly Gly   150

human   Leu Phe Val Glu Ala Thr Pro Gln Gln Asp Ile Gly Arg Arg Thr   165
mouse   Leu Phe Val Glu Ala Thr Pro Gln Gln Asp Ile Ser Arg Arg Thr   165

human   Thr Gly Phe Gln Tyr Glu Leu Val Arg Arg His Arg Ala Ser Asp   180
mouse   Thr Gly Phe Gln Tyr Glu Leu Met Ser Gly Gln Arg Gly Leu Asp   180
```

FIG. 5B

```
human   Leu His Glu Leu Ser Ala Pro Cys Arg Pro Cys Ser Asp Thr Glu   195
mouse   Leu His Val Leu Ser Ala Pro Cys Arg Pro Cys Ser Asp Thr Glu   195

human   Val Leu Leu Ala Val Cys Thr Ser Asp Phe Ala Val Arg Gly Ser   210
mouse   Val Leu Leu Ala Ile Cys Thr Ser Asp Phe Val Val Arg Gly Phe   210

human   Ile Gln Gln Val Thr His Glu Pro Glu Arg Gln Asp Ser Ala Ile   225
mouse   Ile Glu Asp Val Thr His Val Pro Glu Gln Gln Val Ser Val Ile   225

human   His Leu Arg Val Ser Arg Leu Tyr Arg Gln Lys Ser Arg Val Phe   240
mouse   Tyr Leu Arg Val Asn Arg Leu His Arg Gln Lys Ser Arg Val Phe   240

human   Glu Pro Val Pro Glu Gly Asp Gly His Trp Gln Gly Arg Val Arg   255
mouse   Gln Pro Ala Pro Glu Asp Ser Gly His Trp Leu Gly His Val Thr   255

human   Thr Leu Leu Glu Cys Gly Val Arg Pro Gly His Gly Asp Phe Leu   270
mouse   Thr Leu Leu Gln Cys Gly Val Arg Pro Gly His Gly Glu Phe Leu   270

human   Phe Thr Gly His Met His Phe Gly Glu Ala Arg Leu Gly Cys Ala   285
mouse   Phe Thr Gly His Val His Phe Gly Glu Ala Gln Leu Gly Cys Ala   285

human   Pro Arg Phe Lys Asp Phe Gln Arg Met Tyr Arg Asp Ala Gln Glu   300
mouse   Pro Arg Phe Ser Asp Phe Gln Arg Met Tyr Arg Lys Ala Glu Glu   300

human   Arg Gly Leu Asn Pro Cys Glu Val Gly Thr Asp                   311
mouse   Met Gly Ile Asn Pro Cys Glu Ile Asn Met Glu                   311
```

FIG. 5C

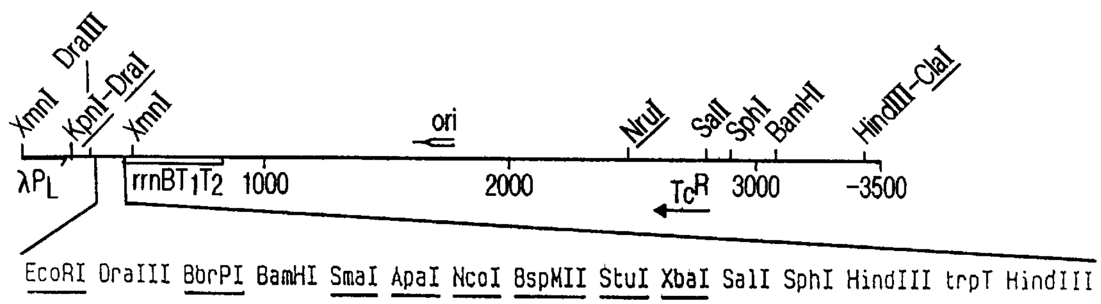

mTNF(AA pos 81 to 103)

```
ATG GTA AGA TCA AGT AGT CAA AAT TCG AGT GAC AAG CCT GTA GCC CAC
Met Val Arg Ser Ser Ser Gln Asn Ser Ser Asp Lys Pro Val Ala His

                                        EcoRI
GTC GTA GCA AAC CAC CAA GTG GAG GAG CAG GGA ATT CAC CAT CAC CAT
Val Val Ala Asn His Gln Val Glu Glu Gln Gly Ile His His His His

    BprPI          ApaI
   Dra III   BamHI SmaI     NcoI      BspMII   StuI
CAC CAC GTG GAT CCC GGG CCC ATG GCT TTC CGG AGG CCT
His His Val Asp Pro Gly Pro Met Ala Phe Arg Arg Pro

            formic acid     CnBr   kallikrein
                                     protease VII
```

FIG. 8A

```
AATTCCGGGG ATCTCTCACC TACCAAACAA TGCCCCCCTG CAAAAAATAA ATTCATATAA   60
AAAACATACA GATAACCATC TGCGGTGATA AATTATCTCT GGCGGTGTTG ACATAAATAC  120
CACTGGCGGT GATACTGAGC ACATCAGCAG GACGCACTGA CCACCATGAA GGTGACGCTC  180
TTAAAAATTA AGCCCTGAAG AAGGGCAGGG GTACCAGGAG GTTTAAATCA TGGTAAGATC  240
AAGTAGTCAA AATTCGAGTG ACAAGCCTGT AGCCCACGTC GTAGCAAACC ACCAAGTGGA  300
GGAGCAGGGA ATTCACCATC ACCATCACCA CGTGGATCCC GGGCCCATGG CTTTCCGGAG  360
GCCTCTAGAG TCGACCGGCA TGCAAGCTTA AGTAAGTAAG CCGCCAGTTC CGCTGGCGGC  420
ATTTTTTTTG ATGCCCAAGC TTGGCTGTTT TGGCGGATGA GAGAAGATTT TCAGCCTGAT  480
ACAGATTAAA TCAGAACGCA GAAGCGGTCT GATAAAACAG AATTTGCCTG GCGGCAGTAG  540
CGCGGTGGTC CCACCTGACC CCATGCCGAA CTCAGAAGTG AAACGCCGTA GCGCCGATGG  600
TAGTGTGGGG TCTCCCCATG CGAGAGTAGG GAACTGCCAG GCATCAAATA AAACGAAAGG  660
CTCAGTCGAA AGACTGGGCC TTTCGTTTTA TCTGTTGTTT GTCGGTGAAC GCTCTCCTGA  720
GTAGGACAAA TCCGCCGGGA GCGGATTTGA ACGTTGCGAA GCAACGGCCC GGAGGGTGGC  780
GGGCAGGACG CCCGCCATAA ACTGCCAGGC ATCAAATTAA GCAGAAGGCC ATCCTGACGG  840
ATGGCCTTTT TGCGTTTCTA CAAACTCTTT TGTTTATTTT TCTAAATACA TTCAAATATG  900
TATCCGCTCA TGAGACAATA ACCCTGATAA ATGCTTCAAT AATAAAAGGA TCTAGGTGAA  960
GATCCTTTTT GATAATCTCA TGACCAAAAT CCCTTAACGT GAGTTTTCGT TCCACTGAGC 1020
GTCAGACCCC GTAGAAAAGA TCAAAGGATC TTCTTGAGAT CCTTTTTTTC TGCGCGTAAT 1080
CTGCTGCTTG CAAACAAAAA AACCACCGCT ACCAGCGGTG GTTTGTTTGC CGGATCAAGA 1140
GCTACCAACT CTTTTTCCGA AGGTAACTGG CTTCAGCAGA GCGCAGATAC CAAATACTGT 1200
CCTTCTAGTG TAGCCGTAGT TAGGCCACCA CTTCAAGAAC TCTGTAGCAC CGCCTACATA 1260
CCTCGCTCTG CTAATCCTGT TACCAGTGGC TGCTGCCAGT GGCGATAAGT CGTGTCTTAC 1320
CGGGTTGGAC TCAAGACGAT AGTTACCGGA TAAGGCGCAG CGGTCGGGCT GAACGGGGGG 1380
TTCGTGCACA CAGCCCAGCT TGGAGCGAAC GACCTACACC GAACTGAGAT ACCTACAGCG 1440
TGAGCATTGA GAAAGCGCCA CGCTTCCCGA AGGGAGAAAG GCGGACAGGT ATCCGGTAAG 1500
CGGCAGGGTC GGAACAGGAG AGCGCACGAG GGAGCTTCCA GGGGGAAACG CCTGGTATCT 1560
TTATAGTCCT GTCGGGTTTC GCCACCTCTG ACTTGAGCGT CGATTTTTGT GATGCTCGTC 1620
AGGGGGGCGG AGCCTATGGA AAAACGCCAG CAACGCGGCC TTTTTACGGT TCCTGGCCTT 1680
TTGCTGGCCT TTTGCTCACA TGTTCTTTCC TGCGTTATCC CCTGATTCTG TGGATAACCG 1740
TATTACCGCC TTTGAGTGAG CTGATACCGC TCGCCGCAGC CGAACGACCG AGCGCAGCGA 1800
GTCAGTGAGC GAGGAAGCGG AAGAGCGCTG ACTTCCGCGT TTCCAGACTT TACGAAACAC 1860
GGAAACCGAA GACCATTCAT GTTGTTGCTC AGGTCGCAGA CGTTTTGCAG CAGCAGTCGC 1920
TTCACGTTCG CTCGCGTATC GGTGATTCAT TCTGCTAACC AGTAAGGCAA CCCCGCCAGC 1980
CTAGCCGGGT CCTCAACGAC AGGAGCACGA TCATGCGCAC CCGTGGCCAG GACCCAACGC 2040
TGCCCGAGAT GCGCCGCGTG CGGCTGCTGG AGATGGCGGA CGCGATGGAT ATGTTCTGCC 2100
AAGGGTTGGT TTGCGCATTC ACAGTTCTCC GCAAGAATTG ATTGGCTCCA ATTCTTGGAG 2160
TGGTGAATCC GTTAGCGAGG TGCCGCCGGC TTCCATTCAG GTCGAGGTGG CCCGGCTCCA 2220
```

FIG. 8B-1

```
TGCACCGCGA CGCAACGCGG GGAGGCAGAC AAGGTATAGG GCGGCGCCTA CAATCCATGC 2280
CAACCCGTTC CATGTGCTCG CCGAGGCGGC ATAAATCGCC GTGACGATCA GCGGTCCAGT 2340
GATCGAAGTT AGGCTGGTAA GAGCCGCGAG CGATCCTTGA AGCTGTCCCT GATGGTCGTC 2400
ATCTACCTGC CTGGACAGCA TGGCCTGCAA CGCGGGCATC CCGATGCCGC CGGAAGCGAG 2460
AAGAATCATA ATGGGGAAGG CCATCCAGCC TCGCGTCGCG AACGCCAGCA AGACGTAGCC 2520
CAGCGCGTCG GCCGCCATGC CGGCGATAAT GGCCTGCTTC TCGCCGAAAC GTTTGGTGGC 2580
GGGACCAGTG ACGAAGGCTT GAGCGAGGGC GTGCAAGATT CCGAATACCG CAAGCGACAG 2640
GCCGATCATC GTCGCGCTCC AGCGAAAGCG GTCCTCGCCG AAAATGACCC AGAGCGCTGC 2700
CGGCACCTGT CCTACGAGTT GCATGATAAA GAAGACAGTC ATAAGTGCGG CGACGATAGT 2760
CATGCCCCGC GCCCACCGGA AGGAGCTGAC TGGGTTGAAG GCTCTCAAGG GCATCGGTCG 2820
ACGCTCTCCC TTATGCGACT CCTGCATTAG GAAGCAGCCC AGTAGTAGGT TGAGGCCGTT 2880
GAGCACCGCC GCCGCAAGGA ATGGTGCATG CAAGGAGATG GCGCCCAACA GTCCCCCGGC 2940
CACGGGGCCT GCCACCATAC CCACGCCGAA ACAAGCGCTC ATGAGCCCGA AGTGGCGAGC 3000
CCGATCTTCC CCATCGGTGA TGTCGGCGAT ATAGGCGCCA GCAACCGCAC CTGTGGCGCC 3060
GGTGATGCCG GCCACGATGC GTCCGGCGTA GAGGATCCAC AGGACGGGTG TGGTCGCCAT 3120

GATCGCGTAG TCGATAGTGG CTCCAAGTAG CGAAGCGAGC AGGACTGGGC GGCGGCCAAA 3180
GCGGTCGGAC AGTGCTCCGA GAACGGGTGC GCATAGAAAT TGCATCAACG CATATAGCGC 3240
TAGCAGCACG CCATAGTGAC TGGCGATGCT GTCGGAATGG ACGATATCCC GCAAGAGGCC 3300
CGGCAGTACC GGCATAACCA AGCCTATGCC TACAGCATCC AGGGTGACGG TGCCGAGGAT 3360
GACGATGAGC GCATTGTTAG ATTTCATACA CGGTGCCTGA CTGCGTTAGC AATTTAACTG 3420
TGATAAACTA CCGCATTAAA GCTTATCGAT GATAAGCTGT CAAACATGAG AATT 3474
```

FIG. 8B-2

PU 5.1.8-CM:+LPS

SEQUENCE LISTING

```
(1) GENERAL INFORMATION:

   (iii) NUMBER OF SEQUENCES: 53


(2) INFORMATION FOR SEQ ID NO: 1:

     (i) SEQUENCE CHARACTERISTICS:
          (A) LENGTH: 2150 base pairs
          (B) TYPE: nucleic acid
          (C) STRANDEDNESS: single
          (D) TOPOLOGY: linear

    (ii) MOLECULE TYPE: DNA(genomic)
```

(iii) HYPOTHETICAL: NO (iv) ANTI-SENSE: NO (vi) ORIGINAL SOURCE:
(A) ORGANISM: Human
(F) TISSUE TYPE: Spleen tissue from healthy human (ix) FEATURE:
(A) NAME/KEY: CDS
(B) LOCATION: 1810..1982

(ix) FEATURE:
(A) NAME/KEY: misc_feature
(B) LOCATION: 543
(D) OTHER INFORMATION: C may be present or absent (ix) FEATURE:
(A) NAME/KEY: intron
(B) LOCATION: 1980..2150

(ix) FEATURE:
(A) NAME/KEY: 5'UTR
(B) LOCATION: 1..1809

(xi) SEQUENCE DESCRIPTION: SEQ ID NO: 1:

```
GGTACCTGCA GTGATGGGGG TGGGGGGAGG TGCACTCCTA GAGCAGAGGG GGGTGGGTGG     60
GGCAGTCTCC AAGCTCCGAA ATGCACCTCC ACCAGATCTT GAGCCTCAGG GTGATGTCAC    120
TTGATGTGCT GGGCAAGGTC CTGGCTCCAG GCTTTCGATG GGGTGGGTGC TCTGAACACA    180
TCCTTACAAT GAAACTACCT TCAGTGGTCA CTGTCATCGC CTTCCAGTTC TTCAGACCCT    240
CACCCTTGTC CCAGCTTTCC TGGGCTGGGG GCTGGGCTCC ACCTGCCTTT GCCGGTGACT    300
TCCGTCCCTG CAGACTCACA ATTTTCAAAG CCCTCTCCCC GCCTCCTCTG GTAGTCACAA    360
CCCAGTTATT CAGACTTGCA CAGGTCGTTC GCAAGTCCTC CTGGAAGGTA TCTTGGCTGG    420
AAAAGGGGAC AAGGCCAAGC TTCCCCACCG CTGGATGCTG CGCTCGGCTC TGGAACTGAC    480
ACCAGGCGTC TCGGGCAGGG CCACTGACCC GCAGCACACA GAAGCCAGCT TTGCCATCGC    540
AGCGGGGACC GCCGGGCGGG CCASSTCCGC CCTCTCCTGC CTGGGGGGCC CTCGGCACCC    600
TCTGGCTCCC CTTCTCTGGC CTGAGTCTCT AGGGCCTCCC CAGTCCGGGC GGGGGTCTCC    660
GCTGTCCCCC CAACTGGGTC AGGCACGTGG TGGCCGCGGT GACCACCTGG GGAAGGCGCC    720
GACTCCGAGG AACACACTCG AGCAGGACGC TCCGCAGGTG ATTCTGCCCC GCGGGCACGG    780
GGTGGGGGCG GGATTTGGCC AAATCTGCAG AGAGTTTAGG TTGTCAAAGC TGGGGCGGGG    840
GTTGCTACTG ATACCCAGAG TGCGGGGGCC AGGGTGCTGC CAACATCCCA CCATGCGCAG    900
GACGTCCCCA CCCCAAGAAC CACCCGGCCC CGCGTATCCG GAGCGAGGAG TGGGCAGCGC    960
TCGGCAGAGG CCCCGGCGCG GCGGCTGCAC GTCCTCCGGG AGGAGGGAGG GAAGCCGGGC   1020
TCACCGCCGG GCCTCCCCCC CGGTCAGGAG GGAGCCGGGA ACTCCCGAGG CACCAACTCT   1080
GCGGAACGCG GGGCGCCCGG ATCGCCCCTG ATCACCGCCC GCTGGCGAGG CGCGGGGGAC   1140
CCAGAACCGG CGGGGCCGGG AGCCTCCTTT ACCGCTCCGC GCCGGGGCTG CCCGCAGGAT   1200
GGGGCGCAGG ATGGGGCGCA GGATGCGGCC CCGGCACCGC CTCGCGGGGG TCTGCGGGGG   1260
GCGACCGCGG CTCGCGTCGG CCACTACTTG GGGGTCTCGG GTTTCCGCCC CGCCCTCGCC   1320
TTGCAACCCC TCCGGCCCCG GACTCCGCTT TCCAGGCCGG GCTCTTCCCT CCGGACCCCG   1380
CTCGCCGCCC GGCGCGGCCC CCTCCTCCTG CAGCGCCCCC CGCCCCGGCG CCCGCGCCCC   1440
CGATTCGCTG CTGACTCGGT GTCTGCGCGT CCGGCCGGGC GCCCCGGGAG GAGTTTCCGG   1500
CGCGGGGCGG GGTCGGGGGC GGGGTCGGGG GCGGGGCGGG GCGGCGGGTG GGCCCCACCC   1560
```

-continued

```
CCCAGCTGAG CCCGGCCGGG CGGACTCGGA CTCGCCAACT TCAGAGGCTC GGCGGCGGCG   1620

GCGGGCGCGG AGCTCTGCGC GCGGCTCCAG CGGGCCGGGA TGGGCGGGCG GCCGCGCGGA   1680

GGACGCGGGG GGCGCGCGAC GTGACCACCC GGACTCGAAG CCCGCCCCGC CCCCGCCCGG   1740

CTCGCCGGCT CCGGGGTCTG CTCCGGGGGT CGCGGACGCG GGGCCGGGCG GCGGAGCCGG   1800

CGCCAGAGCA TGCGGGGCGC GGCGCGGGCG GCCTGGGGGC GCGCGGGGCA GCCGTGGCCG   1860

CGACCCCCCG CCCCGGGCCC GCCCCCGCCG CCGCTCCCGC TGCTGCTCCT GCTCCTGGCC   1920

GGGCTGCTGG GCGGCGCGGG CGCGCAGTAC TCCAGCGACC GGTGCAGCTG GAAGGGGAGG   1980

TGAGTGTGCG CGGCGCGACC CCGGCCCGGC CCCCTCCCCT CGCGTCCCCT CCCGTCCCGG   2040

GCCGGCCGAG CGTGCGGGGG CGCGGCCGGG GGCGGGCGCG GGGCAGGGGC TCCGGGGGCC   2100

GCTCTCCAGG CCCAGTCCGG TGCCCGCTGT CCCCCGCCCC CGGTTCTAGA              2150
```

(2) INFORMATION FOR SEQ ID NO: 2:

(i) SEQUENCE CHARACTERISTICS:
(A) LENGTH: 440 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Human
(F) TISSUE TYPE: Spleen tissue from healthy human (ix) FEATURE:
(A) NAME/KEY: intron
(B) LOCATION: 1..41

(ix) FEATURE:
(A) NAME/KEY: CDS
(B) LOCATION: 42..426

(ix) FEATURE:
(A) NAME/KEY: intron
(B) LOCATION: 424..440

(xi) SEQUENCE DESCRIPTION: SEQ ID NO: 2:

```
GAGCTCCGGG CCTGGCTGAC AGTGTCTCTC CTCTGCAGCG GSCTGACGCA CGAGGCACAC     60

AGGAAGGAGG TGGAGCAGGT GTATCTGCGC TGTGCGGCGG GTGCCGTGGA GTGGATGTAC    120

CCAACAGGTG CTCTCATCGT TAACCTGCGG CCCAACACMT TCTCGCCTGC CCGGCACCTG    180

ACCGTGTGCA TCAGGTCCTT CACGGACTCC TCGGGGGCCA ATATTTATTT GGAAAAAACT    240

GGAGAACTGA GACTGCTGGT ACCAGACGGG GACGGCAGGC CCGGCCGGGT GCAGTGTTTT    300

GGCCTGGAGC AGGGCGGCCT GTTCGTGGAG GCCACGCCGC AGCAGGATAT CGGCCGGAGG    360

ACCACAGGCT TCCAGTACGA GCTGGTTAGG AGGCACAGGG CGTCGGACCT GCACGAGCTG    420

TCTGGTGAGT GTCCTGCCTG    440
```

(2) INFORMATION FOR SEQ ID NO: 3:

(i) SEQUENCE CHARACTERISTICS:
(A) LENGTH: 263 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Human
(F) TISSUE TYPE: Spleen tissue from healthy human (ix) FEATURE:
(A) NAME/KEY: intron
(B) LOCATION: 1..175

(ix) FEATURE:
(A) NAME/KEY: CDS
(B) LOCATION: 176..238

(ix) FEATURE:
(A) NAME/KEY: intron
(B) LOCATION: 236..263

(xi) SEQUENCE DESCRIPTION: SEQ ID NO: 3:

```
CCTCCAGCAC GTGCCGCCAA CTCACATTTG AAGTGGCGTT GGTCACAAAG GTGCCTTGAC     60

GTGGACACCC TCCCTGACTT GGCTTTGCTG AGTGTGAGGA TCCTTTGACG GTGGTGGGCG    120

GCGTTCCAGA GCCTGTCCCG TCCAGGCTGC TTCCTGACTC TGCCTTTCTT CTCCA GCG     178
                                                             Ala
                                                             1

CCG TGC CGT CCC TGC AGT GAC ACC GAG GTG CTC CTA GCC GTC TGC ACC      226
Pro Cys Arg Pro Cys Ser Asp Thr Glu Val Leu Leu Ala Val Cys Thr
            5                  10                  15

AGC GAC TTC GGTGAGTGTC TCCTCGGCAG CTTCTACC                           263
Ser Asp Phe
        20
```

(2) INFORMATION FOR SEQ ID NO: 4:

(i) SEQUENCE CHARACTERISTICS:
(A) LENGTH: 20 amino acids
(B) TYPE: amino acid
(D) TOPOLOGY: linear (ii) MOLECULE TYPE: protein (xi) SEQUENCE DESCRIPTION: SEQ ID NO: 4:

```
Ala Pro Cys Arg Pro Cys Ser Asp Thr Glu Val Leu Leu Ala Val Cys
  1               5                  10                  15

Thr Ser Asp Phe
            20
```

(2) INFORMATION FOR SEQ ID NO: 5:

(i) SEQUENCE CHARACTERISTICS:
(A) LENGTH: 888 base pairs
(B) TYPE: nucleic acid
(C) STRANDEDNESS: single
(D) TOPOLOGY: linear (ii) MOLECULE TYPE: DNA(genomic)

(iii) HYPOTHETICAL: NO (iv) ANTI-SENSE: NO (vi) ORIGINAL SOURCE:
(A) ORGANISM: Human
(F) TISSUE TYPE: Spleen tissue from healthy human (ix) FEATURE:
(A) NAME/KEY: intron
(B) LOCATION: 1..21

(ix) FEATURE:

(A) NAME/KEY: CDS
(B) LOCATION: 22..342

(ix) FEATURE:
(A) NAME/KEY: 3'UTR
(B) LOCATION: 340..888

(ix) FEATURE:
(A) NAME/KEY: polyA_site
(B) LOCATION: 868..873

(xi) SEQUENCE DESCRIPTION: SEQ ID NO: 5:

```
CCCCATCTCC TTCCCCGCAC AGCCGTTCGA GGCTCCATCC AGCAAGTTAC CCACGAGCCT     60

GAGCGGCAGG ACTCAGCCAT CCACCTGCGC GTGAGCAGAC TCTATCGGCA GAAAAGCAGG    120

GTCTTCGAGC CGGTGCCCGA GGGTGACGGC CACTGGCAGG GGCGCGTCAG GACGCTGCTG    180

GAGTGTGGCG TGCGGCCGGG GCATGGCGAC TTCCTCTTCA CTGGCCACAT GCACTTCGGG    240

GAGGCGCGGC TCGGCTGTGC CCCACGCTTC AAGGACTTCC AGAGGATGTA CAGGGATGCC    300

CAGGAGAGGG GGCTGAACCC TTGTGAGGTT GGCACGGACT GACTCCGTGG GCCGCTGCCC    360

TTCCTCTCCT GATGAGTCAC AGGCTGCGGT GGGCGCTGCG GTCCTGGTGG GGCCGTGCGG    420

TGAGGGCCRC GCGCTGGGAG CCGCRTGCCC TGGGCCCAGK CCTGACCCTG GTACCGAAGC    480

TGTGGACGTT CTCGCCACAC TCAACCCCAT GAGCTTCCAG CCAAGGATGC CCTGGCCGAT    540

TGGAAATGCT GTAAAATGCA AACTAAGTTA TTATATTTTT TTTTGGTAAA AAAGAAATGT    600

CCATAGGAAA CAAATTCCYG TGTCTTAAAA CGCCTTGGTG TGCCGTCTGA TACTGTTCTC    660

TAAAGACGTT AGGAGTCACG GCATCTGGCC TGCGGTTGGG TGAAGCACTG GCCGTTGGGC    720

ACAGTGGATG TGTGAAAAGG TGCCATTCAG AGTTGTTATT CTCATGACGG AAGTTTTGGA    780

GCCAAATAAT ACGTTTTTTA TTTTCATTTT ATTTTTAAAG GATGAGCTTT GGTCCTTTTC    840

AGGCCGCCGG TTGTTTCCGT TCCCGAGAAT AAAGACGAGG ATCCGACC                 888
```

(2) INFORMATION FOR SEQ ID NO:6:

(i) SEQUENCE CHARACTERISTICS:
(A) LENGTH: 1487 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Human
(H) CELL LINE: THP-1

(ix) FEATURE:
(A) NAME/KEY: 5'UTR
(B) LOCATION: 1..5

(ix) FEATURE:
(A) NAME/KEY: sig_peptide (B) LOCATION: 6..140

(ix) FEATURE:
(A) NAME/KEY: mat_peptide (B) LOCATION: 141..938

(ix) FEATURE:
(A) NAME/KEY: 3'UTR
(B) LOCATION: 939..1487

(ix) FEATURE:
(A) NAME/KEY: CDS
(B) LOCATION: 6..941

-continued (xi) SEQUENCE DESCRIPTION: SEQ ID NO: 6:

```
GGAGC ATG CGG GGC GCG GCG CGG GCG GCA TGG GGG CGC GCG GGG CAG        47
      Met Arg Gly Ala Ala Arg Ala Ala Trp Gly Arg Ala Gly Gln
      -45                -40                 -35

CCG TGG CCG CGA CCC CCC GCC CCG GGC CCG CCC CCG CCG CCG CTC CCG      95
Pro Trp Pro Arg Pro Pro Ala Pro Gly Pro Pro Pro Pro Pro Leu Pro
    -30                 -25                 -20

CTG CTG CTC CTG CTC CTG GCC GGG CTG CTG GGC GGC GCG GGC GCG CAG     143
Leu Leu Leu Leu Leu Leu Ala Gly Leu Leu Gly Gly Ala Gly Ala Gln
-15                 -10                  -5                   1

TAC TCC AGC GAC CGG TGC AGC TGG AAG GGG AGC GGG CTG ACG CAC GAG     191
Tyr Ser Ser Asp Arg Cys Ser Trp Lys Gly Ser Gly Leu Thr His Glu
              5                  10                  15

GCA CAC AGG AAG GAG GTG GAG CAG GTG TAT CTG CGC TGT GCG GCG GGT     239
Ala His Arg Lys Glu Val Glu Gln Val Tyr Leu Arg Cys Ala Ala Gly
         20                  25                  30

GCC GTG GAG TGG ATG TAC CCA ACA GGT GCT CTC ATC GTT AAC CTG CGG     287
Ala Val Glu Trp Met Tyr Pro Thr Gly Ala Leu Ile Val Asn Leu Arg
     35                  40                  45

CCC AAC ACC TTC TCG CCT GCC CGG CAC CTG ACC GTG TGC ATC AGG TCC     335
Pro Asn Thr Phe Ser Pro Ala Arg His Leu Thr Val Cys Ile Arg Ser
 50                  55                  60                  65

TTC ACG GAC TCC TCG GGG GCC AAT ATT TAT TTG GAA AAA ACT GGA GAA     383
Phe Thr Asp Ser Ser Gly Ala Asn Ile Tyr Leu Glu Lys Thr Gly Glu
                 70                  75                  80

CTG AGA CTG CTG GTA CCG GAC GGG GAC GGC AGG CCC GGC CGG GTG CAG     431
Leu Arg Leu Leu Val Pro Asp Gly Asp Gly Arg Pro Gly Arg Val Gln
             85                  90                  95

TGT TTT GGC CTG GAG CAG GGC GGC CTG TTC GTG GAG GCC ACG CCG CAG     479
Cys Phe Gly Leu Glu Gln Gly Gly Leu Phe Val Glu Ala Thr Pro Gln
        100                 105                 110

CAG GAT ATC GGC CGG AGG ACC ACA GGC TTC CAG TAC GAG CTG GTT AGG     527
Gln Asp Ile Gly Arg Arg Thr Thr Gly Phe Gln Tyr Glu Leu Val Arg
    115                 120                 125

AGG CAC AGG GCG TCG GAC CTG CAC GAG CTG TCT GCG CCG TGC CGT CCC     575
Arg His Arg Ala Ser Asp Leu His Glu Leu Ser Ala Pro Cys Arg Pro
130                 135                 140                 145

TGC AGT GAC ACC GAG GTG CTC CTA GCC GTC TGC ACC AGC GAC TTC GCC     623
Cys Ser Asp Thr Glu Val Leu Leu Ala Val Cys Thr Ser Asp Phe Ala
                150                 155                 160

GTT CGA GGC TCC ATC CAG CAA GTT ACC CAC GAG CCT GAG CGG CAG GAC     671
Val Arg Gly Ser Ile Gln Gln Val Thr His Glu Pro Glu Arg Gln Asp
            165                 170                 175

TCA GCC ATC CAC CTG CGC GTG AGC AGA CTC TAT CGG CAG AAA AGC AGG     719
Ser Ala Ile His Leu Arg Val Ser Arg Leu Tyr Arg Gln Lys Ser Arg
        180                 185                 190

GTC TTC GAG CCG GTG CCC GAG GGT GAC GGC CAC TGG CAG GGG CGC GTC     767
Val Phe Glu Pro Val Pro Glu Gly Asp Gly His Trp Gln Gly Arg Val
    195                 200                 205

AGG ACG CTG CTG GAG TGT GGC GTG CGG CCG GGG CAT GGC GAC TTC CTC     815
Arg Thr Leu Leu Glu Cys Gly Val Arg Pro Gly His Gly Asp Phe Leu
210                 215                 220                 225

TTC ACT GGC CAC ATG CAC TTC GGG GAG GCG CGG CTC GGC TGT GCC CCA     863
Phe Thr Gly His Met His Phe Gly Glu Ala Arg Leu Gly Cys Ala Pro
                230                 235                 240

CGC TTC AAG GAC TTC CAG AGG ATG TAC AGG GAT GCC CAG GAG AGG GGG     911
Arg Phe Lys Asp Phe Gln Arg Met Tyr Arg Asp Ala Gln Glu Arg Gly
            245                 250                 255

CTG AAC CCT TGT GAG GTT GGC ACG GAC TGACTCCGTG GGCCGCTGCC           958
Leu Asn Pro Cys Glu Val Gly Thr Asp
```

```
        260                 265

CTTCCTCTCC TGATGAGTCA CAGGCTGCGG TGGGCGCTGC GGTCCTGGTG GGGCCGTGCG   1018

GTGAGGGCCA CGCGCTGGGA GCCGCGTGCC CTGGGCCCAG TCCTGACCCT GGTACCGAAG   1078

CTGTGGACGT TCTCGCCACA CTCAACCCCA TGAGCTTCCA GCCAAGGATG CCCTGGCCGA   1138

TTGGAAATGC TGTAAAATGC AAACTAAGTT ATTATATTTT TTTTTGGTAA AAAAGAAATG   1198

TCCATAGGAA ACAAATTCCT GTGTCTTAAA ACGCCTTGGT GTGCCGTCTG ATACTGTTCT   1258

CTAAAGACGT TAGGAGTCAC GGCATCTGGC CTGCGGTTGG GTGAAGCACT GGCCGTTGGG   1318

CACAGTGGAT GTGTGAAAAG GTGCCATTCA GAGTTGTTAT TCTCATGACG GAAGTTTTGG   1378

AGCCAAATAA TACGTTTTTT ATTTTCATTT TATTTTTAAA GGATGAGCTT TGGTCCTTTT   1438

CAGGCCGCCG GTTGTTTCCG TTCCCGAGAA TAAAGACGAG GATCCGACC               1487
```

(2) INFORMATION FOR SEQ ID NO: 7:

(i) SEQUENCE CHARACTERISTICS:
(A) LENGTH: 311 amino acids
(B) TYPE: amino acid
(D) TOPOLOGY: linear (ii) MOLECULE TYPE: protein (xi) SEQUENCE DESCRIPTION: SEQ ID NO: 7:

```
Met Arg Gly Ala Ala Arg Ala Ala Trp Gly Arg Ala Gly Gln Pro Trp
-45                 -40                 -35                 -30

Pro Arg Pro Pro Ala Pro Gly Pro Pro Pro Pro Pro Leu Pro Leu Leu
                -25                 -20                 -15

Leu Leu Leu Leu Ala Gly Leu Leu Gly Gly Ala Gly Ala Gln Tyr Ser
            -10                 -5                  1

Ser Asp Arg Cys Ser Trp Lys Gly Ser Gly Leu Thr His Glu Ala His
    5                   10                  15

Arg Lys Glu Val Glu Gln Val Tyr Leu Arg Cys Ala Ala Gly Ala Val
20                  25                  30                  35

Glu Trp Met Tyr Pro Thr Gly Ala Leu Ile Val Asn Leu Arg Pro Asn
                40                  45                  50

Thr Phe Ser Pro Ala Arg His Leu Thr Val Cys Ile Arg Ser Phe Thr
            55                  60                  65

Asp Ser Ser Gly Ala Asn Ile Tyr Leu Glu Lys Thr Gly Glu Leu Arg
     70                  75                  80

Leu Leu Val Pro Asp Gly Asp Gly Arg Pro Gly Arg Val Gln Cys Phe
    85                  90                  95

Gly Leu Glu Gln Gly Gly Leu Phe Val Glu Ala Thr Pro Gln Gln Asp
100                 105                 110                 115

Ile Gly Arg Arg Thr Thr Gly Phe Gln Tyr Glu Leu Val Arg Arg His
                120                 125                 130

Arg Ala Ser Asp Leu His Glu Leu Ser Ala Pro Cys Arg Pro Cys Ser
            135                 140                 145

Asp Thr Glu Val Leu Leu Ala Val Cys Thr Ser Asp Phe Ala Val Arg
        150                 155                 160

Gly Ser Ile Gln Gln Val Thr His Glu Pro Glu Arg Gln Asp Ser Ala
    165                 170                 175

Ile His Leu Arg Val Ser Arg Leu Tyr Arg Gln Lys Ser Arg Val Phe
180                 185                 190                 195

Glu Pro Val Pro Glu Gly Asp Gly His Trp Gln Gly Arg Val Arg Thr
                200                 205                 210
```

```
Leu Leu Glu Cys Gly Val Arg Pro Gly His Gly Asp Phe Leu Phe Thr
            215                 220                 225

Gly His Met His Phe Gly Glu Ala Arg Leu Gly Cys Ala Pro Arg Phe
        230                 235                 240

Lys Asp Phe Gln Arg Met Tyr Arg Asp Ala Gln Glu Arg Gly Leu Asn
    245                 250                 255

Pro Cys Glu Val Gly Thr Asp
260                 265
```

(2) INFORMATION FOR SEQ ID NO: 8:

(i) SEQUENCE CHARACTERISTICS:
(A) LENGTH: 1362 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Mouse
(H) CELL LINE: PU5-1.8

(ix) FEATURE:
(A) NAME/KEY: 5'UTR
(B) LOCATION: 1..186

(ix) FEATURE:
(A) NAME/KEY: sig_peptide
(B) LOCATION: 187..321

(ix) FEATURE:
(A) NAME/KEY: mat_peptide
(B) LOCATION: 322..1119

(ix) FEATURE:
(A) NAME/KEY: 3'UTR
(B) LOCATION: 1120..1362

(ix) FEATURE:
(A) NAME/KEY: CDS
(B) LOCATION: 187..1122

(xi) SEQUENCE DESCRIPTION: SEQ ID NO: 8:

```
GCAGCCGGCG CGCTTCTCTA GTTGCAGCTT GGGCGGCTCC TGTGGTGGGC GGCTAGGGGC      60

GAGCCGGGAT GGGCTATAGA CGCGCGACGT GATCAGTTCG CACGCGGACC CACGCCTCCC     120

ATCGCTCTGC CTCAAGAGCC TATTCTGTGG GTGCAGGCAC GCACCGGACG CAGACCCGGC     180

CGGAGC ATG CGG GGT GCG GTG TGG GCG GCC CGG AGG CGC GCG GGG CAG        228
       Met Arg Gly Ala Val Trp Ala Ala Arg Arg Arg Ala Gly Gln
       -45                 -40                 -35

CAG TGG CCT CGG TCC CCG GGC CCT GGG CCG GGT CCG CCC CCG CCG CCA       276
Gln Trp Pro Arg Ser Pro Gly Pro Gly Pro Gly Pro Pro Pro Pro Pro
    -30                 -25                 -20

CCG CTG CTG TTG CTG CTA CTA CTG CTG CTG GGC GGC GCG AGC GCT CAG       324
Pro Leu Leu Leu Leu Leu Leu Leu Leu Leu Gly Gly Ala Ser Ala Gln
-15                 -10                  -5                   1

TAC TCC AGC GAC CTG TGC AGC TGG AAG GGG AGT GGG CTC ACC CGA GAG       372
Tyr Ser Ser Asp Leu Cys Ser Trp Lys Gly Ser Gly Leu Thr Arg Glu
              5                  10                  15

GCA CGC AGC AAG GAG GTG GAG CAG GTG TAC CTG CGC TGC TCC GCA GGC       420
Ala Arg Ser Lys Glu Val Glu Gln Val Tyr Leu Arg Cys Ser Ala Gly
         20                  25                  30

TCT GTG GAG TGG ATG TAC CCA ACT GGG GCG CTC ATT GTT AAC CTA CGG       468
```

```
Ser Val Glu Trp Met Tyr Pro Thr Gly Ala Leu Ile Val Asn Leu Arg
     35                  40                  45

CCC AAC ACC TTC TCA CCT GCC CAG AAC TTG ACT GTG TGC ATC AAG CCT      516
Pro Asn Thr Phe Ser Pro Ala Gln Asn Leu Thr Val Cys Ile Lys Pro
 50                  55                  60                  65

TTC AGG GAC TCC TCT GGA GCC AAT ATT TAT TTG GAA AAA ACT GGA GAA      564
Phe Arg Asp Ser Ser Gly Ala Asn Ile Tyr Leu Glu Lys Thr Gly Glu
                 70                  75                  80

CTA AGA CTG TTG GTG CGG GAC ATC AGA GGT GAG CCT GGC CAA GTG CAG      612
Leu Arg Leu Leu Val Arg Asp Ile Arg Gly Glu Pro Gly Gln Val Gln
             85                  90                  95

TGC TTC AGC CTG GAG CAG GGA GGC TTA TTT GTG GAG GCG ACA CCC CAA      660
Cys Phe Ser Leu Glu Gln Gly Gly Leu Phe Val Glu Ala Thr Pro Gln
        100                 105                 110

CAG GAC ATC AGC AGA AGG ACC ACA GGC TTC CAG TAT GAG CTG ATG AGT      708
Gln Asp Ile Ser Arg Arg Thr Thr Gly Phe Gln Tyr Glu Leu Met Ser
    115                 120                 125

GGG CAG AGG GGA CTG GAC CTG CAC GTG CTG TCT GCC CCC TGT CGG CCT      756
Gly Gln Arg Gly Leu Asp Leu His Val Leu Ser Ala Pro Cys Arg Pro
130                 135                 140                 145

TGC AGT GAC ACT GAG GTC CTC CTT GCC ATC TGT ACC AGT GAC TTT GTT      804
Cys Ser Asp Thr Glu Val Leu Leu Ala Ile Cys Thr Ser Asp Phe Val
                150                 155                 160

GTC CGA GGC TTC ATT GAG GAC GTC ACA CAT GTA CCA GAA CAG CAA GTG      852
Val Arg Gly Phe Ile Glu Asp Val Thr His Val Pro Glu Gln Gln Val
            165                 170                 175

TCA GTC ATC TAC CTG CGG GTG AAC AGG CTT CAC AGG CAG AAG AGC AGG      900
Ser Val Ile Tyr Leu Arg Val Asn Arg Leu His Arg Gln Lys Ser Arg
        180                 185                 190

GTC TTC CAG CCA GCT CCT GAG GAC AGT GGC CAC TGG CTG GGC CAT GTC      948
Val Phe Gln Pro Ala Pro Glu Asp Ser Gly His Trp Leu Gly His Val
    195                 200                 205

ACA ACA CTG CTG CAG TGT GGA GTA CGA CCA GGG CAT GGG GAA TTC CTC      996
Thr Thr Leu Leu Gln Cys Gly Val Arg Pro Gly His Gly Glu Phe Leu
210                 215                 220                 225

TTC ACT GGA CAT GTG CAC TTT GGG GAG GCA CAA CTT GGA TGT GCC CCA     1044
Phe Thr Gly His Val His Phe Gly Glu Ala Gln Leu Gly Cys Ala Pro
                230                 235                 240

CGC TTT AGT GAC TTT CAA AGG ATG TAC AGG AAA GCA GAA GAA ATG GGC     1092
Arg Phe Ser Asp Phe Gln Arg Met Tyr Arg Lys Ala Glu Glu Met Gly
            245                 250                 255

ATA AAC CCC TGT GAA ATC AAT ATG GAG TGACTTGCAG GGTGACACAG           1139
Ile Asn Pro Cys Glu Ile Asn Met Glu
        260                 265

TACTGTTGTC CTTCAGATGA GCCATGTTTT GTGGGCTCAG TCGCTCTATC ATATCCTGAT   1199

AGAGATTGCA GACTGGTGGC ATGGGCCCAG CCTGGTGCTA GAACTGGGAA GGTACATGCT   1259

GCTCTGACCC CTTAGGTCCC AGCCAAGGAT GCCCTGACCC ATTGGAACTG CTGTAAAATG   1319

CAAACTAAGT TATTATATTT TTTTTGTAAA AGAAAAAAAA AAA                      1362
```

(2) INFORMATION FOR SEQ ID NO: 9:

(i) SEQUENCE CHARACTERISTICS:
- (A) LENGTH: 311 amino acids
- (B) TYPE: amino acid
- (D) TOPOLOGY: linear (ii) MOLECULE TYPE: protein (xi) SEQUENCE DESCRIPTION: SEQ ID NO: 9:

```
Met Arg Gly Ala Val Trp Ala Ala Arg Arg Arg Ala Gly Gln Gln Trp
```

```
-45                 -40                 -35                 -30

Pro Arg Ser Pro Gly Pro Gly Pro Gly Pro Pro Pro Pro Pro Pro Leu
                -25                 -20                 -15

Leu Leu Leu Leu Leu Leu Leu Leu Gly Gly Ala Ser Ala Gln Tyr Ser
            -10                 -5                   1

Ser Asp Leu Cys Ser Trp Lys Gly Ser Gly Leu Thr Arg Glu Ala Arg
     5                  10                  15

Ser Lys Glu Val Glu Gln Val Tyr Leu Arg Cys Ser Ala Gly Ser Val
 20                  25                  30                  35

Glu Trp Met Tyr Pro Thr Gly Ala Leu Ile Val Asn Leu Arg Pro Asn
                 40                  45                  50

Thr Phe Ser Pro Ala Gln Asn Leu Thr Val Cys Ile Lys Pro Phe Arg
             55                  60                  65

Asp Ser Ser Gly Ala Asn Ile Tyr Leu Glu Lys Thr Gly Glu Leu Arg
         70                  75                  80

Leu Leu Val Arg Asp Ile Arg Gly Glu Pro Gly Gln Val Gln Cys Phe
     85                  90                  95

Ser Leu Glu Gln Gly Gly Leu Phe Val Glu Ala Thr Pro Gln Gln Asp
100                 105                 110                 115

Ile Ser Arg Arg Thr Thr Gly Phe Gln Tyr Glu Leu Met Ser Gly Gln
                120                 125                 130

Arg Gly Leu Asp Leu His Val Leu Ser Ala Pro Cys Arg Pro Cys Ser
            135                 140                 145

Asp Thr Glu Val Leu Leu Ala Ile Cys Thr Ser Asp Phe Val Val Arg
        150                 155                 160

Gly Phe Ile Glu Asp Val Thr His Val Pro Glu Gln Gln Val Ser Val
    165                 170                 175

Ile Tyr Leu Arg Val Asn Arg Leu His Arg Gln Lys Ser Arg Val Phe
180                 185                 190                 195

Gln Pro Ala Pro Glu Asp Ser Gly His Trp Leu Gly His Val Thr Thr
                200                 205                 210

Leu Leu Gln Cys Gly Val Arg Pro Gly His Gly Glu Phe Leu Phe Thr
            215                 220                 225

Gly His Val His Phe Gly Glu Ala Gln Leu Gly Cys Ala Pro Arg Phe
        230                 235                 240

Ser Asp Phe Gln Arg Met Tyr Arg Lys Ala Glu Glu Met Gly Ile Asn
    245                 250                 255

Pro Cys Glu Ile Asn Met Glu
260                 265
```

(2) INFORMATION FOR SEQ ID NO: 10:

(i) SEQUENCE CHARACTERISTICS:
(A) LENGTH: 3474 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vii) IMMEDIATE SOURCE:
(B) CLONE: pmTNF-MPH (xi) SEQUENCE DESCRIPTION: SEQ ID NO: 10:

```
AATTCCGGGG ATCTCTCACC TACCAAACAA TGCCCCCCTG CAAAAAATAA ATTCATATAA     60
```

```
AAAACATACA GATAACCATC TGCGGTGATA AATTATCTCT GGCGGTGTTG ACATAAATAC    120
CACTGGCGGT GATACTGAGC ACATCAGCAG GACGCACTGA CCACCATGAA GGTGACGCTC    180
TTAAAAATTA AGCCCTGAAG AAGGGCAGGG GTACCAGGAG GTTTAAATCA TGGTAAGATC    240
AAGTAGTCAA AATTCGAGTG ACAAGCCTGT AGCCCACGTC GTAGCAAACC ACCAAGTGGA    300
GGAGCAGGGA ATTCACCATC ACCATCACCA CGTGGATCCC GGGCCCATGG CTTTCCGGAG    360
GCCTCTAGAG TCGACCGGCA TGCAAGCTTA AGTAAGTAAG CCGCCAGTTC CGCTGGCGGC    420
ATTTTTTTTG ATGCCCAAGC TTGGCTGTTT TGGCGGATGA GAGAAGATTT TCAGCCTGAT    480
ACAGATTAAA TCAGAACGCA GAAGCGGTCT GATAAAACAG AATTTGCCTG GCGGCAGTAG    540
CGCGGTGGTC CCACCTGACC CCATGCCGAA CTCAGAAGTG AAACGCCGTA GCGCCGATGG    600
TAGTGTGGGG TCTCCCCATG CGAGAGTAGG GAACTGCCAG GCATCAAATA AAACGAAAGG    660
CTCAGTCGAA AGACTGGGCC TTTCGTTTTA TCTGTTGTTT GTCGGTGAAC GCTCTCCTGA    720
GTAGGACAAA TCCGCCGGGA GCGGATTTGA ACGTTGCGAA GCAACGGCCC GGAGGGTGGC    780
GGGCAGGACG CCCGCCATAA ACTGCCAGGC ATCAAATTAA GCAGAAGGCC ATCCTGACGG    840
ATGGCCTTTT TGCGTTTCTA CAAACTCTTT TGTTTATTTT TCTAAATACA TTCAAATATG    900
TATCCGCTCA TGAGACAATA ACCCTGATAA ATGCTTCAAT AATAAAAGGA TCTAGGTGAA    960
GATCCTTTTT GATAATCTCA TGACCAAAAT CCCTTAACGT GAGTTTTCGT TCCACTGAGC   1020
GTCAGACCCC GTAGAAAAGA TCAAAGGATC TTCTTGAGAT CCTTTTTTTC TGCGCGTAAT   1080
CTGCTGCTTG CAAACAAAAA AACCACCGCT ACCAGCGGTG GTTTGTTTGC CGGATCAAGA   1140
GCTACCAACT CTTTTTCCGA AGGTAACTGG CTTCAGCAGA GCGCAGATAC CAAATACTGT   1200
CCTTCTAGTG TAGCCGTAGT TAGGCCACCA CTTCAAGAAC TCTGTAGCAC CGCCTACATA   1260
CCTCGCTCTG CTAATCCTGT TACCAGTGGC TGCTGCCAGT GGCGATAAGT CGTGTCTTAC   1320
CGGGTTGGAC TCAAGACGAT AGTTACCGGA TAAGGCGCAG CGGTCGGGCT GAACGGGGGG   1380
TTCGTGCACA CAGCCCAGCT TGGAGCGAAC GACCTACACC GAACTGAGAT ACCTACAGCG   1440
TGAGCATTGA GAAAGCGCCA CGCTTCCCGA AGGGAGAAAG GCGGACAGGT ATCCGGTAAG   1500
CGGCAGGGTC GGAACAGGAG AGCGCACGAG GGAGCTTCCA GGGGGAAACG CCTGGTATCT   1560
TTATAGTCCT GTCGGGTTTC GCCACCTCTG ACTTGAGCGT CGATTTTTGT GATGCTCGTC   1620
AGGGGGGCGG AGCCTATGGA AAAACGCCAG CAACGCGGCC TTTTTACGGT TCCTGGCCTT   1680
TTGCTGGCCT TTTGCTCACA TGTTCTTTCC TGCGTTATCC CCTGATTCTG TGGATAACCG   1740
TATTACCGCC TTTGAGTGAG CTGATACCGC TCGCCGCAGC CGAACGACCG AGCGCAGCGA   1800
GTCAGTGAGC GAGGAAGCGG AAGAGCGCTG ACTTCCGCGT TTCCAGACTT TACGAAACAC   1860
GGAAACCGAA GACCATTCAT GTTGTTGCTC AGGTCGCAGA CGTTTTGCAG CAGCAGTCGC   1920
TTCACGTTCG CTCGCGTATC GGTGATTCAT TCTGCTAACC AGTAAGGCAA CCCCGCCAGC   1980
CTAGCCGGGT CCTCAACGAC AGGAGCACGA TCATGCGCAC CCGTGGCCAG GACCCAACGC   2040
TGCCCGAGAT GCGCCGCGTG CGGCTGCTGG AGATGGCGGA CGCGATGGAT ATGTTCTGCC   2100
AAGGGTTGGT TTGCGCATTC ACAGTTCTCC GCAAGAATTG ATTGGCTCCA ATTCTTGGAG   2160
TGGTGAATCC GTTAGCGAGG TGCCGCCGGC TTCCATTCAG GTCGAGGTGG CCCGGCTCCA   2220
TGCACCGCGA CGCAACGCGG GGAGGCAGAC AAGGTATAGG GCGGCGCCTA CAATCCATGC   2280
CAACCCGTTC CATGTGCTCG CCGAGGCGGC ATAAATCGCC GTGACGATCA GCGGTCCAGT   2340
GATCGAAGTT AGGCTGGTAA GAGCCGCGAG CGATCCTTGA AGCTGTCCCT GATGGTCGTC   2400
ATCTACCTGC CTGGACAGCA TGGCCTGCAA CGCGGGCATC CCGATGCCGC CGGAAGCGAG   2460
```

```
AAGAATCATA ATGGGGAAGG CCATCCAGCC TCGCGTCGCG AACGCCAGCA AGACGTAGCC   2520

CAGCGCGTCG GCCGCCATGC CGGCGATAAT GGCCTGCTTC TCGCCGAAAC GTTTGGTGGC   2580

GGGACCAGTG ACGAAGGCTT GAGCGAGGGC GTGCAAGATT CCGAATACCG CAAGCGACAG   2640

GCCGATCATC GTCGCGCTCC AGCGAAAGCG GTCCTCGCCG AAAATGACCC AGAGCGCTGC   2700

CGGCACCTGT CCTACGAGTT GCATGATAAA GAAGACAGTC ATAAGTGCGG CGACGATAGT   2760

CATGCCCCGC GCCCACCGGA AGGAGCTGAC TGGGTTGAAG GCTCTCAAGG GCATCGGTCG   2820

ACGCTCTCCC TTATGCGACT CCTGCATTAG GAAGCAGCCC AGTAGTAGGT TGAGGCCGTT   2880

GAGCACCGCC GCCGCAAGGA ATGGTGCATG CAAGGAGATG GCGCCCAACA GTCCCCCGGC   2940

CACGGGGCCT GCCACCATAC CCACGCCGAA ACAAGCGCTC ATGAGCCCGA AGTGGCGAGC   3000

CCGATCTTCC CCATCGGTGA TGTCGGCGAT ATAGGCGCCA GCAACCGCAC CTGTGGCGCC   3060

GGTGATGCCG GCCACGATGC GTCCGGCGTA GAGGATCCAC AGGACGGGTG TGGTCGCCAT   3120

GATCGCGTAG TCGATAGTGG CTCCAAGTAG CGAAGCGAGC AGGACTGGGC GGCGGCCAAA   3180

GCGGTCGGAC AGTGCTCCGA GAACGGGTGC GCATAGAAAT TGCATCAACG CATATAGCGC   3240

TAGCAGCACG CCATAGTGAC TGGCGATGCT GTCGGAATGG ACGATATCCC GCAAGAGGCC   3300

CGGCAGTACC GGCATAACCA AGCCTATGCC TACAGCATCC AGGGTGACGG TGCCGAGGAT   3360

GACGATGAGC GCATTGTTAG ATTTCATACA CGGTGCCTGA CTGCGTTAGC AATTTAACTG   3420

TGATAAACTA CCGCATTAAA GCTTATCGAT GATAAGCTGT CAAACATGAG AATT         3474
```

(2) INFORMATION FOR SEQ ID NO: 11:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse
(H) CELL LINE: PU51.8

(xi) SEQUENCE DESCRIPTION: SEQ ID NO: 11:

```
Cys Ser Trp Lys Gly Ser Gly Leu Thr Arg Glu Ala Arg Ser Lys Glu
               5                  10                  15

Val Glu Gln Val Tyr Leu Arg Cys
            20
```

(2) INFORMATION FOR SEQ ID NO: 12:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse
(H) CELL LINE: PU5-1.8

(xi) SEQUENCE DESCRIPTION: SEQ ID NO: 12:

```
Arg Glu Ala Arg Ser Lys Glu Val Glu
```

1 5

(2) INFORMATION FOR SEQ ID NO: 13:

(i) SEQUENCE CHARACTERISTICS:
(A) LENGTH: 37 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse
(H) CELL LINE: PU5-1.8

(xi) SEQUENCE DESCRIPTION: SEQ ID NO: 13:

```
Cys Ile Lys Pro Phe Arg Asp Ser Ser Gly Ala Asn Ile Tyr Leu Glu
1               5                   10                  15

Lys Thr Gly Glu Leu Arg Leu Leu Val Arg Asp Ile Arg Gly Glu Pro
            20                  25                  30

Gly Gln Val Gln Cys
        35
```

(2) INFORMATION FOR SEQ ID NO: 14:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse
(H) CELL LINE: PU5-1.8

(xi) SEQUENCE DESCRIPTION: SEQ ID NO: 14:

```
Arg Asp Ile Arg Gly Glu
1                   5
```

(2) INFORMATION FOR SEQ ID NO: 15:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (v) FRAGMENT TYPE: C-terminal (vi) ORIGINAL SOURCE:
(A) ORGANISM: Mouse
(H) CELL LINE: PU5-1.8

(xi) SEQUENCE DESCRIPTION: SEQ ID NO: 15:

```
Gly Cys Ala Pro Arg Phe Ser Asp Phe Gln Arg Met Tyr Arg Lys Ala
1               5                   10                  15

Glu Glu Met Gly Ile Asn Pro Cys Glu Ile Asn Met Glu
            20                  25
```

(2) INFORMATION FOR SEQ ID NO: 16:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse
(H) CELL LINE: PU5-1.8

(xi) SEQUENCE DESCRIPTION: SEQ ID NO: 16:

```
Arg Lys Ala Glu Glu
1               5
```

(2) INFORMATION FOR SEQ ID NO: 17:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Human
(H) CELL LINE: THP-1

(xi) SEQUENCE DESCRIPTION: SEQ ID NO: 17:

```
Cys Ser Trp Lys Gly Ser Gly Leu Thr His Glu Ala His Arg Lys Glu
1               5                   10                  15

Val Glu Gln Val Tyr Leu Arg Cys
            20
```

(2) INFORMATION FOR SEQ ID NO: 18:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Human
(H) CELL LINE: THP-1

(xi) SEQUENCE DESCRIPTION: SEQ ID NO: 18:

```
Arg Lys Glu Val Glu
1               5
```

(2) INFORMATION FOR SEQ ID NO: 19:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:

(A) ORGANISM: Human
(H) CELL LINE: THP-1

(xi) SEQUENCE DESCRIPTION: SEQ ID NO: 19:

```
Cys Thr Ser Asp Phe Ala Val Arg Gly Ser Ile Gln Gln Val Thr His
1               5                   10                  15

Glu Pro Glu Arg Gln Asp Ser Ala Ile His Leu Arg Val Ser Arg
            20                  25                  30
```

(2) INFORMATION FOR SEQ ID NO: 20:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Human
(H) CELL LINE: THP-1

(xi) SEQUENCE DESCRIPTION: SEQ ID NO: 20:

```
Glu Pro Glu Arg Gln Asp
1               5
```

(2) INFORMATION FOR SEQ ID NO: 21:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (v) FRAGMENT TYPE: C-terminal (vi) ORIGINAL SOURCE:
(A) ORGANISM: Human
(H) CELL LINE: THP-1

(xi) SEQUENCE DESCRIPTION: SEQ ID NO: 21:

```
Gly Cys Ala Pro Arg Phe Lys Asp Phe Gln Arg Met Tyr Arg Asp Ala
1               5                   10                  15

Gln Glu Arg Gly Leu Asn Pro Cys Glu Val Gly Thr Asp
            20                  25
```

(2) INFORMATION FOR SEQ ID NO: 22:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Human
(H) CELL LINE: THP-1

(xi) SEQUENCE DESCRIPTION: SEQ ID NO: 22:

```
Arg Asp Ala Gln Glu Arg
1               5
```

(2) INFORMATION FOR SEQ ID NO: 23:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 23:

```
Cys Ser Trp Lys Gly Ser Gly Leu Thr
1               5
```

(2) INFORMATION FOR SEQ ID NO: 24:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 24:

```
Val Glu Trp Met Tyr Pro Thr Gly Ala Leu Ile Val Asn Leu Arg Pro
1               5                   10                  15

Asn Thr Phe Ser Pro Ala
            20
```

(2) INFORMATION FOR SEQ ID NO: 25:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 25:

```
Asp Ser Ser Gly Ala Asn Ile Tyr Leu Glu Lys Thr Gly Glu Leu Arg
1               5                   10                  15

Leu Leu Val
```

(2) INFORMATION FOR SEQ ID NO: 26:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 26:

```
Leu Glu Gln Gly Gly Leu Phe Val Glu Ala Thr Pro Gln Gln Asp Ile
1               5                   10                  15
```

(2) INFORMATION FOR SEQ ID NO: 27:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 27:

```
Arg Arg Thr Thr Gly Phe Gln Tyr Glu Leu
1               5                   10
```

(2) INFORMATION FOR SEQ ID NO: 28:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 28:

```
Leu Ser Ala Pro Cys Arg Pro Cys Ser Asp Thr Glu Val Leu Leu Ala
1               5                   10                  15
```

(2) INFORMATION FOR SEQ ID NO: 29:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 29:

```
Arg Gln Lys Ser Arg Val Phe
1               5
```

(2) INFORMATION FOR SEQ ID NO: 30:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 30:

```
Cys Gly Val Arg Pro Gly His Gly
1               5
```

(2) INFORMATION FOR SEQ ID NO: 31:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 31:

```
Phe Leu Phe Thr Gly His
1               5
```

(2) INFORMATION FOR SEQ ID NO: 32:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human
(H) CELL LINE: PU5-1.8, THP-1

(xi) SEQUENCE DESCRIPTION: SEQ ID NO: 32:

```
Leu Gly Cys Ala Pro Arg Phe
1               5
```

(2) INFORMATION FOR SEQ ID NO: 33:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Mouse, human (H) CELL LINE: PU5-1.8, THP-1

(xi) SEQUENCE DESCRIPTION: SEQ ID NO: 33:

Asp Phe Gln Arg Met Tyr Arg
1 5

(2) INFORMATION FOR SEQ ID NO: 34:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Mouse
(H) CELL LINE: PU5-1.8

(xi) SEQUENCE DESCRIPTION: SEQ ID NO: 34:

AGGGAGGCTT ATTTGTGGAG G 21

(2) INFORMATION FOR SEQ ID NO: 35:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (iv) ANTI-SENSE: YES (vi) ORIGINAL SOURCE:
(A) ORGANISM: Mouse
(H) CELL LINE: PU5-1.8

(xi) SEQUENCE DESCRIPTION: SEQ ID NO: 35:

GGATATGATA GAGCGACTGA GC 22

(2) INFORMATION FOR SEQ ID NO: 36:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Mouse
(H) CELL LINE: PU5-1.8

(xi) SEQUENCE DESCRIPTION: SEQ ID NO: 36:

CCGAGAGGCA CGCAGCAAGG A 21

(2) INFORMATION FOR SEQ ID NO: 37:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (iv) ANTI-SENSE: YES (vi) ORIGINAL SOURCE:
(A) ORGANISM: Mouse
(H) CELL LINE: PU5-1.8

(xi) SEQUENCE DESCRIPTION: SEQ ID NO: 37:

CCGACAGGGG GCAGACAGCA CG 22

(2) INFORMATION FOR SEQ ID NO: 38:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Human
(H) CELL LINE: THP-1

(xi) SEQUENCE DESCRIPTION: SEQ ID NO: 38:

GCTGCTCCTG CTCCTGGCCG G 21

(2) INFORMATION FOR SEQ ID NO: 39:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iv) ANTI-SENSE: YES (vi) ORIGINAL SOURCE:
(A) ORGANISM: Human
(H) CELL LINE: THP-1

(xi) SEQUENCE DESCRIPTION: SEQ ID NO: 39:

GGTCCGACGC CCTGTGCCTC 20

(2) INFORMATION FOR SEQ ID NO: 40:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Human
(H) CELL LINE: THP-1

(xi) SEQUENCE DESCRIPTION: SEQ ID NO: 40:

AGTGGATGTA CCCAACAGG 19

(2) INFORMATION FOR SEQ ID NO: 41:

(i) SEQUENCE CHARACTERISTICS:
(A) LENGTH: 21 base pairs
(B) TYPE: nucleic acid (C) STRANDEDNESS: single
(D) TOPOLOGY: linear (ii) MOLECULE TYPE: cDNA (iv) ANTI-SENSE: YES (vi) ORIGINAL SOURCE:
(A) ORGANISM: Human
(H) CELL LINE: THP-1

(xi) SEQUENCE DESCRIPTION: SEQ ID NO: 41:

TACCAGCAGT CTCAGTTCTC C 21

(2) INFORMATION FOR SEQ ID NO: 42:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Human
(H) CELL LINE: THP-1

(xi) SEQUENCE DESCRIPTION: SEQ ID NO: 42:

TTCACGGACT CCTCGGGGGC CAATA 25

(2) INFORMATION FOR SEQ ID NO: 43:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Human
(H) CELL LINE: THP-1

(xi) SEQUENCE DESCRIPTION: SEQ ID NO: 43:

TGGCCTGGAG CAGGGCGGCC TGTTC 25

(2) INFORMATION FOR SEQ ID NO: 44:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Human
(H) CELL LINE: THP-1

(xi) SEQUENCE DESCRIPTION: SEQ ID NO: 44:

ACAGGCTTCC AGTACGAGCT GGTTA 25

(2) INFORMATION FOR SEQ ID NO: 45:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Mouse
(H) CELL LINE: PU5-1.8

(xi) SEQUENCE DESCRIPTION: SEQ ID NO: 45:

GGGCTCACCC GAGAGGCACG CAGCA 25

(2) INFORMATION FOR SEQ ID NO: 46:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Mouse
(H) CELL LINE: PU5-1.8

(xi) SEQUENCE DESCRIPTION: SEQ ID NO: 46:

ATCAAGCCTT TCAGGGACTC CTCTG 25

(2) INFORMATION FOR SEQ ID NO: 47:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iv) ANTI-SENSE: NO (vi) ORIGINAL SOURCE:
(A) ORGANISM: Mouse
(H) CELL LINE: PU5-1.8

(xi) SEQUENCE DESCRIPTION: SEQ ID NO: 47:

AACAGGCTTC ACAGGCAGAA GAGCA 25

(2) INFORMATION FOR SEQ ID NO: 48:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: cDNA (iv) ANTI-SENSE: YES (vi) ORIGINAL SOURCE:
(A) ORGANISM: Mouse
(H) CELL LINE: PU5-1.8

(xi) SEQUENCE DESCRIPTION: SEQ ID NO: 48:

```
CACCGCACCC CGCAT                                                        15

(2) INFORMATION FOR SEQ ID NO: 49:

     (i) SEQUENCE CHARACTERISTICS:
          (A) LENGTH: 7 base pairs
          (B) TYPE: nucleic acid
          (C) STRANDEDNESS: single
          (D) TOPOLOGY: linear

    (ii) MOLECULE TYPE: DNA (genomic)

         (xi) SEQUENCE DESCRIPTION: SEQ ID NO: 49:

TTATTAT                                                                  7

(2) INFORMATION FOR SEQ ID NO: 50:

     (i) SEQUENCE CHARACTERISTICS:
          (A) LENGTH: 57 amino acids
          (B) TYPE: amino acid
          (C) STRANDEDNESS: single
          (D) TOPOLOGY: linear

    (ii) MOLECULE TYPE: protein

   (iii) HYPOTHETICAL: NO

     (v) FRAGMENT TYPE: N-terminal

    (vi) ORIGINAL SOURCE:
          (A) ORGANISM: Human
          (F) TISSUE TYPE: Spleen tissue from healthy human

   (vii) IMMEDIATE SOURCE:
          (B) CLONE: SEQ ID NO 1

         (xi) SEQUENCE DESCRIPTION: SEQ ID NO: 50:

Met Arg Gly Ala Ala Arg Ala Ala Trp Gly Arg Ala Gly Gln Pro Trp
1               5                   10                  15

Pro Arg Pro Pro Ala Pro Gly Pro Pro Pro Pro Pro Leu Pro Leu Leu
            20                  25                  30

Leu Leu Leu Leu Ala Gly Leu Leu Gly Gly Ala Gly Ala Gln Tyr Ser
        35                  40                  45

Ser Asp Arg Cys Ser Trp Lys Gly Ser
    50                  55

(2) INFORMATION FOR SEQ ID NO: 51:

     (i) SEQUENCE CHARACTERISTICS:
          (A) LENGTH: 128 amino acids
          (B) TYPE: amino acid
          (C) STRANDEDNESS: single
          (D) TOPOLOGY: linear

    (ii) MOLECULE TYPE: protein

   (iii) HYPOTHETICAL: NO

     (v) FRAGMENT TYPE: internal

    (vi) ORIGINAL SOURCE:
          (A) ORGANISM: Human
          (F) TISSUE TYPE: Spleen tissue from healthy human

   (vii) IMMEDIATE SOURCE:
          (B) CLONE: SEQ ID NO 2

         (xi) SEQUENCE DESCRIPTION: SEQ ID NO: 51:

Gly Leu Thr His Glu Ala His Arg Lys Glu Val Glu Gln Val Tyr Leu
1               5                   10                  15
```

```
Arg Cys Ala Ala Gly Ala Val Glu Trp Met Tyr Pro Thr Gly Ala Leu
            20                  25                  30

Ile Val Asn Leu Arg Pro Asn Thr Phe Ser Pro Ala Arg His Leu Thr
        35                  40                  45

Val Cys Ile Arg Ser Phe Thr Asp Ser Ser Gly Ala Asn Ile Tyr Leu
    50                  55                  60

Glu Lys Thr Gly Glu Leu Arg Leu Leu Val Pro Asp Gly Asp Gly Arg
65                  70                  75                  80

Pro Gly Arg Val Gln Cys Phe Gly Leu Glu Gln Gly Gly Leu Phe Val
                85                  90                  95

Glu Ala Thr Pro Gln Gln Asp Ile Gly Arg Arg Thr Thr Gly Phe Gln
            100                 105                 110

Tyr Glu Leu Val Arg Arg His Arg Ala Ser Asp Leu His Glu Leu Ser
        115                 120                 125
```

(2) INFORMATION FOR SEQ ID NO: 52:

(i) SEQUENCE CHARACTERISTICS:
(A) LENGTH: 106 amino acids
(B) TYPE: amino acid
(C) STRANDEDNESS: single
(D) TOPOLOGY: linear (ii) MOLECULE TYPE: protein (iii) HYPOTHETICAL: NO (v) FRAGMENT TYPE: C-terminal (vi) ORIGINAL SOURCE:
(A) ORGANISM: Human
(F) TISSUE TYPE: Spleen tissue from healthy human (vii) IMMEDIATE SOURCE:
(B) CLONE: SEQ ID NO 5

(xi) SEQUENCE DESCRIPTION: SEQ ID NO: 52:

```
Ala Val Arg Gly Ser Ile Gln Gln Val Thr His Glu Pro Glu Arg Gln
1               5                   10                  15

Asp Ser Ala Ile His Leu Arg Val Ser Arg Leu Tyr Arg Gln Lys Ser
            20                  25                  30

Arg Val Phe Glu Pro Val Pro Glu Gly Asp Gly His Trp Gln Gly Arg
        35                  40                  45

Val Arg Thr Leu Leu Glu Cys Gly Val Arg Pro Gly His Gly Asp Phe
    50                  55                  60

Leu Phe Thr Gly His Met His Phe Gly Glu Ala Arg Leu Gly Cys Ala
65                  70                  75                  80

Pro Arg Phe Lys Asp Phe Gln Arg Met Tyr Arg Asp Ala Gln Glu Arg
                85                  90                  95

Gly Leu Asn Pro Cys Glu Val Gly Thr Asp
            100                 105
```

(2) INFORMATION FOR SEQ ID NO: 53:

(i) SEQUENCE CHARACTERISTICS:
(A) LENGTH: 29 amino acids
(B) TYPE: amino acid
(D) TOPOLOGY: linear (ii) MOLECULE TYPE: peptide (v) FRAGMENT TYPE: C-terminal (vi) ORIGINAL SOURCE:
(A) ORGANISM: Human -continued

```
        (H) CELL LINE: THP-1

       (xi) SEQUENCE DESCRIPTION: SEQ ID NO: 53:

Gly Cys Ala Pro Arg Phe Lys Asp Phe Gln Arg Met Tyr Arg Asp Ala
1               5                   10                  15

Gln Glu Arg Gly Leu Asn Pro Cys Glu Val Gly Thr Asp
            20                  25
```

POLYPEPTIDES AND PEPTIDES, NUCLEIC ACIDS CODING FOR THEM, AND THEIR USE IN THE FIELD OF TUMOR THERAPY, INFLAMMATION OR IMMUNOLOGY

The invention relates to polypeptides and peptides, particularly recombinant polypeptides, which can be useful in the field of tumor therapy, inflammation or immunology.

The invention also relates to a process for preparing the above-said polypeptides and peptides.

It also relates to nucleic acids coding for said polypeptides and peptides.

Monocytes/macrophages are cells of great complexity accomplishing a multitude of different functions related to (i) responses to environmental challenges such as phagocytosis, antigen processing and presentation, (ii) enzyme production, (iii) to differentiation, (iv) to regulatory responses by the synthesis of macrophage-specific cytokines which function as metabolic or immunological regulatory proteins and (v) by the production of complement components, coagulation factors, enzymes, enzyme inhibitors, and oxygen radicals (reviewed by Adams and Hamilton (1984).

Several macrophage-derived cytokines have already been described: interleukin-1 (IL-1), tumor necrosis factor (TNF), interleukin-6 (IL-6), colony stimulating factor (CSF), interferon (IFN), macrophage inflammatory protein (MIP), and monocytic-derived neutrophil chemotactic factor (MDNCF or IL-8) (Old, 1985; Durum et al., 1986; Quesenberry, 1986; Billiau, 1987; Yoshimura et al., 1987; Davatelis et al., 1988; Kishimoto and Hirano, 1988;). In most instances, the production of these cytokines by the macrophages requires exposure to one or more signals present in the immediate microenvironment of the cells. These signals may consist of particulate matter which can be opsonized, invading parasites, bacterial infectants, or antibody-covered antigens (Unanue, (1989)). They invariably lead to a state of enhanced competence of the macrophage (termed activation), ultimately giving rise to the synthesis of some of the above-mentioned macrophage-specific cytokines (monokines).

A particular set of genes (some of which are specifically expressed by macrophages, hereafter termed monokine genes) may correspond to each individual activation process. Such genes can either be up- or down-regulated. Characterization of some of these genes is possible by measuring their corresponding biological function with appropriate bioassays (Ruff and Gifford, 1986; Van Snick et al., 1986; Van Damme et al., 1987), or using differential hybridization with cDNAs derived from either activated or nonactivated macrophages. This can result in the isolation of cDNAs that correspond to genes switched on during the process of differentiation of resting macrophages to activated cells.

It is an object of the invention to provide new polypeptides and their corresponding nucleic acids which can be used in immunology or in the field of tumor therapy.

It is another object of the invention to provide nucleic acids coding for the peptide chains of biologically pure, active recombinant peptides which enable their preparation on a large scale.

It is another aspect of the invention to provide nucleic sequences which can be used as antisense oligonucleotides.

It is another aspect of the invention to provide a chromosomal DNA fragment which can be used for producing a pathological model of a nonhuman animal such as a trangenic animal which can be used to study the effects of pharmacological compositions and to prepare different cell types from these trangenic animals which express the gene of the invention in a constitutive or inducible way.

It is another aspect of the invention to provide "knock-out" trangenic animals (Capecchi, 1989) in which the natural gene effectively homologous to the nucleotide sequences of the invention (definition of effectively homologous given hereafter) is rendered nonfunctional, for instance, by homologous recombination, with said animal being suitable for the study of the possible loss of functions or the possible restoration effects caused by the reintroduction of the polypeptides of the invention into the animals.

The polypeptide of the invention is characterized by the fact that it contains in its peptidic chain:

the amino acid sequence of 311 amino acids of FIG. 3, or a fragment of this sequence, with said fragment being such that it is liable to produce antibodies capable of forming a complex with the amino acid sequence of FIG. 3, or an amino acid sequence having a percentage of homology of at least 50%, preferably 75%, and advantageously 90%, with the amino acid sequence of FIG. 3, or a sequence liable to form a complex with antibodies raised against the amino acid sequence of FIG. 3
or against pep1(m)
or against pep2(m)
or against pep3(m)

Pep1(m) has at least 8 contiguous amino acids contained in the following sequence:

Cys$^{52}$-Ser-Trp-Lys-Gly-Ser-Gly-Leu-Thr-Arg-Glu-Ala-Arg-Ser-Lys-Glu-Val-Glu-Gln-Val-Tyr-Leu-Arg-Cys, and preferably is the following sequence:

Arg-Glu-Ala-Arg-Ser-Lys-Glu-Val-Glu.

Pep2(m) has at least 8 contiguous amino acids contained in the following sequence:

Cys$^{107}$-Ile-Lys-Pro-Phe-Arg-Asp-Ser-Ser-Gly-Ala-Asn-Ile-Tyr-Leu-Glu-Lys-Thr-Gly-Glu-Leu-Arg-Leu-Leu-Val-Arg-Asp-Ile-Arg-Gly-Glu-Pro-Gln-Cys, and preferably is the following sequence:

Arg-Asp-Ile-Arg-Gly-Glu.

Pep3(m) has at least 8 contiguous amino acids contained in the following sequence:

Gly$^{283}$-Cys-Ala-Pro-Arg-Phe-Ser-Asp-Phe-Gln-Arg-Met-Tyr-Arg-Lys-Ala-Glu-Glu-Met-Gly-Ile-Asn-Pro-Cys-Glu-Ile-Asn-Met-Glu, and preferably is the following sequence:

Arg-Lys-Ala-Glu-Glu.

According to another advantageous embodiment of the invention, the peptide contains in its peptidic chain:

the amino acid sequence of 311 amino acids of FIG. 2, or a fragment of this sequence, with said fragment being such that it is liable to produce antibodies capable of forming a complex with the amino acid sequence of FIG. 2, or an amino acid sequence having a percentage of homology of at least 50%, preferably 75%, and advantageously 90%, with the amino acid sequence of FIG. 2, or a sequence liable to form a complex with antibodies raised:

against the amino acid sequence of FIG. 2
or against pep1(h)
or against pep2(h)
or against pep3(h).

Pep1(h) has at least 8 contiguous amino acids contained in the following sequence:

Cys$^{52}$-Ser-Trp-Lys-Gly-Ser-Gly-Leu-Thr-His-Glu-Ala-His-Arg-Lys-Glu-Val-Glu-Gln-Val-Tyr-Leu-Arg-Cys, and preferably is the following sequence:

Arg-Lys-Glu-Val-Glu.

Pep2(h) has at least 8 contiguous amino acids contained in the following sequence:

Cys[201]-Thr-Ser-Asp-Phe-Ala-Val-Arg-Gly-Ser-Ile-Gln-Gln-Val-Thr-His-Glu-Pro-Glu-Arg-Gln-Asp-Ser-Ala-Ile-His-Leu-Arg-Val-Ser-Arg, and preferably is the following sequence:

Glu-Pro-Glu-Arg-Gln-Asp.

Pep3(h) has at least 8 contiguous amino acids contained in the following sequence:

Gly[283]-Cys-Ala-Pro-Arg-Phe-Lys-Asp-Phe-Gln-Arg-Met-Tyr-Arg-Asp-Ala-Gln-Glu-Arg-Gly-Leu-Asn-Pro-Cys-Glu-Val-Gly-Thr-Asp, and preferably is the following sequence:

Arg-Asp-Ala-Gln-Glu-Arg.

An advantageous polypeptide of the invention is characterized by the fact that it is constituted by the sequence represented on FIG. 3, extending from the extremity constituted by amino acid at position (1) to the extremity constituted by amino acid at position (311) or that it contains at least one of the following peptides:

Cys-Ser-Trp-Lys-Gly-Ser-Gly-Leu-Thr

Val-Glu-Trp-Met-Tyr-Pro-Thr-Gly-Ala-Leu-Ile-Val-Asn-Leu-Arg-Pro-Asn-Thr-Phe-Ser-Pro-Ala

Asp-Ser-Ser-Gly-Ala-Asn-Ile-Tyr-Leu-Glu-Lys-Thr-Gly-Glu-Leu-Arg-Leu-Leu-Val

Leu-Glu-Gln-Gly-Gly-Leu-Phe-Val-Glu-Ala-Thr-Pro-Gln-Gln-Asp-Ile

Arg-Arg-Thr-Thr-Gly-Phe-Gln-Tyr-Glu-Leu

Leu-Ser-Ala-Pro-Cys-Arg-Pro-Cys-Ser-Asp-Thr-Glu-Val-Leu-Leu-Ala

Arg-Gln-Lys-Ser-Arg-Val-Phe

Cys-Gly-Val-Arg-Pro-Gly-His-Gly

Phe-Leu-Phe-Thr-Gly-His

Leu-Gly-Cys-Ala-Pro-Arg-Phe

Asp-Phe-Gln-Arg-Met-Tyr-Arg

An advantageous polypeptide of the invention is constituted by the sequence represented on FIG. 2, extending from the extremity constituted by amino acid at position (1) to the extremity constituted by amino acid at position (311).

The invention also relates to the muteins deriving from anyone of the above-defined polypeptides and containing modifications consisting of substitution, and/or deletion and/or addition of one or several amino acids, insofar that said modifications do not alter the hydropathicity profile as defined in Kyte and Doolittle (1982) and such as is represented in FIG. 6*a* and 6*b*.

The above-mentioned substitution is carried out by replacing one or more amino acids by their synonymous amino acids. Synonymous amino acids within a group are defined as amino acids which have sufficient physicochemical properties to allow substitution between members of a group in order to preserve the biological function of the molecule. Synonymous amino acids are those preferably listed in Table I.

| Amino acids | Synonymous groups |
|---|---|
| Ser | Ser, Thr, Gly, Asn |
| Arg | Arg, His, Lys, Glu, Gln |
| Leu | Leu, Ile, Met, Phe, Val, Tyr |
| Pro | Pro, Ala, Thr, Gly |
| Thr | Thr, Pro, Ser, Ala, Gly, His, Gln |
| Ala | Ala, Pro, Gly, Thr |

-continued

| Amino acids | Synonymous groups |
|---|---|
| Val | Val, Met, Ile, Tyr, Phe, Leu, Val |
| Gly | Gly, Ala, Thr, Pro, Ser |
| Ile | Ile, Met, Leu, Phe, Val, Ile, Tyr |
| Phe | Phe, Met, Tyr, Ile, Leu, Trp, Val |
| Tyr | Tyr, Phe, Trp, Met, Ile, Val, Leu |
| Cys | Cys, Ser, Thr |
| His | His, Gln, Arg, Lys, Glu, Thr |
| Gln | Gln, Glu, His, Lys, Asn, Thr, Arg |
| Asn | Asn, Asp, Ser, Gln |
| Lys | Lys, Arg, Glu, Gln, His |
| Asp | Asp, Asn, Glu |
| Glu | Glu, Gln, Asp, Lys, Asn, His, Arg |
| Met | Met, Ile, Leu, Phe, Val |

As to deletions or insertions of amino acids, they may also be introduced into the defined sequences provided they do not alter the biological functions of said sequences. Preferentially such insertions or deletions should be limited to a few amino acids and should not remove or physically disturb or displace amino acids which are critical to the functional conformation.

Muteins of the proteins of the invention are proteins having a sequence homologous to the sequence disclosed in the invention in which amino acid substitutions, deletions, or insertions are present at one or more amino acid positions. Said muteins may have a biological activity which is at least 10% of the polypeptides of the invention and which can be higher than the biological activity of the invention, and thus do not necessarily have to be identical to the biological function of the proteins of the disclosure.

In another embodiment of the invention, muteins derived from the protein sequences of the invention or polypeptides derived from said proteins may be used to block the biological function of the proteins of the invention. Preferably, such an embodiment is composed of polypeptides minimally containing about 7 amino acids and maximally having about 100 amino acids.

Another preferred embodiment contains polypeptides or muteins of the protein of the invention which comprise more than about 100 amino acids of a sequence contained in any one of the polypeptide sequences of the invention.

The proteins of the invention have interesting biological functions.

The term biological function means that the proteins, the muteins, and the polypeptides either provoke the proliferation of the target cell line, as can be measured by different methods such as the incorporation of $^3$H-thymidine, direct cell counting or 3-(4,5-dimethylthiazolyl-2)-2,5-diphenyltetrazolium bromide (MTT)-staining (Mossman, 1983), or provoke alterations in the differentiation state of the target cell line as can be measured by the changes in cell membrane marker distribution or the modulation of the biological activity of the target cell, or provoke mobilization or chemotaxis of the target cell line as can be measured by counting the cells migrating through microporous membranes.

According to another embodiment of the invention, the above-defined peptides have at least one of the following properties:

promoting the incorporation of $^3$H-thymidine in rat femur preosteoblast and osteoblast cells, in 3-week-old mice thymocytes, in splenic cells or lymph node cells advantageously upon costimulation with IFN-γ, promoting the incorporation of $^3$H-thymidine in thymocytes, advantageously upon costimulation with IL-4, promoting the activation, cytotoxicity or mobility of LAK cells, promoting the recruitment of suppressive peritoneal exudate cells upon injection in vivo, promoting the generation of immunocompetent lymph node cells, preferentially after ConA, PHA or LPS induction, upon in vivo intrafootpath injection, exerting a trypanocidal or trypanolytical activity on the pleomorph bloodstream trypanosomes in vitro.

Promoting the incorporation of $^3$H-thymidine in rat femur osteoblast cells corresponds to an increased proliferation of the cells and can be carried out according to the technique as described in the examples.

Promoting the incorporation of $^3$H-thymidine in 3-week-old thymocytes, advantageously upon costimulation with IL-4, corresponds to an enhanced cell proliferation and can be carried out as described in the examples.

Promoting the incorporation of $^3$H-thymidine in splenic cells or lymph node cells, advantageously upon costimulation with IFN-γ, corresponds to an enhanced cell proliferation and can be carried out as described in the examples. Promoting the mobility of LAK cells can be carried out as described in the examples. Promoting the recruitment of supressive peritoneal exudate cells, promoting the generation of immunocompetent lymph node cells, and exerting a trypanocidal activity can be measured as described in the examples.

As to the activity or cytotoxicty of LAK cells, the activity of the polypeptides of the invention can be shown by the use of anti-sense primers derived from the nucleotides of the invention which are capable of reducing or blocking the activation or cytotoxicity of LAK cells, or the IL-2-generated expression of the polypeptides of the invention.

It should be clear that the addition of IL-2 in order to promote the activation or the cytotoxicity of LAK cells is accompanied by the induction of the mRNA of the polypeptides of the invention.

The protein of the invention induces the uptake of $^3$H-thymidine upon its addition to thymocytes in the presence of a lectin (PHA or ConA or others), with such uptake being enhanced by coincubation with cytokines (IL-4, IL-2, IL-1, IL-6 or combinations of these). In another preferred embodiment, the composition of the invention induces the uptake of $^3$H-thymidine when added to splenic cells and lymph node cell populations in the presence of a lectin, with such uptake being enhanced by coincubation with IFN-γ. In another preferred embodiment, the composition of the invention induces the differentiation of splenic cells into LAK cells when added together with IL-2.

It is to be noted that the above-mentioned polypeptides are derived from the expression products from the nucleotide sequence coding for a protein of 30 or 34 kDa present in the culture fluids of human and mouse macrophages, respectively, in the human monocytic cell lines U-937 (ATCC 1593), and in the cell line Mono Mac 6 (Ziegler-Heitbrock) or in the mouse cell line PU5-1.8. (ATCC TIB61).

The invention also relates to the purified natural mammalian proteins, muteins thereof, and polypeptides derived from them. "Purified" corresponds to the proteins obtained according to the process as specified in the examples.

The invention also relates to the amino acid sequences constituted by the above-mentioned polypeptides and a protein or a heterologous sequence with respect to said polypeptide, with said protein or heterologous sequence comprising, for instance, anywhere from about 10 to about 100 amino acids.

The invention also relates to the nucleic acid sequences containing or constituted by:

a nucleotide sequence which is effectively homologous with the nucleotide sequences coding for the above-defined polypeptides, a nucleotide sequence liable to hybridize with anyone of the nucleotide sequence coding for the above-defined polypeptides, or a nucleotide sequence which, further to translation or further to transcription and to translation, leads to anyone of the above-defined polypeptides, or the complementary sequences of the above-mentioned nucleotide sequences.

An "effectively homologous" nucleotide sequence derived from the sequence of the invention is at least fifty percent homologous to the sequence to be isolated. More preferably, the effectively homologous nucleotide sequence is at least seventy-five percent homologous to the sequence to be isolated. Most preferably, the effectively homologous nucleotide sequence is at least ninety percent homologous to the sequence to be isolated. Homology, as used herein, is a measure of similarity between nucleotides or amino acids and can be expressed as the fraction of nucleotides or amino acids in the nucleotide sequence that are identical to the sequence to be isolated.

An advantageous nucleic acid of the invention comprises or is constituted by:

a nucleotide sequence which is effectively homologous with the nucleotide sequence of FIG. 1, a nucleotide sequence liable to hybridize with the complementary strand of the nucleotide sequence of FIG. 1, the nucleotide sequence of FIG. 1, the complementary sequences of the above-mentioned sequences the above-mentioned sequences wherein T is replaced by U.

Another advantageous nucleic acid of the invention comprises or is constituted by:

a nucleotide sequence which is effectively homologous with the nucleotide sequence of FIG. 2, a nucleotide sequence liable to hybridize with the complementary strand of the nucleotide sequence of FIG. 2, the nucleotide sequence of FIG. 2, the complementary sequences of the above-mentioned sequences, the above-mentioned sequences wherein T is replaced by U.

Another advantageous nucleic acid of the invention comprises or is constituted by:

a nucleotide sequence which is effectively homologous with the nucleotide sequence of FIG. 3, a nucleotide sequence liable to hybridize with the complementary strand of the nucleotide sequences of FIG. 3, the nucleotide sequence of FIG. 3, the complementary sequences of the above-mentioned sequences, the above-mentioned sequences wherein T is replaced by U.

Appropriate hybridization conditions between human cDNA and mouse cDNA are the following ones:

hybridization temperature: 42° C., hybridization medium: 47% deionized formamide, 10% dextrane sulfate, 3×SSPE (3.6M NaCl, 0.2M $NaH_2PO_4$, 0.02M EDTA, pH 7.4), 1% SDS, 0.5% milk powder, wash temperature: 50° C.

wash medium: 1×SSC, 0.1% SDS.

The invention also relates to a recombinant nucleic acid containing at least one of the above-mentioned nucleic acids combined with or inserted in a heterologous nucleic acid.

The invention also relates to a recombinant vector particularly for cloning and/or expression, comprising a vector sequence, notably of the type plasmid, cosmid, phage, or virus DNA and a recombinant nucleic acid as mentioned above, inserted in one of the nonessential sites for its replication.

The invention also relates to a recombinant vector as defined above and containing necessary elements to promote the expression in a cellular host of polypeptides coded by nucleic acids of the invention, inserted in said vector and notably a promoter recognized by the RNA polymerase of the cellular host, particularly an inducible promoter, and possibly a sequence coding for transcription, termination and possibly a signal sequence and/or an anchoring sequence.

The invention also relates to a recombinant vector as defined above, containing the elements enabling the expression of a nucleotide sequence coding for the polypeptide of the invention as a mature protein or as part of a fusion protein; the fusion moiety which is used in the fusion protein is a part of a nonhomologous protein (such as mTNF) chosen to optimize the expression of the fusion protein.

The sequence of mTNF in pmTNF is described in FIG. 8*a* and 8*b*.

The invention also relates to a cellular host chosen from among bacteria such as *E. coli* or chosen from among eukaryotic organisms, such as COS1 cells, which is transformed by a recombinant vector defined above and containing the regulatary elements enabling the expression of the nucleotide sequence coding for the polypeptide of the invention in this host.

The invention also relates to viral vectors such as vaccinia virus or baculovirus, in which a recombinant nucleic acid is inserted in a nonessential site for virus replication, with said viral vectors being capable of infecting various eukaryotic cells or cell lines, resulting in the production of biologically active recombinant polypeptides of invention.

The invention also relates to an expression product of a nucleic acid expressed by a transformed cellular host as defined above.

The invention also relates to antibodies themselves formed against the polypeptides according to the invention.

It goes without saying that this production is not limited to polyclonal antibodies.

It also relates to any monoclonal antibody produced by any hybridoma liable to be formed according to classical methods from animal splenic cells, particularly from a mouse or rat, the cells of the animal being immunized against the purified polypeptide of the invention on the one hand, and of cells from a myeloma cell line on the other, and to be selected by the ability of the cell line to produce the monoclonal antibodies recognizing the polypeptide which has been initially used for the immunization of the animals.

The invention also relates to any antibody of the invention labeled by an appropriate label of the enzymatic, fluorescent, or radioactive type.

The peptides which are advantageously used to produce antibodies, particularly monoclonal antibodies, are the following:

$Cys^{52}$-Ser-Trp-Lys-Gly-Ser-Gly-Leu-Thr-Arg-Glu-Ala-Arg-Ser-Lys-Glu-Val-Glu-Gln-Val-Tyr-Leu-Arg-Cys,

Arg-Glu-Ala-Arg-Ser-Lys-Glu-Val-Glu, $Cys^{107}$-Ile-Lys-Pro-Phe-Arg-Asp-Ser-Ser-Gly-Ala-Asn-Ile-Tyr-Leu-Glu-Lys-Thr-Gly-Glu-Leu-Arg-Leu-Leu-Val-Arg-Asp-Ile-Arg-Gly-Glu-Pro-Gly-Gln-Val-Gln-Cys,

Arg-Asp-Ile-Arg-Gly-Glu, $Gly^{283}$-Cys-Ala-Pro-Arg-Phe-Ser-Asp-Phe-Gln-Arg-Met-Tyr-Arg-Lys-Ala-Glu-Glu-Met-Gly-Ile-Asn-Pro-Cys-Glu-Ile-Asn-Met-Glu,

Arg-Lys-Ala-Glu-Glu, $Cys^{52}$-Ser-Trp-Lys-Gly-Ser-Gly-Leu-Thr-His-Glu-Ala-His-Arg-Lys-Glu-Val-Glu-Gln-Val-Tyr-Leu-Arg-Cys,

Arg-Lys-Glu-Val-Glu, $Cys^{201}$-Thr-Ser-Asp-Phe-Ala-Val-Arg-Gly-Ser-Ile-Gln-Gln-Val-Thr-His-Glu-Pro-Glu-Arg-Gln-Asp-Ser-Ala-Ile-His-Leu-Arg-Val-Ser-Arg,

Glu-Pro-Glu-Arg-Gln-Asp, $Gly^{283}$-Cys-Ala-Pro-Arg-Phe-Lys-Asp-Phe-Gln-Arg-Met-Tyr-Arg-Asp-Ala-Gln-Glu-Arg-Gly-Leu-Asn-Pro-Cys-Glu-Val-Gly-Thr-Asp

Arg-Asp-Ala-Gln-Glu-Arg

From the nucleic acids of the invention, probes (i.e. cloned or synthetic oligonucleotides) can be inferred.

These probes can be from 15 to the maximum number of nucleotides of the selected nucleic acids. The oligonucleotides can also be used either as amplification primers in the PCR technique (Mullis and Faloona, 1987) to generate specific enzymatically amplified fragments and/or as probes to detect fragments amplified between bracketing oligonucleotide primers.

The specificity of a PCR-assisted hybridization assay can be controlled at different levels.

The amplification process or the detection process or both can be specific. The latter case, giving the higher specificity, is preferred. Examples of primers are the following:

```
For mouse:

                      629                 649
                       |                   |
1)sense primer:       5'-AGGGAGGCTTATTTGTGGAGG-3'

                      1195                1174
                       |                   |
antisense primer:     5'-GGATATGATAGAGCGACTGAGC-3'

denaturation T:       95° C.
annealing T:          56° C.
elongation T:         72° C.

                      366                 386
                       |                   |
2)sense primer:       5'-CCGAGAGGCACGCAGCAAGGA-3'

                      753                  732
                       |                    |
antisense primer:     5'-CCGACAGGGGGCAGACAGCACG-3'

denaturation T:       95° C.
annealing T:          60° C.
elongation T:         72° C.

For man:

                      98                  118
                       |                   |
1)sense primer:       5'-GCTGCTCCTGCTCCTGGCCGG-3'

                      546               526
                       |                  |
```

-continued

```
antisense primer:    5'-GGTCCGACGCCCTGTGCCTC-3'

denaturation T:      95° C.
annealing T:         64° C.
elongation T:        72° C.

                      247                265
                       |                  |
2)sense primer:      5'-AGTGGATGTACCCAACAGG-3'

                     398                      378
                      |                        |
antisense primer:    5'-TACCAGCAGTCTCAGTTCTCC-3'

denaturation T:      95° C.
annealing T:         50° C.
elongation T:        72° C.
```

The invention also relates to a process for preparing a polypeptide according to the invention comprising the following steps:

the culture in an appropriate medium of a cellular host which has previously been transformed by an appropriate vector containing a nucleic acid according to the invention, the recovery of the polypetide produced by the above-said transformed cellular host from the above-said culture, and the purification of the polypeptide produced.

In case of a fusion protein in which the fusion moiety is, for instance, part of mTNF, purification can be achieved by immunoaffinity chromatography.

If the fusion protein contains in addition to the fusion moiety a stretch of at least 2 histidines, purification can be achieved by immobilized metal affinity chromatography (IMAC) as detailed in the examples.

In a particular case, the fusion protein is composed of a polypeptide which, in the host (eukaryotic or prokaryotic) used for the expression of the protein, acts as a natural signal sequence for the expression of the polypeptides of the invention in the culture medium. In a particular embodiment, this signal sequence can be the naturally occurring signal sequence as present in the cDNA sequences of the invention. Purification can be achieved by applying a $Mg^{++}$/dextrane sulphate precipitation followed by sequential liquid chromatography steps, including hydrophobic interaction chromatography such as phenyl sepharose fast flow chromatography (Pharmacia), ion exchange chromatography such as Mono-Q Sepharose (Pharmacia), glycoprotein binding matrices such as Phenylboronate agarose (Amicon) and gelfiltration such as Superdex 75 (Pharmacia) or TSK100 (Merck).

Purification of the natural protein or muteins thereof can be achieved by using sequential liquid chromatography steps as detailed above.

The polypeptides of the invention can be prepared according to the classical techniques in the field of peptide synthesis.

The synthesis can be carried out in homogeneous solution or in solid phase.

For instance, the synthesis technique in homogeneous solution which can be used is the one described by Houbenweyl (1974).

The polypeptides of the invention can also be prepared in solid phase according to the methods described by Atherton and Sheppard (1989).

The invention also relates to a process for preparing the nucleic acids according to the invention.

A suitable method for chemically preparing the single-stranded nucleic acids (containing at most 100 nucleotides of the invention) comprises the following steps:

DNA synthesis using the automatic β-cyanoethyl phosphoramidite method described in Bioorganic Chemistry 4; 274–325 (1986).

In the case of single-stranded DNA, the material which is obtained at the end of the DNA synthesis can be used as such.

A suitable method for chemically preparing the double-stranded nucleic acids (containing at most 100 bp of the invention) comprises the following steps:

DNA synthesis of one sense oligonucleotide using the automatic β-cyanoethyl phosphoramidite method described in Bioorganic Chemistry 4; 274–325 (1986), and DNA synthesis of one antisense oligonucleotide using either the above mentioned automatic β-cyanoethyl phosphoramidite method, or enzymatic transcription of the sense-strand using a specific primer hybridizing to the 3'-end of the sense strand, combining the sense and antisense oligonucleotide by hybridization in order to form a DNA duplex, cloning the DNA duplex obtained into a suitable plasmid vector and recovery of the DNA according to classical methods such as restriction enzyme digestion and agarose electrophoresis, or by PCR amplification according to the procedure outlined above.

A method for the chemical preparation of nucleic acids with lengths greater than 100 nucleotides - or base pairs, in the case of double-stranded nucleic acids comprises the following steps:

assembling the synthesized oligonucleotides, provided at their ends with different restriction sites, the sequences of which are compatible with the succession of amino acids in the natural peptide, according to the principle described Urdea et al., (1983), cloning the DNA thereby obtained into a suitable plasmid vector and recovery of the desired nucleic acid according to classical methods such as restriction enzyme digestion and agarose gel electrophoresis.

The purified natural mammalian proteins are preferentially extracted from the culture fluid of human and mouse macrophages and from the culture fluid from human monocytic cells and cell lines such as U937 (ATCC 1593) and Mono Mac 6 (Ziegler-Heitbrock) and from mouse monocytic cell lines such as PU5-1.8. (ATCC TIB61).

As derived from said culture fluids, the human protein has a mobility on SDS-polyacrylamide gels corresponding to a molecular weight of 30 kDa under reduced conditions and of 27 kDa under nonreduced conditions; the mouse protein has a molecular weight of 34 kDa under reduced conditions and of 30 kDa under nonreduced conditions, and may be present as proteins carrying post-translational secondary modification such as glycosylation, phosphorylation (but not limited to these).

The invention also relates to the process of purification of the natural proteins, the recombinant proteins, the muteins thereof and polypeptides derived from them as specified in the examples.

Said compositions can be used for the treatment of mammalian cells in vitro as shown in the examples.

The mRNA derived from the cDNAs of the invention can be found in several mammalian cell lins including, but not limited to:

PU5-1.8 (ATCC TIB61), L-929 (ATCC CCL1), NIH 3T3 (ATCC CRL 1658), U-937 (ATCC 1593), Mono Mac 6 (Ziegler-Heitbrock, see above) or CTLL (ATCC TIB 214).

The said MRNA can also be found in mammalian cell lines after application of external stimuli including, but not limited to: lipopolysaccharide (LPS), phorbol 12-myristate 13-acetate diester ($C_{36}H_{56}O_8$)(PMA), retinoic acid ($C_{20}H_{28}O_2$)(RA) and IL-2. Preferentially, said mRNA can be detected by Northern blotting (Fourney et al., 1988) or by the polymerase chain reaction (Saiki et al., 1985) in Mono Mac 6 cells either stimulated or nonstimulated by LPS and in mouse natural killer (NK) cells derived from mouse spleen after treatment with IL-2 as specified in the examples.

The invention also relates to an antibody characterized as being specifically directed against a polypeptide according to the invention.

The invention also relates to polypeptides containing epitopes which can be used to raise monoclonal or polyclonal antibodies. Said polypeptides are composed of a string of amino acids having a sequence homologous to or synonymous with the disclosed sequence. Preferentially, said epitopes contain minimally 8 amino acids. A preferred embodiment of the invention contains the sequence (hu clone 5 peptide I, peptide II, or peptide III). It should be understood that said epitope-containing polypeptides can be used to generate antibodies capable of interfering with the blocking of the biological function of the proteins, the muteins thereof, and the polypeptides derived from them. The polypeptides may be used themselves or in combination with the antibodies in the diagnosis of the polypeptides or the antibodies. Either or both may be labelled or unlabelled for use in diagnostic assays. A large number of such assays are described in the literature and include the binding, either directly or indirectly, of these polypeptides or antibodies to a variety of labels including, but not limited to, enzymes, radionucleides, fluorescers, chemiluminescers, coenzymes, particles, or the like. The antibodies to these polypeptides (AB1) may be used themselves as antigens to produce antiidiotypes (AB2) which may serve as competitive antigens having epitopic sites competitive with the epitopic sites of these polypeptides. These anti-idiotypes AB2 may therefore be used as substitutes for the polypeptides or as antagonists to these polypeptides. These AB2 anti-idiotypes may themselves be used as antigens to produce anti-anti-idiotypes (AB3) to these polypeptides which may serve as substitutes for AB1, having complementarity-determining regions competitive with the complementarity-determining regions of AB1.

The invention also relates to the use of the proteins of the invention, muteins thereof or peptides derived from them for the selection of recombinant antibodies by the process of repertoire cloning (Perrson et al., 1991).

The invention relates to nucleotidic probes, hybridizing with any of the above-defined nucleic acid sequences.

Preferred oligonucleotide probes of the cDNAs of the invention are the following:

Human probes:

probe 1: 5'-TTCACGGACTCCTCGGGGGCCAATA-3' probe 2: 5'-TGGCCTGGAGCAGGGCGGCCTGTTC-3' probe 3: 5'-ACAGGCTTCCAGTACGAGCTGGTTA-3'

Mouse probes:

probe 1: 5'-GGGCTCACCCGAGAGGCACGCAGCA-3' probe 2: 5'-ATCAAGCCTTTCAGGGACTCCTCTG-3' probe 3: 5'-AACAGGCTTCACAGGCAGAAGAGCA-3'

By way of example and not intended to be limiting, a typical protocol for the hybridization of these nucleotidic probes with any of the above-defined nucleic sequences bound to a solid support (e.g. a nitrocellulose membrane) is described below.

The membranes were prehybridized in a mixture containing the following components: 3×SSC (1×SSC is 0.15M NaCl plus 0.015M sodium citrate, pH 7.0), 25 mM sodium phosphate buffer (pH 7.1), 20% (v/v) deionized formamide, 0.02% Ficoll (type 400, Sigma), 0.02% bovine serum albumin, 0.02% polyvinylpyrrolidone, 0.1 mg sheared heat-denatured salmon sperm DNA $ml^{-1}$, and 0.2% SDS, usually for 0.5–1 h at the appropriate temperature. The hybridization mixture had the same composition except that approximately $10^6$ c.p.m. of $^{32}P$-labelled probe $ml^{-1}$ was added. Hybridizations were performed at the same temperature for 1–2 h. The membranes were washed for 30 min in 3×SSC, 25 mM sodium phosphate buffer (pH 7.1), 20% (v/v) deionized formamide, 0.2% SDS at the hybridization temperature.

The optimal hybridization and wash temperatures are:

human probe 1: 57° C.

human probe 2: 62° C.

human probe 3: 54° C.

mouse probe 1: 62° C.

mouse probe 2: 54° C.

mouse probe 3: 54° C.

The invention relates to a process for detecting the capacity of a molecule to behave as a ligand or as a receptor with respect to a polypeptide of the invention, characterized by:

contacting the molecule with a cellular host which has previously been transformed by a vector itself modified by an insert coding for said polypeptide, this host carrying on its surface one or several specific sites of this polypeptide, possibly after induction of the expression of this insert, with said contacting being carried out under conditions enabling a binding to occur between at least one of these specific sites and said molecule if it happens to present an affmity for said polypeptide, detecting the possible formation of a complex of the type ligand-polypeptide or receptor-polypeptide.

The invention also relates to immunogenic compositions containing, as active substance, at least one of the polypeptides of FIG. 2, or anyone of the peptides pep1(h), pep2(h), or pep3(h).

The invention also relates to pharmaceutical compositions containing, as active substance, at least one of the polypeptides of the invention or of the antagonists of the polypeptides of the invention as antitumor compounds, as anti-inflammatory compounds, as growth activators of T-cells or B-cells, as bone repair compounds as inducer of immunosupressive cells, as inhibitors of anti-colony stimulating factor, or as trypanocidal agents; or part of the polypeptides of the invention, capable of binding to the above-defined receptor.

Said compositions can be used for the treatment of mammalian cells in vitro as detailed in the examples.

More particularly, the polypeptides of the invention and the AB1, AB2 and AB3 antibodies will find utility in various ways either as diagnostic reagents or as therapeutic agents, especially in the field of tumor therapy, macrophage activation and deactivation, T-cell ontogenicity, osteoblast proliferation and proliferation inhibition, LAK cell mobilization, generation and cytotoxicity, T- and B-cell growth and anti-colony stimulating activity, immuno-supressive activity and trypanocidal activity.

The invention also relates to the process in which the proteins of the invention, their muteins, or polypeptides derived from them are used for the isolation and characterization of cellular receptors or binding molecules which are capable of forming a complex with said compound. As stated herein, a receptor is characterized by its localization on the cell membrane, its ability to bind to the compounds of the invention, and its ability to produce signal transduction upon binding, thereby leading to an altered state of the cell on which said receptor is present. Binding molecules as referred to herein are those molecules which are capable of interacting with the compounds of the invention in such a way that this interaction is stable under physiological circumstances. Preferentially such molecules are capable of forming said complexes between temperatures of 0° C. and 45° C., between pH 2 or 11 or at ionic strengths not higher than those of a 2M NaCl solution.

In case AB1 antibodies are capable of neutralizing the biological functions of the composition of the invention, the AB3 antibodies may contain the internal image of the naturally occurring receptors for the composition of the invention. AB3 antibodies may therefore be used in diagnostic assays for the measurement of receptor amounts and as antagonist to these receptors. For the same reason AB2 antibodies can be used as an agonist of these receptors.

The invention also relates to antisense oligonucleotides or antisense mRNA derived from the nucleotide sequences of the invention.

Such antisense oligonucleotides may be introduced into cells and cell lines expressing the nucleotide sequence of the invention by methods known to those skilled in the art. Antisense mRNA of which the sequence can be deduced from the sequences of the invention can also be expressed in cells and cell lines by methods known to those skilled in the art. In doing so, these antisense oligonucleotides or antisense mRNA may interfere with the translation of the sequence of the invention thereby effectively blocking the biological role of these expressed mRNAs. Preferably these anti-sense oligonucleotides can be introduced into cells or cell lines according to methods known by the man skilled in the art such as those found in Wickstrom et al. (1988).

Said antisense oligonucleotides contain preferentially a sequence of 8 or more nucleotides having sequences effectively homologous to the sequence of the disclosure. In a preferred embodiment, an antisense oligonucleotide of the sequence (5'-CACCGCACCCCGCAT-3' reverse complement of the 5' to 3' mouse sequence from position 187 to 201) is used.

These antisense oligonucleotides can also be introduced into cells or cell lines by transfection of a plasmid in which the gene encoding the protein is in the opposite orientation with respect to the promoter (Izant and Weintraub (1984, 1985).

The invention also relates to nonhuman mammalian trangenic animals which contain, in their genomes, a nucleic acid sequence of the invention, and which can be used to study the effects of pharmacological compositions and to prepare different cell types from these trangenic animals which express the gene of the invention in a constitutive or inducible way.

More particularly, a trangenic nonhuman animal can be prepared according to the protocol described by Gordon (1989).

Trangenic animals can be prepared by transformation of suitably adapted polynucleotide sequences derived from the invention in embryonic stem cells. In a preferred embodiment, the embryonic stem cells belong to the mouse embryonic stem cell line ES (Wagner et al., 1985).

Said sequences can also be introduced by direct injection into fertilized oocytes. The methods for adaptation of said nucleotides sequences to make them capable of transformation or for injection are known by those skilled in the art (Gordon, 1989).

A variant trangenic animal is a "knock-out" animal prepared according to Capecchi (1989).

More particularly, "knock-out" nonhuman mammalian trangenic animals are such that the natural gene (effectively homogenous with the nucleotide sequences of the invention) is rendered nonfunctional, for instance by homologous recombination, with said animal being suitable for the study of the possible loss of functions or the possible restoration effects caused by the reintroduction into the animals of the polypeptides of the invention.

DESCRIPTION OF THE FIGURES

FIG. 1, FIG. 1 (con't 1), FIG. 1 (con't 2), and FIG. 1 (con't 3) represents the human genomic sequence of the cDNA of the invention.

Its characteristics are the following:

SEQUENCE TYPE: nucleotide with corresponding protein

SEQUENCE LENGTH: 3741 base pairs

STRANDNESS: single

TOPOLOGY: linear

ORIGINAL SOURCE: human

IMMEDIATE EXPERIMENTAL SOURCE: spleen tissue from healthy adult

FEATURES: from 1980 to 2188 bp intron 1 (only partially sequenced: estimated length ±5400 bp)

from 2575 to 2766 bp intron 2 (only partially sequenced: estimated length ±7900 bp)

from 2827 to 2875 bp intron 3 (only partially sequenced: estimated length ±1000 bp)

S: G or C

M: A or C

R: A or C

K: T or G

Y: T or C (X): either present or absent.

FIG. 2, FIG. 2(con't 1), and FIG. 2 (con't 2) represents the nucleotide sequence of the human cDNA homologous to the mouse cDNA sequence of the invention. Its characteristics are the following:

SEQUENCE TYPE: nucleotide sequence with corresponding protein

SEQUENCE LENGTH: 1487 base pairs

STRANDNESS: single

TOPOLOGY: linear

MOLECULE TYPE: copy DNA

ORIGINAL SOURCE

ORGANISM: human

IMMEDIATE EXPERIMENTAL SOURCE

NAME OF THE CELL LINE: THP-1

FEATURES:

from 1 to 5 bp: 5' non-coding region from 6 to 140 bp: signal sequence as predicted by Von Hejine G. Nucl. Acids Res. (1986) 14:4683.

from 141 to 938 bp: mature peptide from 939 to 1487 bp: 3'non-coding region.

FIG. 3 and FIG. 3 (con't 1) represents the nucleotide sequence of the mouse cDNA of the invention. Its characteristics are the following:

SEQUENCE TYPE: nucleotide with corresponding protein

SEQUENCE LENGTH: 1362
STRANDNESS: single
TOPOLOGY: linear
MOLECULE TYPE: copy DNA
ORIGINAL SOURCE
ORGANISM: mouse
IMMEDIATE EXPERIMENTAL SOURCE
NAME OF CELL LINE: PU5-1.8.
FEATURES:

from 1 to 186 bp: 5' non-coding region from 187 to 321 bp: signal sequence as predicted by Von Heijne G. NAR (1986) 14:4683.

from 322 to 1119 bp: mature peptide from 1120 to 1362 bp: 3' non-coding region.

Figure 4:
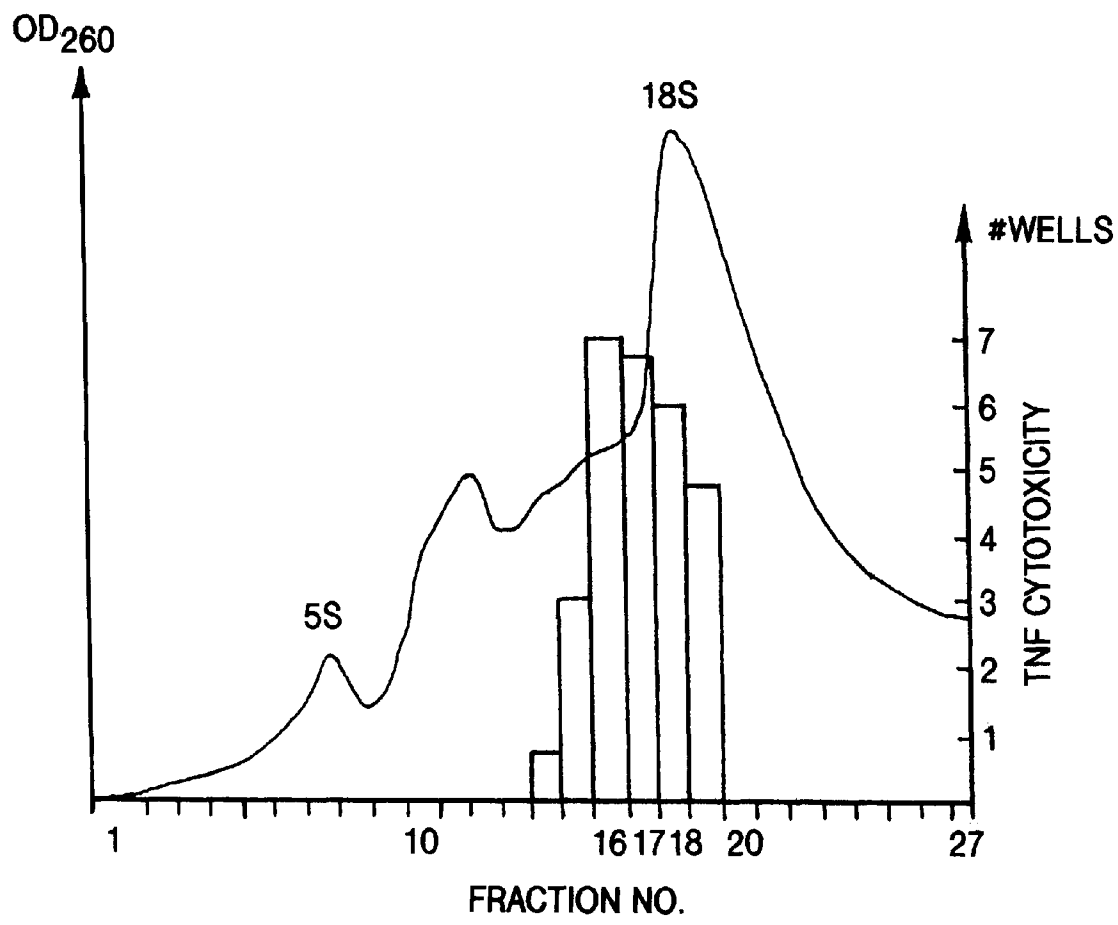

FIG. 4 represents the sucrose gradient fractionation of LPS-induced PU5-1.8. cells. MRNA of PU5-1.8. cells which is prepared using the Nonidet-P40 lysis method followed by a poly-$A^+$purification over oligo-dT as described in section 1.2. 400 $\mu$g of poly-$A^+$-RNA were further fractionated on a 5–20% sucrose gradient prepared in 10 mM Tris-HCl, pH 7.5, 1 mM EDTA. Gradients were run in a SW40 rotor for 19 hours at 40,000 rpm in a Beckman ultracentrifuge at 4° C. After centrifugation, 0.4 ml fractions were collected and each fraction was assayed for the presence of mTNF mRNA by injection of 50 nl of each fraction in 15 oocytes of Xenopus laevis in 200 $\mu$l of incubation medium. After 24 hours, the oocyte incubation medium was assayed for the presence of biologically active mTNF by incubating 100 $\mu$l with 4–5×$10^4$ L-929 cells in the presence of 1 $\mu$g/ml of actinomycin D essentially as described by Ruff and Gifford (1983). The fractions 16, 17 and 18, containing the maximal TNF activity and containing the 17S mRNA population were pooled and used for the preparation of the 17S LPS-induced PU5-1.8. cDNA library.

The x-axis corresponds to the numbers of fractions, the left y-axis corresponds to the optical density of 260 nm and the right y-axis corresponds to the TNF toxicity.

FIG. 5, FIG.5 (con't 1) and FIG.5 (con't 2) represents the alignment of the human and mouse amino acid sequence encoded by the open reading frame from nucleotide position 6 to 938 on the human and position 187 to 1061 on the mouse cDNA sequence presented in FIG. 2 and 3, respectively. Both sequences share 77.4% homology. The ten CYS residues conserved between human and mouse are boxed as well as the computer-predicted antigenic peptides. The synthetic oligopeptides used to raise antibodies are underlined.

Figure 6A:
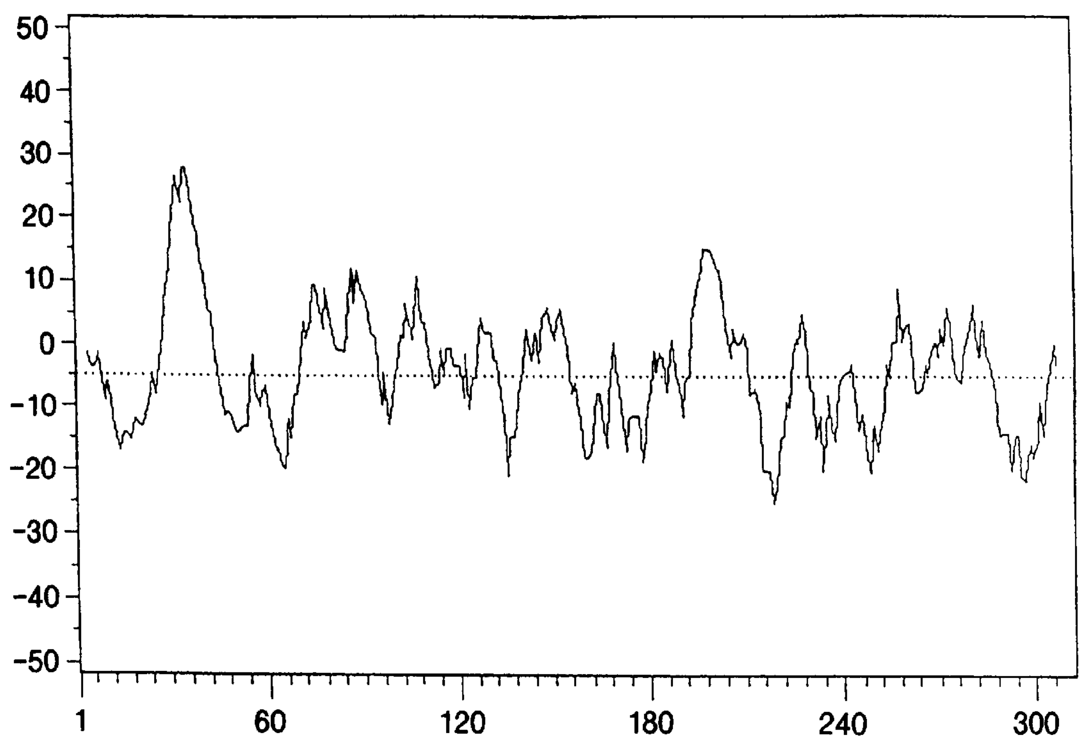
Figure 6B:
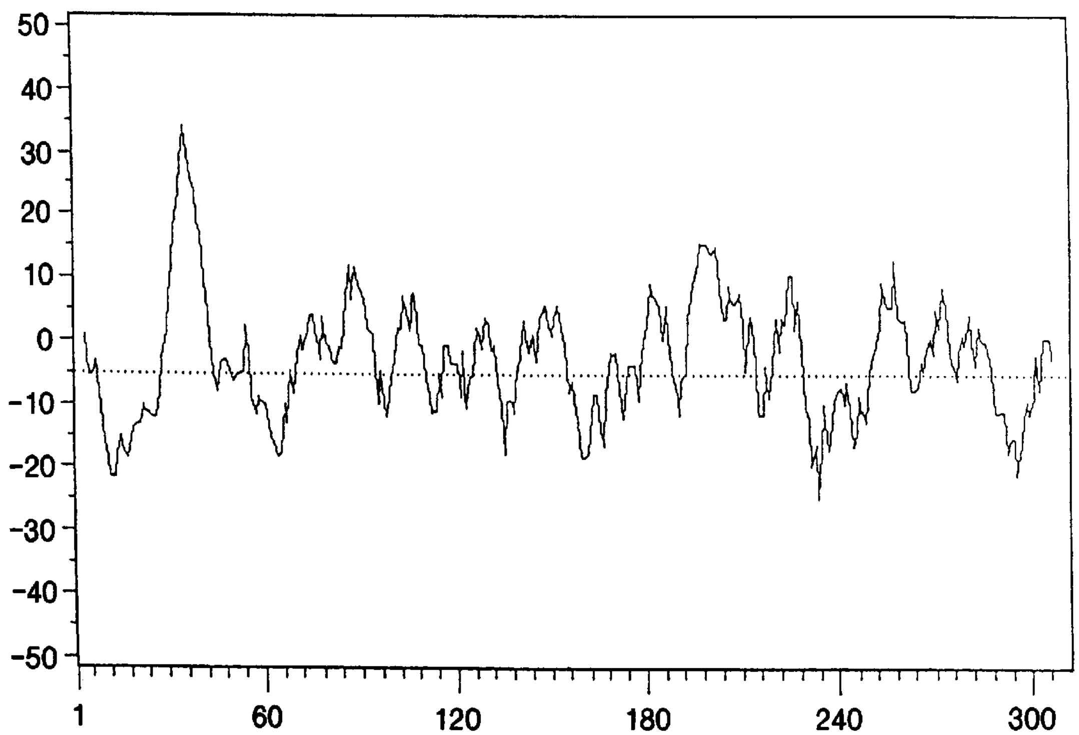

FIG. 6*a* and FIG. 6*b* represent the respective hydropathicity profile of the human and mouse amino acid sequences of the invention as depicted in FIG. 2 and 3.

Figure 7:
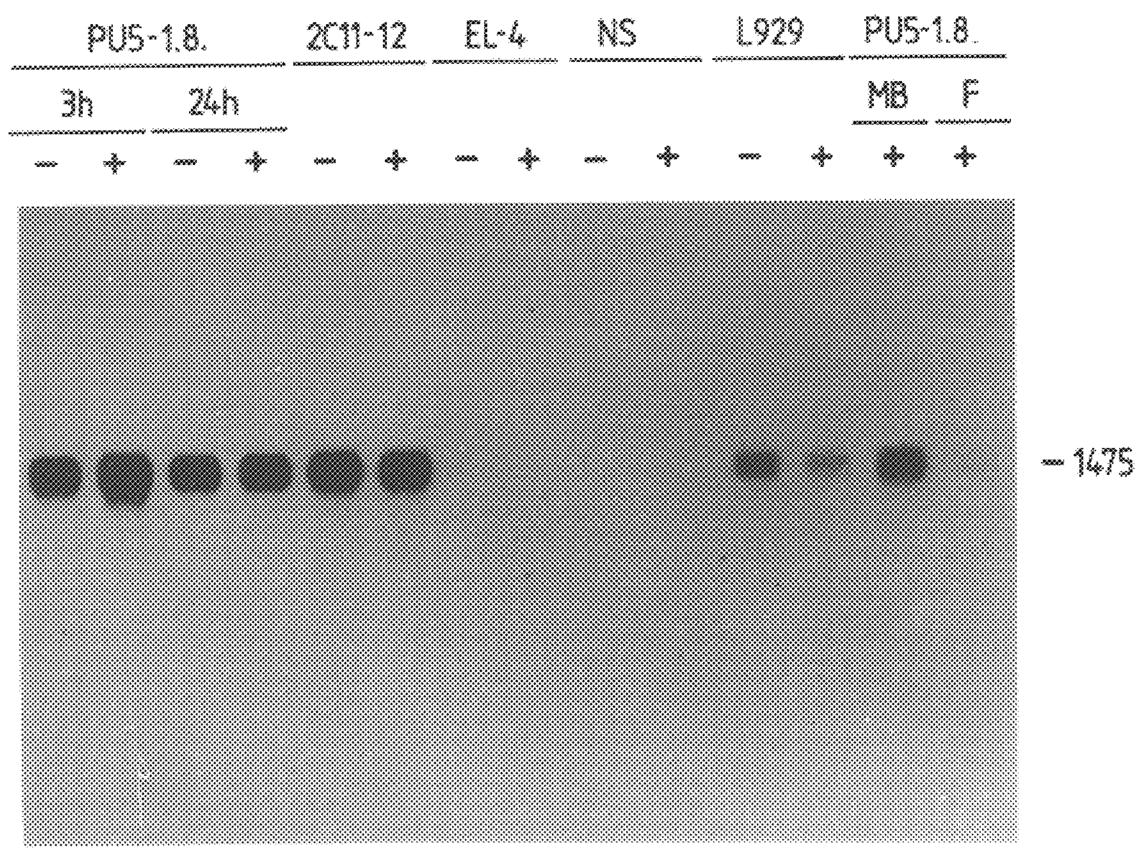

FIG. 7 represents the Northern blot analysis of MRNA of different uninduced and LPS-induced cell lines to determine the degree of macrophage specificity and LPS inducibility of the selected LPS-induced cDNA clone of mouse PU5-1.8 cells. Poly-$A^+$RNA of the different cell lines here analyzed was prepared using the Nonidet-P40 lysis method followed by purification by column chromatography over oligo-dT essentially as described by Fransen et al. (1985). MRNA was separated on a denaturating formaldehyde gel as described by Gerard and Miller(1986) (2.5 $\mu$g poly-$A^+$RNA per lane) and blotted on a nylon membrane (Hybond-N, Amersham) as described by Fourney et al. (1988). The blot was screened by hybridization with the 900 bp EcoRI-restriction fragment of the selected mouse cDNA clone labelled to specific activity of 0.5–1×$10^9$ cpms/$\mu$g using a multiprime labeling kit (Amersham, RPN 1600Y). Prehybridization was for 2 hours at 42° C. in 5×Denhardts (100×Denhardts: 20 g Ficoll, 20 g polyvinylpyrrolidone and 20 g BSA (fraction V) per liter), 5×SSC (20×SSC: 3 M NaCl, 0.3M Na acetate.2$H_2O$), 50 mM Na Phosphate pH 7.0, 0.1% SDS, 250 $\mu$g/ml salmon sperm DNA and 50% deionized formamide. Hybridization was performed for at least two nights in the same buffer containing 1×$10^6$ cpms/ml of the labelled probe. Thereafter, the filter was washed two times in 2×SSC, 0.1% SDS followed by two washes in 1×SSC, 0.1% SDS, each time for 15 minutes and at 50° C. Autoradiographical exposure was for two hours at room temperature. Messenger RNA of the following cell lines are analyzed: mouse monocytic PU5-1.8. either uninduced (3 h and 24 h: lanes 1 and 3) or LPS-induced (3 h and 24 h: lanes 2 and 4); 24 hours uninduced and LPS-induced mouse macrophage 2C11–12 cells (lanes 5 and 6); 24 hours uninduced and LPS-induced mouse T-lymphoma EL-4 (lanes 7 and 8); 24 hours uninduced and LPS-induced mouse B-myeloma NSo (lanes 9 and 10); and 24 hours uninduced and LPS-induced mouse fibrosarcoma L-29 (lanes 11 and 12). LPS-induction was as described in section 1.1.

FIG. 8*a* is a schematic representation of the bacterial expression plasmid pmTNF-MPH.

FIG. 8*b* and FIG. 8*b* (con't 1) represents the total DNA sequence of the bacterial expression plasmid pmTNF-MPH.

Figure 9:
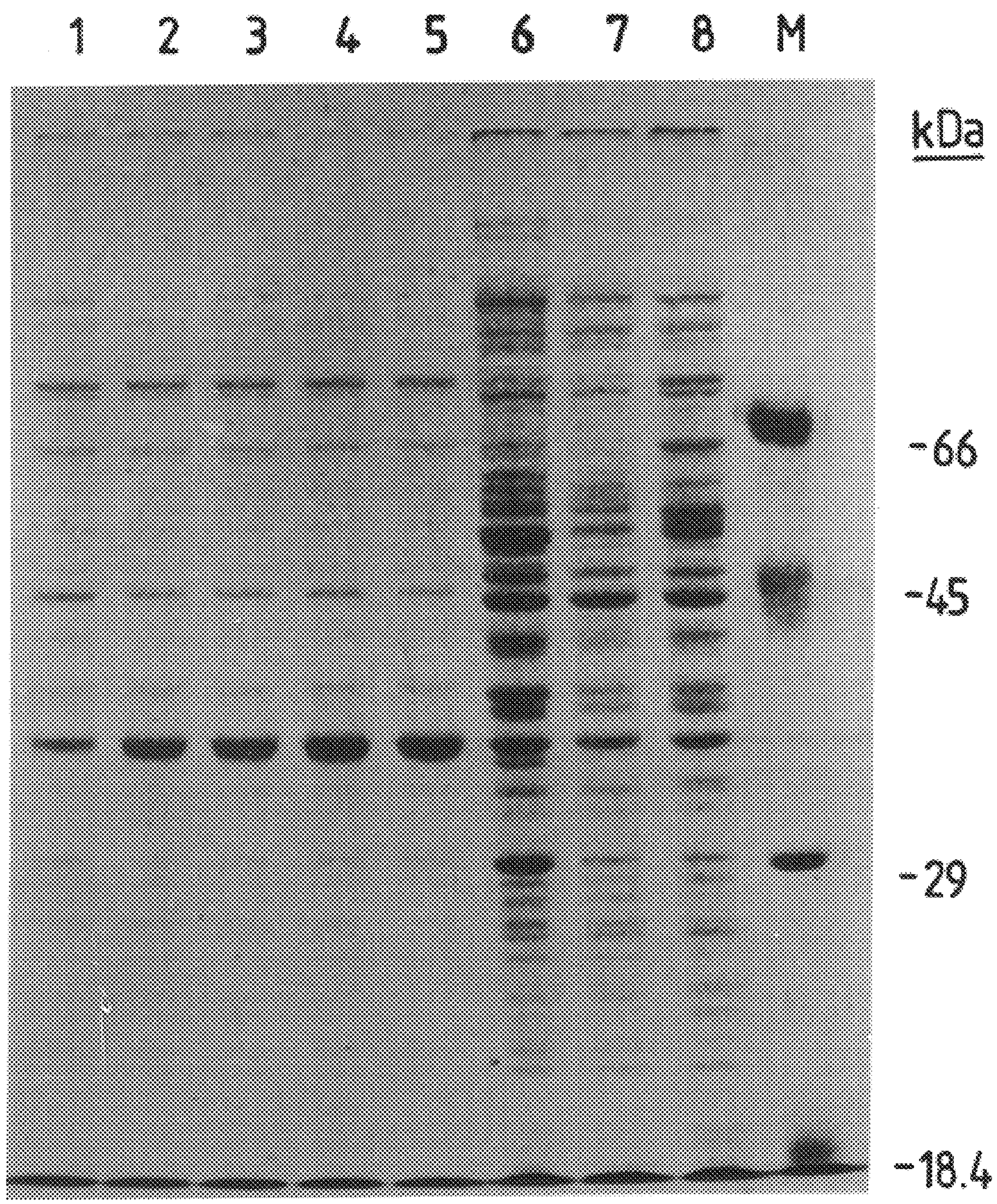

FIG. 9 represents the SDS-PAGE gel analysis of *E. coli* strain transformed with the expression plasmid pmTNF-MPH-PU1280-Eco47III at different times after temperature-induced expression.

Lanes 1 to 5: pmTNF-MPH-PU1280-Eco47III in K12ΔH after 1 h, 2 h, 3 h, 4 h and 5 h induction at 42° C.; lane 6: pmTNF-MPH-PU1280-Eco47III in K12ΔH after 5 h induction at 28° C.; lanes 7–8: pmTNF-MPH in K12ΔH after 5 h induction at 28° C. and 42° C., respectively.

A culture of K12ΔH harbouring pmTNF-MPH-PU1280-Eco47III, grown overnight in Luria broth a 28° C. with rigorous shaking in the presence of 10 $\mu$g/ml tetracycline, was inoculated into fresh Luria broth containing tetracycline (10 $\mu$g/ml) and grown to an optical density at 600 nm of 0.2 under the same conditions as for the overnight culture. At this density of bacterial growth, half of the culture was shifted to 42° C. to induce expression, while the other half remained at 28° C. as a control. At several time intervals, aliquots were taken which were extracted with one volume of phenol equilibrated against M9 salts (0.1% ammonium chloride, 0.3% potassium dihydrogen phosphate, 1.5% disodium hydrogen phosphate, 12 molecules of water) and 1% SDS. At the same time the optical density at 600 nm of the culture is measured. The proteins are precipitated from the phenol phase by addition of two volumes of acetone and stored overnight at −20° C. The precipitate is pelleted (Biofuge A, 5 min, 13000 rpm, room temperature), air dried, dissolved in a volume of Laemmli sample buffer (+β-mercaptoethanol) according to the optical density of the culture sample and boiled for 3 minutes. Samples were then put on a SDS polyacrylamide gel (12.5%) according to Laemmli (1970). Afterwards the gel was first treated for at least 1 hour at 4° C. with a 10% trichloroacetic acid solution and subsequently immersed in a 1/10 diluted CBB-staining solution (0.5 g CBB-R250 (Serva) in 90 ml of methanol: $H_2O$ (1:1 v/v) and 10 ml glacial acetic acid) and left for about one hour on a gently rotating platform. After destaining in 30% methanol–7% glacial acetic acid (two to three washes of about 30 min each) the gel was dried between two sheets of cellophane at room temperature.

Figure 10:
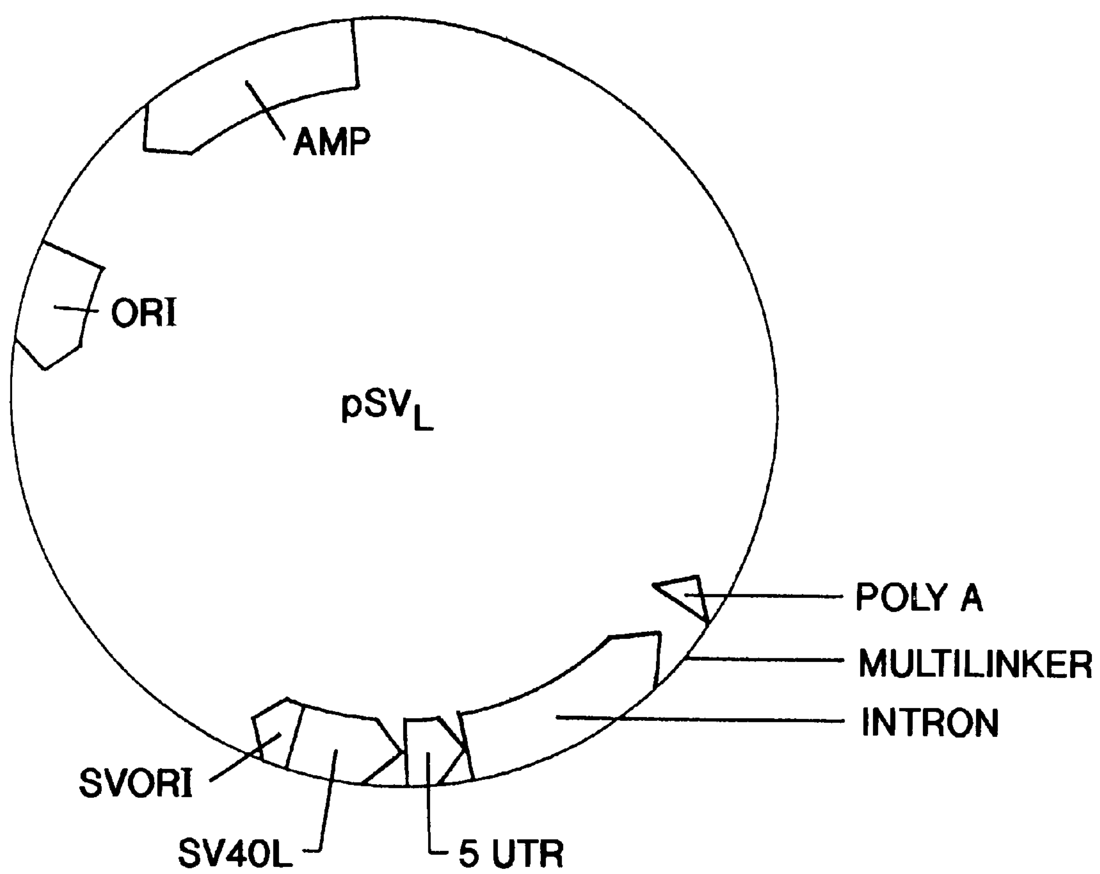

FIG. 10 is a schematic representation of the expression vector pSVL used for transient expression of the mouse and human polypeptide of the invention in COS1 cells. Apart from prokaryotic sequences (ORI of replication and AMP resistance gene), the vector contains the SV40 origin of replication (SVORI) and part of the SV40 late region: SV40 late promoter and enhancer (SV40 L) sequence, the 5' untranslated region (5UTR) followed by a multilinker sequence, donor and acceptor splice sites of the late 16s MRNA (INTRON) and the late SV40 polyadenylation site (poly A).

Figure 11:
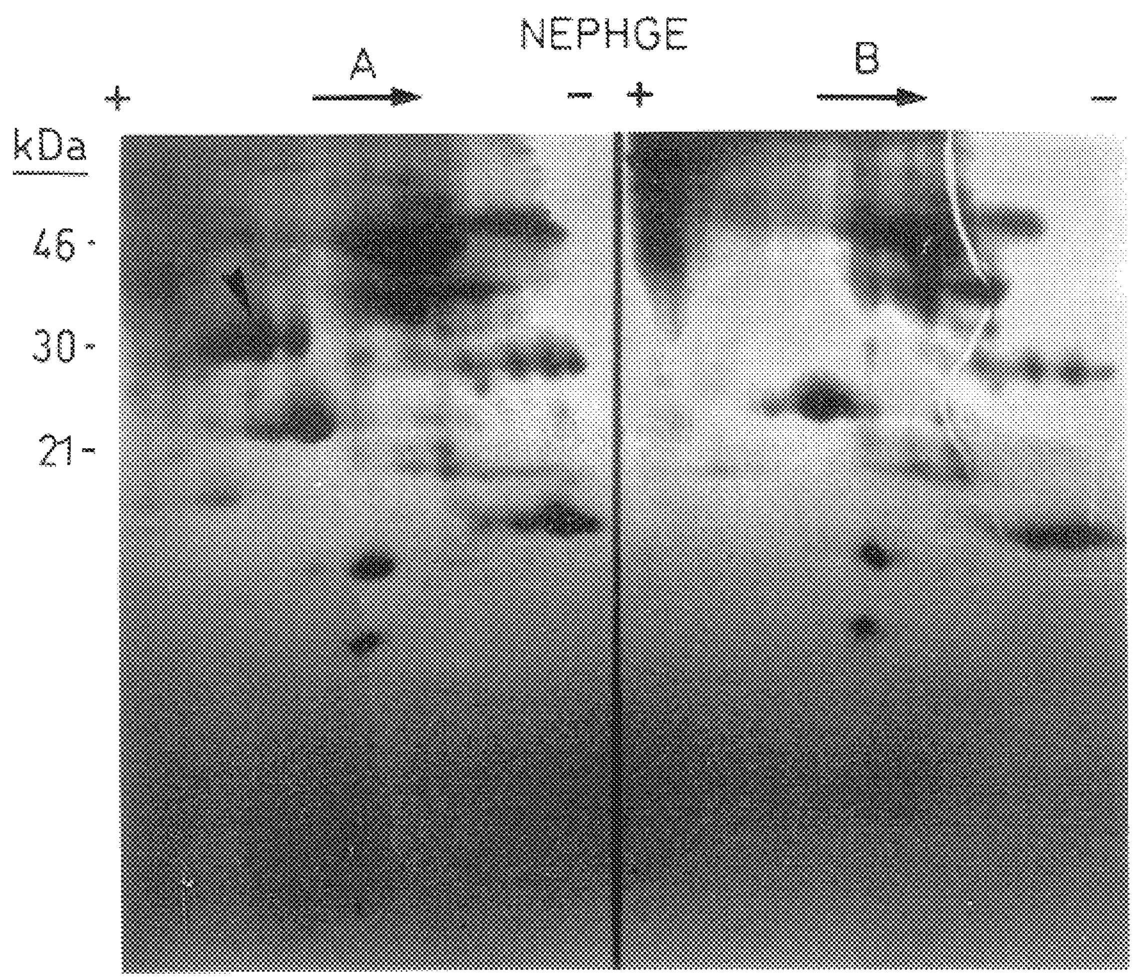

FIG. 11 is a 2-dimensional nonequilibrium pH gel electrophoresis (2D-NEPHGE) (non-reducing conditions) and fluorography of 5 ml conditioned medium of COS1 cells transfected with the expression plasmid pSV-PU1280-HdIII (A) or the control plasmid pSV (B) radiolabeled with $^{35}$S-methionine (24 h) as described. The ±30 kDa triple peptide spot corresponding to the mouse polypeptide of the invention is indicated by an arrow.

Figure 12:
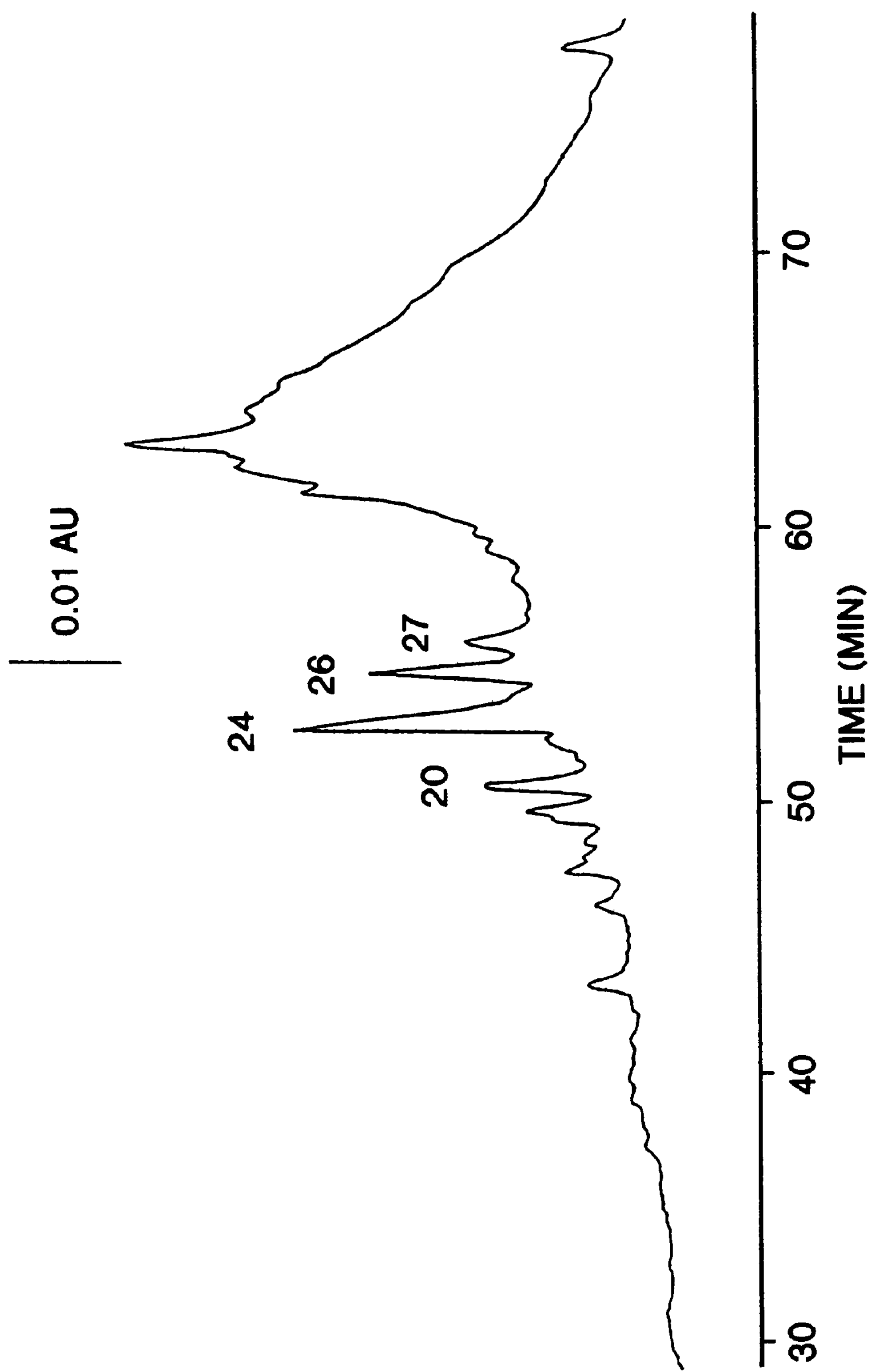

FIG. 12 represents the separation on an aquapore butyl 7 $\mu$ column (Brownlee–10 cm×2.1 mm) of peptides generated by partial formic acid hydrolysis (as described) of the mouse polypeptide of the invention as secreted by pSV-PU1280-HdIII-transfected COS1 cells. Peptides were eluted with a linearly increasing gradient of 0.1% trifluoroacid (TFA) in acetonitrile and detected by UV absorbance at 214 nm. Peptides 20/24/26 and 27 were selected for sequencing (Applied Biosystems 477 A).

Figure 13:
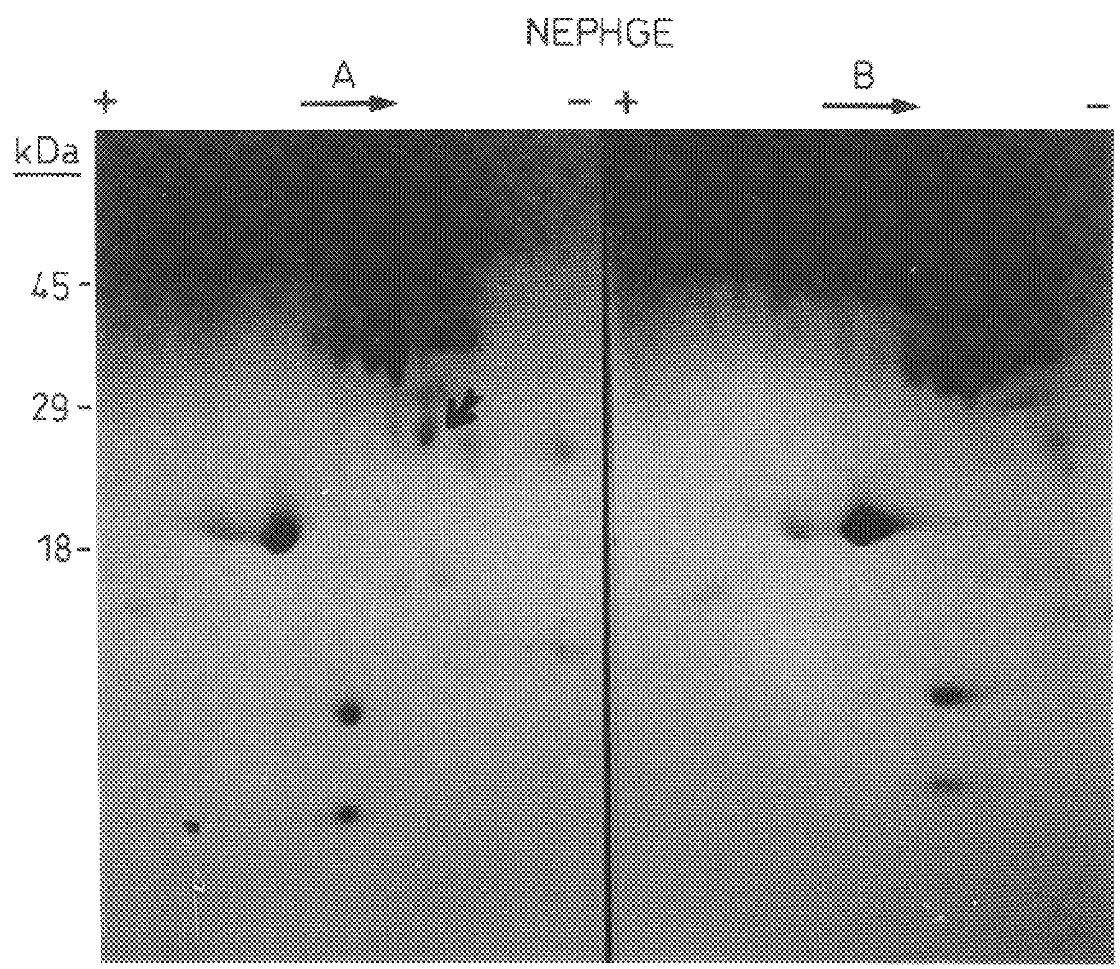

FIG. 13 represents the 2-dimensional non-equilibrium pH gel electrophoresis (2D-NEPHGE) (non-reducing conditions) and fluorography of 5 ml CM of COS1 cells transfected with the expression plasmid pSV-T1200 containing the human analogue of the invention cDNA (A) or the control plasmid pSV (B), radiolabeled with $^{35}$S-methionine as described (24 h). The ±27-kDa peptide spot corresponding to the human polypeptide of the invention is indicated by an arrow.

Figure 14:
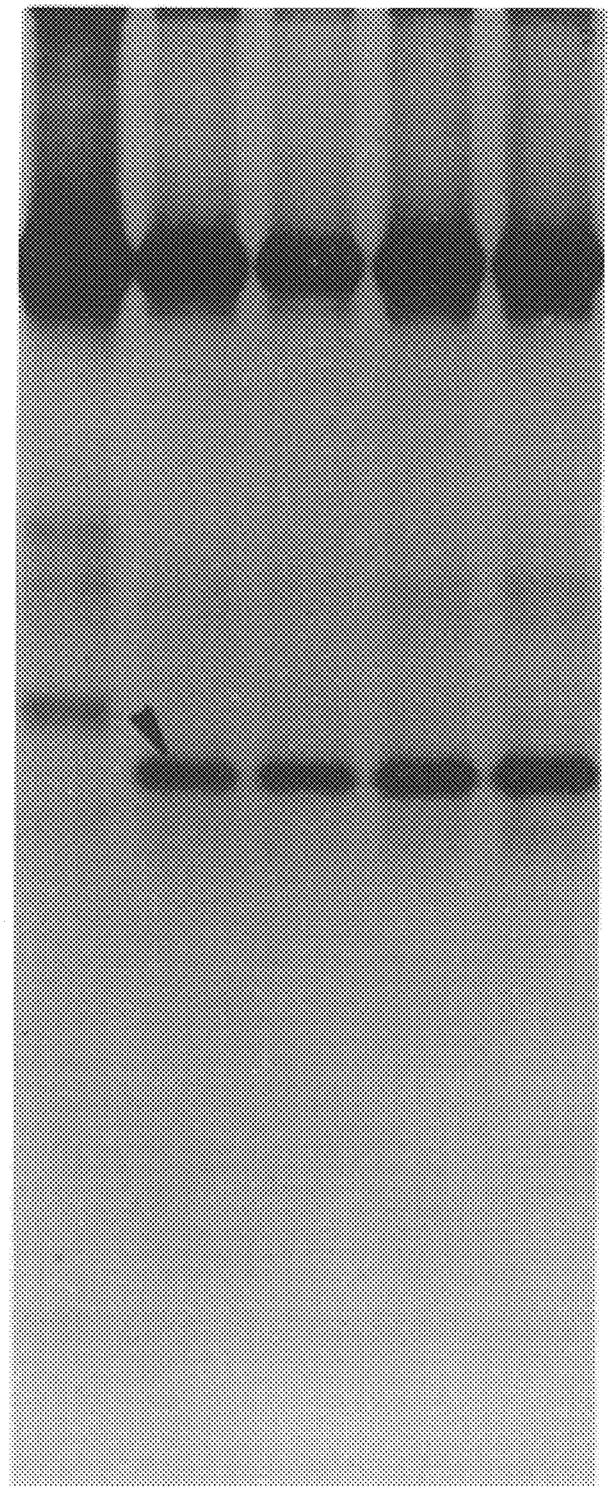

FIG. 14 represents the SDS-polyacrylamide gel electrophoresis (non-reducing conditions) and fluorography of proteins secreted in 1 ml conditioned medium (CM) of Sf9 cells (±$10^6$ cells) infected with either wild type baculovirus (lane 1) or recombinant baculovirus containing the mouse cDNA of the invention (lanes 2, 3, 4, 5) and radiolabeled with $^{35}$S-methionine for 18 h, 24 h post-infection as described.

The ±28 kDa protein corresponding to the mouse polypeptide of the invention is indicated by an arrow.

Figure 15:
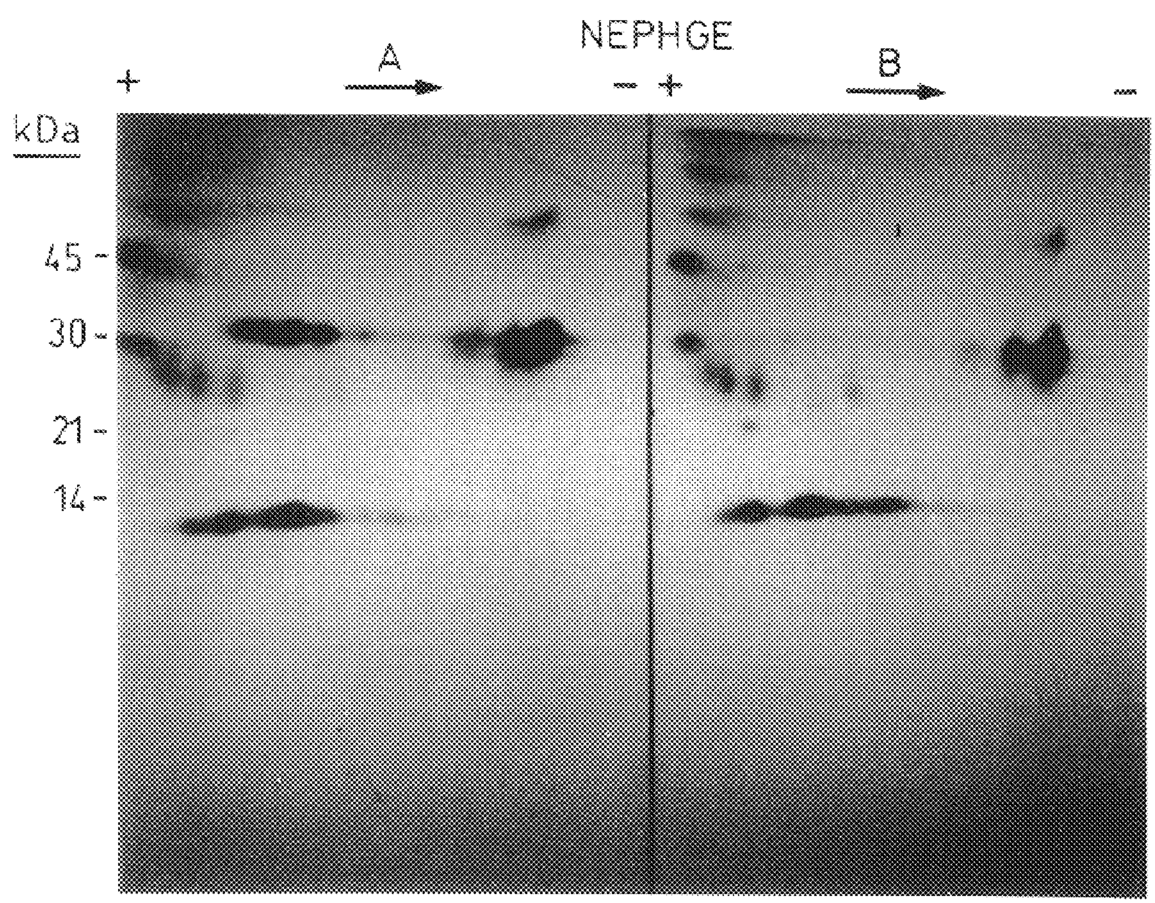

FIG. 15 represents the 2D-NEPHGE (reducing conditions) analysis and fluorography of 5ml CM of HeLa cells infected with recombinant vaccinia virus containing the mouse cDNA of the invention (A) or wild type vaccinia virus (B), labeled with $^{35}$S-methionine for 24 h post- infection. The ±34 kDa protein of the invention is indicated by an arrow.

Figure 16:
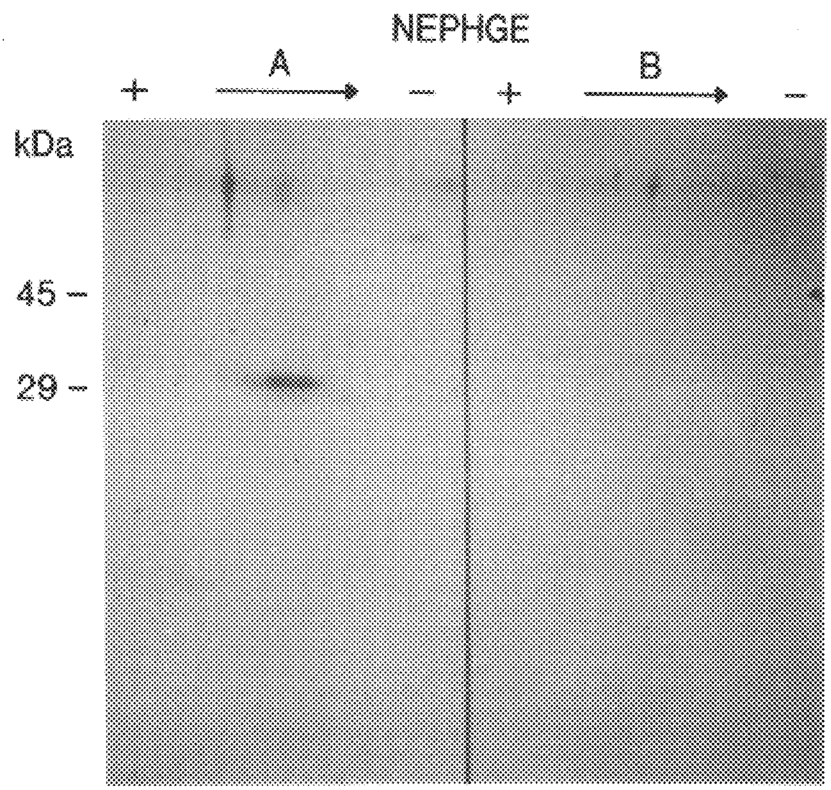

FIG. 16 is a Western blot analysis with the anti-human peptide 3 polyclonal antiserum, of 5 ml CM of HeLa cells infected with recombinant vaccinia virus containing the human cDNA of the invention (24 h harvest)(A) or wild type vaccinia virus separated on 2D-NEPHGE (reducing conditions). The ±30 kDa protein of the invention is indicated by an arrow.

Figure 17:
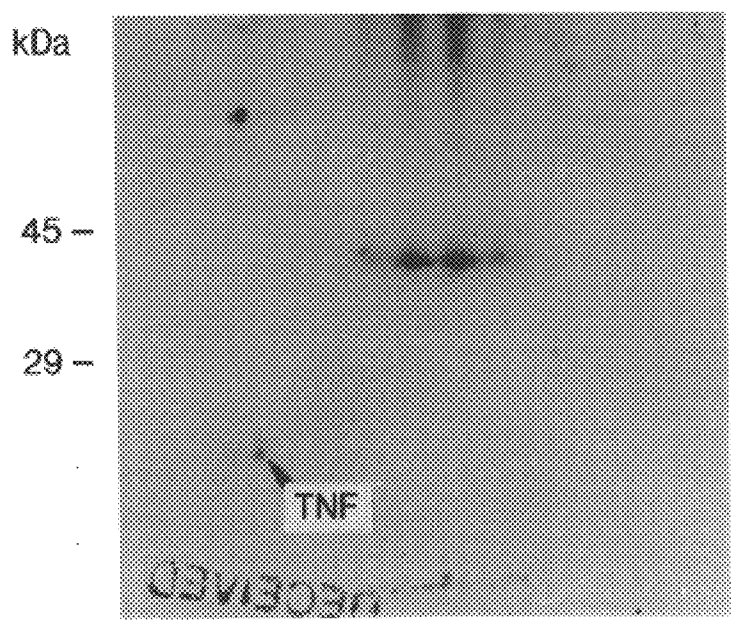

FIG. 17 is the Western blot analysis with the anti-mTNF-MPH-mouse cDNA fusion protein antiserum of proteins secreted in 20 ml CM of LPS-induced (10 $\mu$g/ml; 24 h) PU5-1.8 cells, separated on 2D-NEPHGE (reduced conditions). The mouse polypeptide of the invention is indicated by an arrow. TNF which is also recognized by the antiserum is also indicated.

Figure 18:
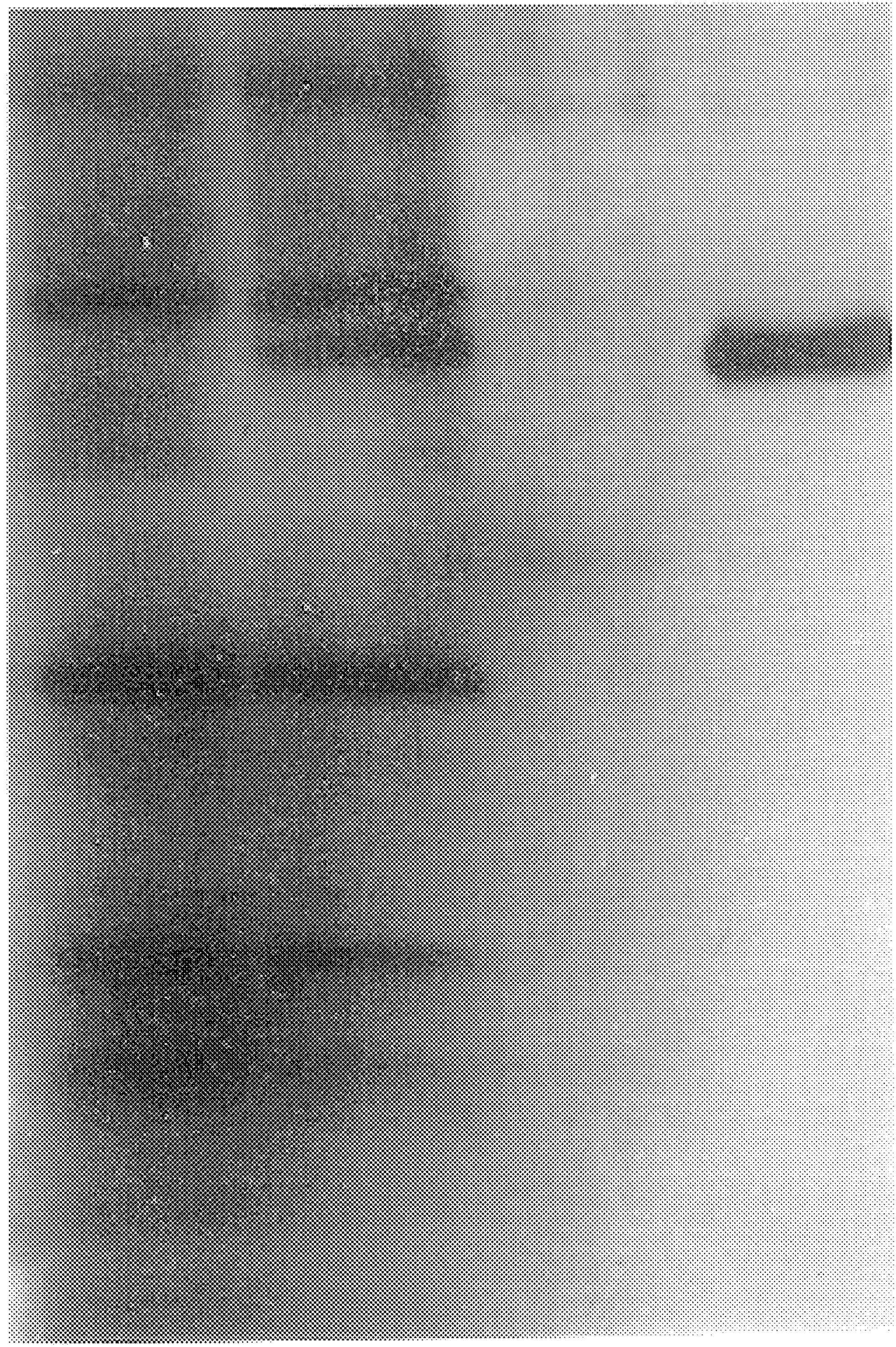

FIG. 18 represents the immunoprecipitation of the native form of the mouse polypeptide of the invention secreted by transfected COS1 cells, with the anti-mTNF-MPH-mouse cDNA fusion protein antiserum. 850 $\mu$l of $^{35}$S-methionine-labeled CM of COS1 cells transfected with pSV control plasmid (lane 1) or pSV-PU1280-HdIII plasmid (lane 2) was immunoprecipitated as described and analyzed by SDS-PAG-fluorography (lanes 3 and 4 correspond to pSV and pSV-PU1280-HdIII, respectively). The immunoprecipitated mouse polypeptide of the invention is indicated by an arrow.

Figure 19:
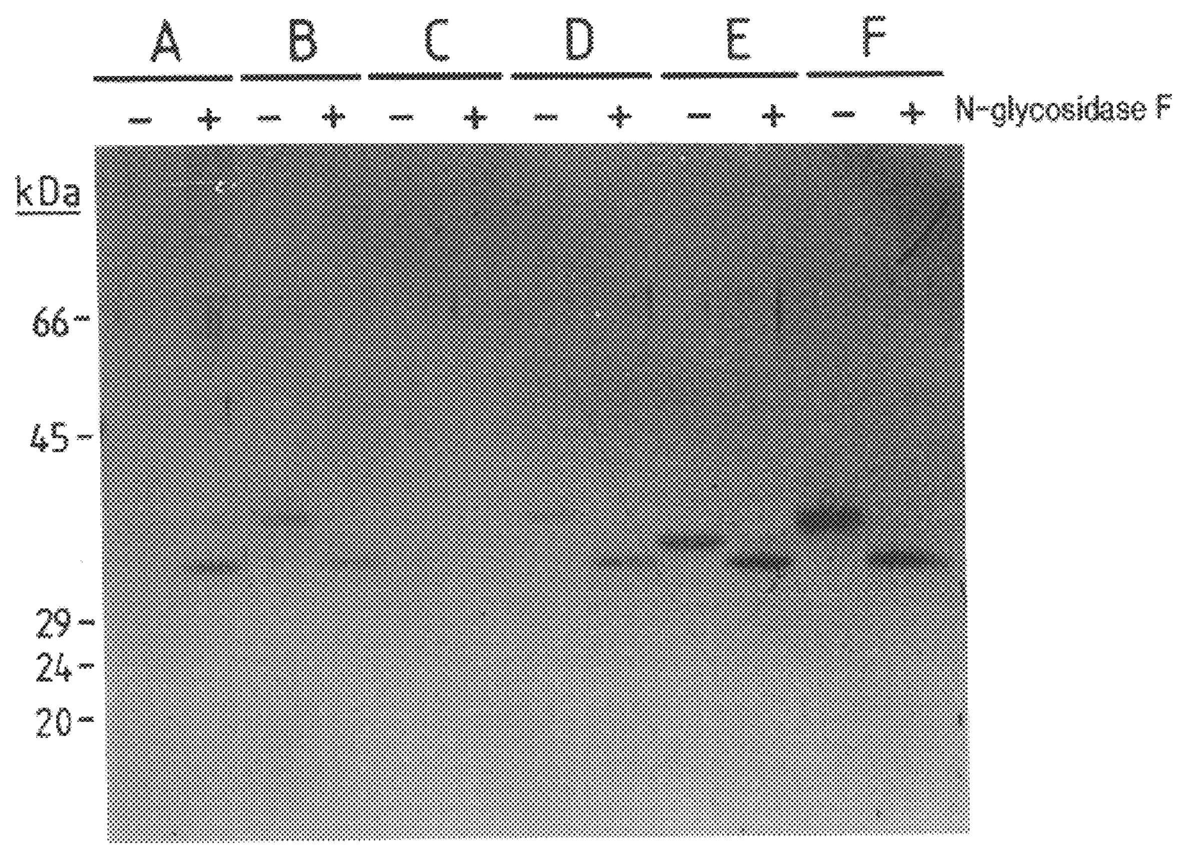

FIG. 19 represents the characterization of the N-glycosylation of the mouse polypeptide of the invention by N-glycosidase F treatment: 500 $\mu$l CM of uninduced (A) or LPS (24 h, 10 $\mu$g/ml) induced PU5-1.8 cells (B), of wild type vaccinia virus infected (C) or recombinant mouse cDNA vaccinia virus infected HeLa cells (D), of recombinant mouse cDNA baculovirus-infected Sf9 cells (E) or pSV-PU1280-HdIII transfected COS1 cells (F) was untreated (–) or treated with N-glycosidase F (+) (as indicated by the manufacturer) and analyzed by Western blotting with the anti-mTNF-MPH-mouse cDNA fusion protein antiserum.

Figure 20:
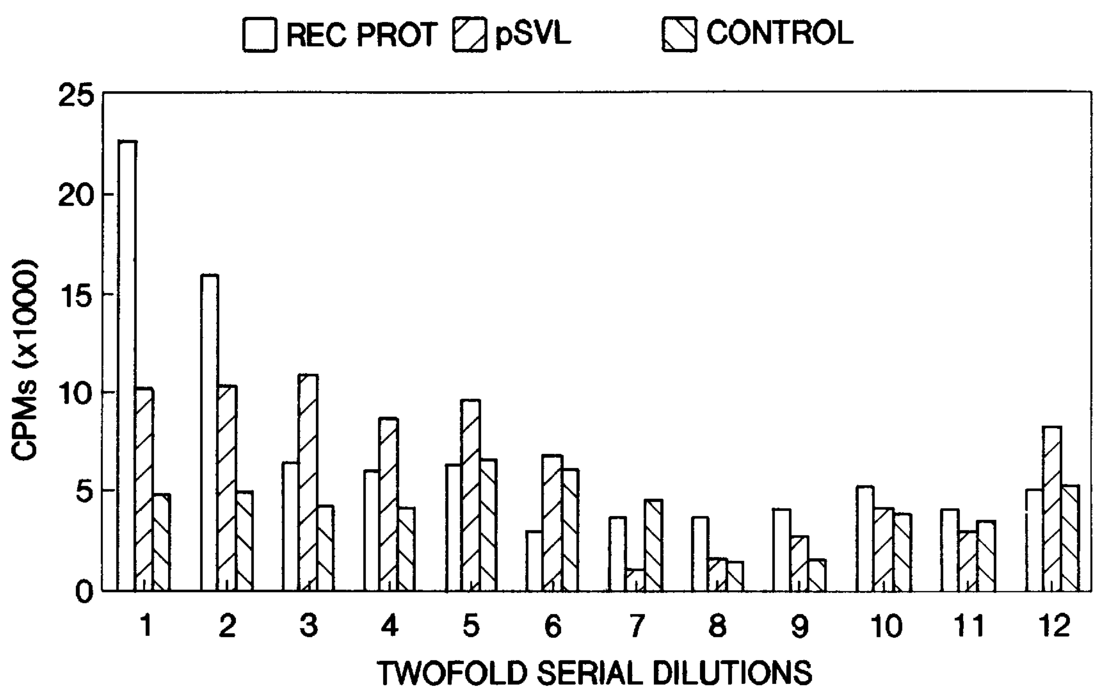

FIG. 20 represents the thymocyte proliferation assay as described in section 12.1. performed in the presence of 2 $\mu$g/ml of PHA and a two-fold serial dilution of the mouse polypeptide of the invention (rec prot: start concentration ±5–10 ng/ml) or pSVL control medium. The proliferation was measured by the incorporation of $^3$H-thymidine for 24 hours following a 72-hour incubation of the cells with the samples (see y-axis representing the amount of CPM×1000). As negative control, conditioned medium of pSVL-transfected COS1 cells, treated in exactly the same way as the medium obtained from pSV-PU1280-HdIII-transfected cells or PBS, was tested in the presence of PHA.

For each group of three contiguous rectangles, the left rectangle corresponds to the recombinant protein of the invention, the middle rectangle corresponds to the negative control (pSVL) and the right rectangle corresponds to the control.

The x-axis corresponds to the two-fold serial dilutions wherein the number 1represents the start concentration of 5 to 10 ng/ml of the polypeptide of the invention, 2 represents 2 times less, etc.

Figure 21A:
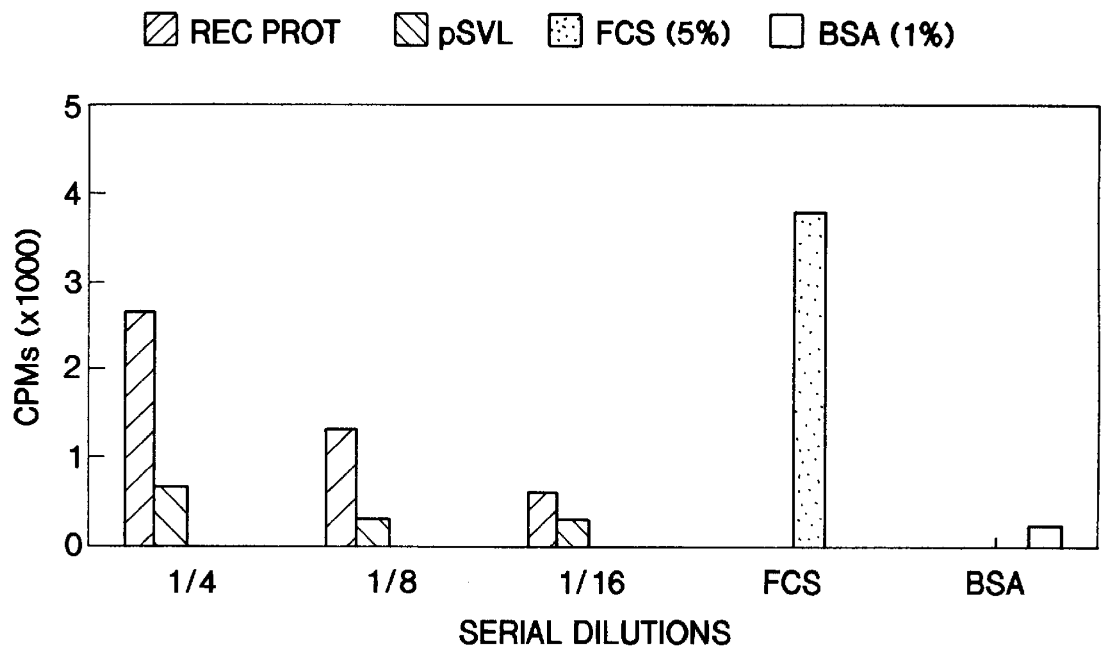
Figure 21B:
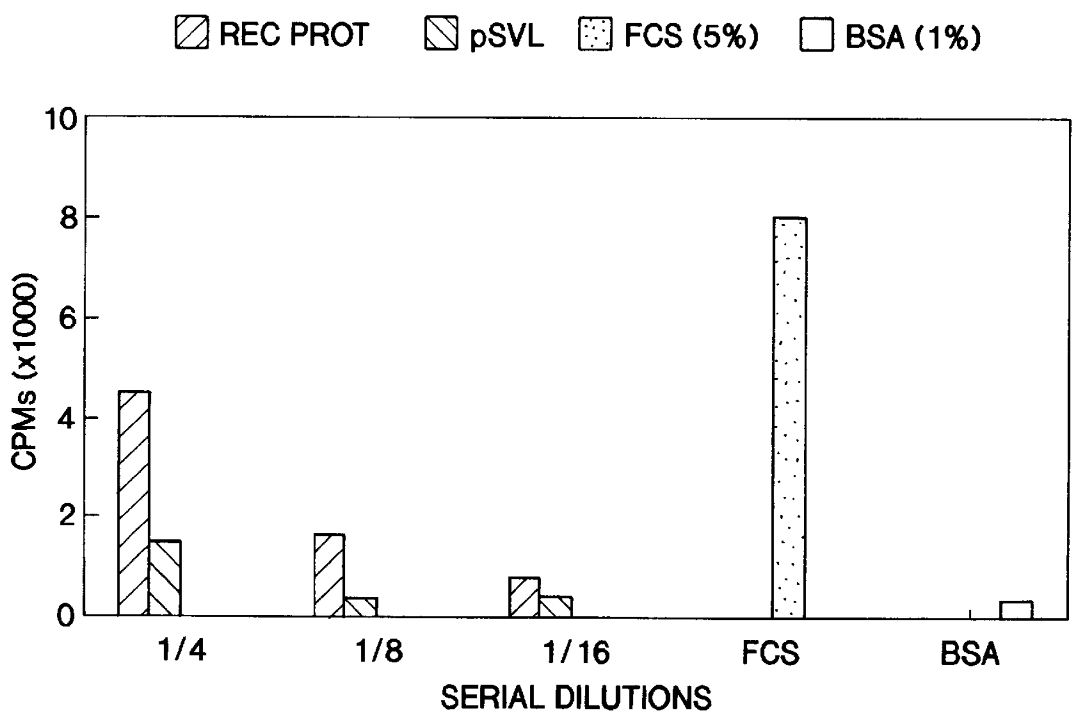

FIG. 21*a* and FIG. 21*b* represent the proliferative effect of the mouse polypeptide of the invention respectively on rat pre-osteoblast cells (FIG. 21*a*) and osteoblast cells (FIG. 21*b*). The assay was performed as described in section 12.5. both on preosteoblast and osteoblast cells by adding a two-fold serial dilution of the mouse polypeptide of the invention (rec prot: start concentration ±5 ng/ml) or pSVL (see FIG. 20) as negative control. 5% of fetal calf serum (FCS) and 1% of bovine serum albumin (BSA) were included as positive and negative assay controls, respectively.

The y-axis represents the amount of CPM×1000 and the x-axis corresponds to serial dilutions. For each group of two contiguous histograms, the left one corresponds to the recombinant protein of the invention, while the right one corresponds to pSVL; the highest single histogram corresponds to FCS (5%) while the lowest single one corresponds to BSA.

Figure 22:
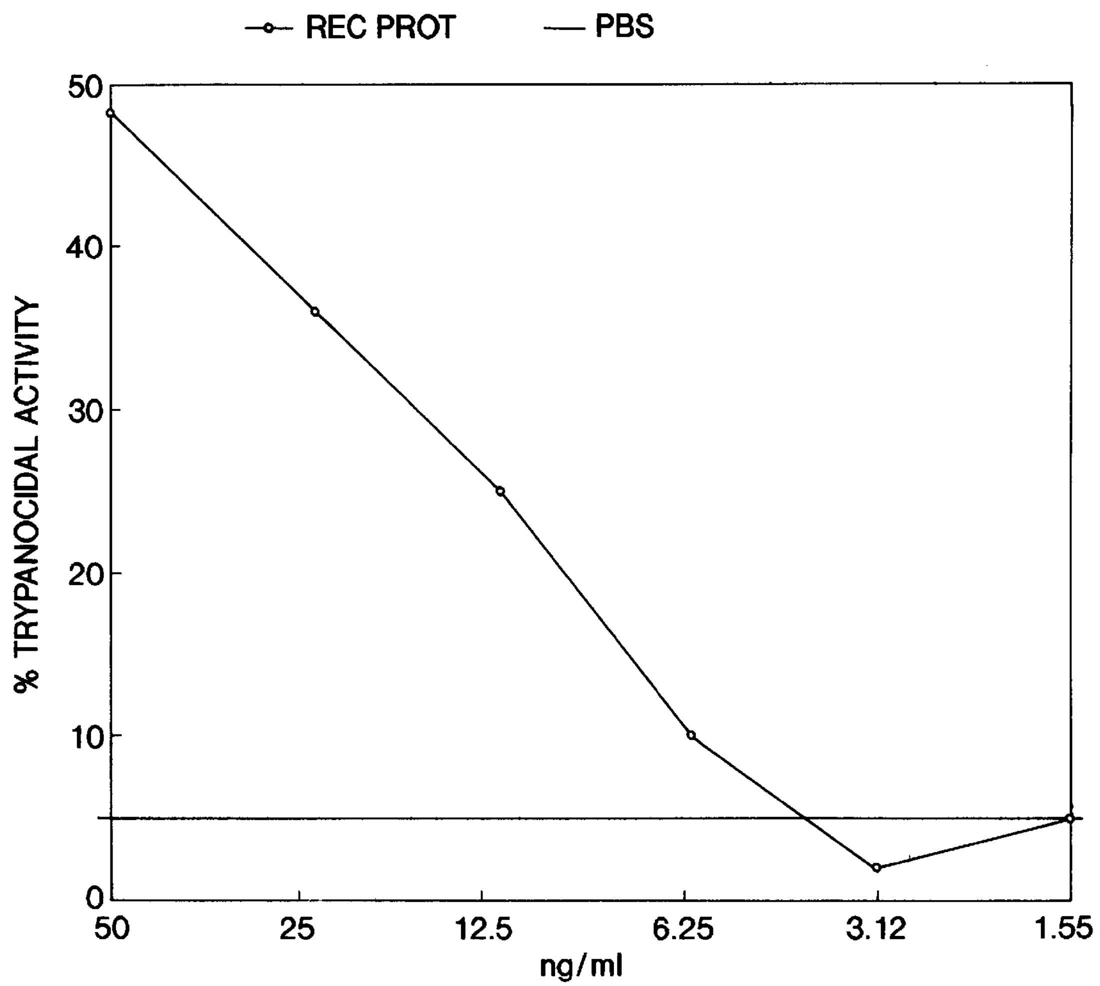

FIG. 22 represente the trypanocidal effect of the polypeptide of the invention on Trypanosma brucei brucei in vitro. The assay was performed as described in section 12.6 on $2\times10^6$ parasites by adding a two-fold serial dilution of the mouse polypeptide of the invention (recombinant protein start concentration: 50 ng/ml) or PBS (negative control). The y-axis represents the % of trypanocidal activity of living parasites and the x-axis corresponds to serial dilutions.

EXAMPLES

1. Preparation of libraries 1.1. Lipopolysaccharide (LPS)-induction of the mouse macrophage cell line PU5-1.8

The established mouse monocyte/macrophage cell line PU5-1.8 (PU.5-1R) (purchased from the American Type Culture Collection, Baltimore, Md., USA; ATCC TIB61) was chosen for lipopolysaccharide, endotoxin (LPS)-induction. However, other mouse cell lines of the monocyte-macrophage lineage (such as J-774, RAW309, WR19M, Wehi3B, etc.) or primary macrophages (peritoneal macrophages, alveolar macrophages) can also be used. Cells of the PU5-1.8 cell line were cultured as spinner cultures in RPMI-1640 medium enriched with 10% non-inactivated preselected batches of fetal calf serum (FCS, Gibco, Paisley, Scotland). When reaching a density of 1 to $1.5\times10^6$ cells/ml, cells were subcultured at a starting density of $5\times10^5$ cells/ml in roller bottles in the same growth medium. At confluence ($\pm1.5\times10^6$ cells/ml), the cells were washed 3 times with RPMI-1640, resuspended at a cell concentration of $3.5\times10^6$ cells/ml in RPMI-1640, and stimulated by addition of 10–15 μg/ml of LPS (LPS *E. coli* 055:B5 Difco Laboratories, Detroit, Mich., USA) for 20–24 hours. After induction the cells were collected by centrifugation, washed three times with icecold phosphate-buffered saline (PBS) and stored at −70° C. until preparation of the mRNA. Also, mRNA was prepared from uninduced PU5-1.8 cells. To this end, cells were treated as indicated for LPS-induced cells but without addition of LPS during induction. The conditioned medium of untreated and LPS-induced PU5-1.8 cells was tested for the presence of TNF-α, IL-1 and IL-6 using appropriate bioassays. TNF activity was assayed on L-929 cells (Ruff and Gifford, 1980). IL-1 activity was measured using an indirect assay system (Van Damme et al. 1987). IL-6 was measured in terms of hybridoma growth activity (Van Snick et al., 1986).

1.2. Preparation of LPS-minus and LPS-plus mRNA of PU5-1.8 cells

As a source of mRNA, uninduced (LPS-minus) and LPS-induced (LPS-plus) PU5-1.8 cells were used. Total cytoplasmic RNA was extracted by lysing the cells in Nonidet P40 followed by phenol extraction of the lysate as described (Fransen et al., 1985). Polyadenylated RNA (poly $A^+$–RNA) was purified from total RNA by oligo dT- cellulose chromatography (Type 3; Collaborative Research, Boston, Mass., USA) as described by Chirgwin et al. (1979). The resulting RNA was further fractionated on a 5–20% sucrose gradient in 10 mM Tris-HCl, pH 7.5, 1 mM EDTA by centrifugation at 40,000 rpm for 19 hours at 4° C.

1.3. Construction of a cDNA library of a 17S-mRNA fraction of LPS-induced PU5-1.8 cells The mRNAs from the 17S fraction of the gradient (the fraction numbers 16, 17, 18 of the gradient as shown in FIG. 4) of LPS-induced MRNA of PU5-1.8 cells were used for the construction of the cDNA library. These fractions were selected on the basis of their capacity to induce the synthesis of mTNF upon injection in Xenopus laevis oocytes. The conditions used for the construction of a cDNA library in pAT153 plasmids were chosen according to established state-of-the-art methods. To this end, the RNA from the 17S fraction was precipitated by addition of 0.1 volume of 2M Na acetate pH 5.3 and 2 volumes of ethanol; the precipitate was redissolved in water and the solution was heated for two minutes at 70° C. and then quickly chilled on ice. The conditions for the first-strand synthesis were as follows:

±50 μg poly $A^+$RNA/ml 50 mM Tris HCl, pH 8.3

50 mM KCl 10 mM $MgCl_2$ 10 mM DTT 0.5 mM of each dNTP (N=A, T, C, or G) with 1/1000 dCTP replaced by $\alpha(^{32}P)$-dCTP at 800 Ci/mmole (code PB 10385, Amersham, Buckinghamshire, England)

60 μg/ml poly $dT_{10}$ (Pharmacia, Uppsala, Sweden)

1000 U/ml human placental RNase inhibitor (Amersham, Buckingshamshire, England)

1000 U/ml reverse transcriptase (Biores, Waerden, The Netherlands)

The reaction was performed in a total volume of 100 μl at 41° C. for 1 hour. The reaction mixture was then extracted once with phenol/chloroform/isoamylalcohol (25/24/1), twice with diethyl ether, and the DNA was precipitated by adding 1 volume of 4M ammonium acetate and 4 volumes of ethanol. The pellet was redissolved in water and the precipitation step was repeated.

The precipitate was redissolved in 60 μl 15 mM potassium phosphate buffer, pH 6.9, 0.25 mM EDTA and treated with 2 μg RNAse A (Boehringer Mannheim, FRG) at 37° C. for 30 minutes. Subsequently, the mixture was boiled for 2 minutes and immediately quenched on ice. Potassium phosphate buffer, pH 6.9, $MgCl_2$, DTT and dNTPs were added to final concentrations of 100 mM, 10 mM, 10 mM, and 1 mM, respectively. The reaction was initiated by addition of 330 U/ml *E. coli* polymerase I (Boehringer Mannheim). Second-strand synthesis was performed at 15° C. for 6 hours in a total volume of 300 μl. The reaction was stopped by adding EDTA, pH 8.0 to a final concentration of 25 mM and the mixture was phenol-extracted and precipitated as described (see above). The precipitate was redissolved in 125 mM NaCl, 25 mM sodium acetate, 1 mM zinc acetate, pH 4.5 and treated with 20 units of S1-nuclease (BRL, Neu-Isenburg, FRG) for 20 minutes at 37° C. The reaction was stopped by the addition of EDTA pH 8.0 to a final concentration of 20 mM, neutralized by the addition of Tris-HCl, pH 8.0 to a final concentration of 200 mM and again phenol-extracted as mentioned above. Finally, the dsDNA was precipitated by addition of 1/10 volume potassium acetate, pH 4.8 and 1 volume of isopropanol.

The pellet was redissolved in buffer containing 30 mM NaCl, 10 mM Tris-HCl, 1 mM EDTA, pH 8.0 and size-fractionated on a Biogel A 50 m gel filtration column (0.8×12 cm) (Biorad, CAlif., USA) equilibrated against the same buffer.

Fractions containing DNA of >500 base pairs were pooled and precipitated as above.

The double-stranded cDNA was oligo(dC) tailed using the following conditions:

±2 μg double-stranded cDNA/ml 100 mM potassium cacodylate, pH 7.2

−2 mM $CoCl_2$

200 μM DTT

40 μM deoxy $(5\text{-}^3H)$cytidine triphosphate (17 Ci/mmole; Amersham)

400 Units/mnl terminal deoxynucleotidyl transferase (Pharmacia)

The reaction was performed at 37° C. until around 20–25 dC residues were incorporated per 3' OH-end and was stopped by the addition of EDTA pH 8.0 to a final concentration of 25 mM followed by phenol extraction, ether extraction, and precipitation as described above.

Oligo dG-tailing of the PstI-digested plasmid pAT153 was carried out under similar conditions except that 4 μM deoxy (8-$^3$H) guanosine 5' triphosphate (25 Ci/mmole; Amersham) was used instead of 40 $\mu$M d($^3$H) cytidine 5' triphosphate, and that the concentration of the linearized plasmid DNA was 16 pmole/ml. The oligo dC-tailed double-stranded cDNA was annealed with the oligo dG-tailed vector as described (Maniatis et al., 1982.).

The *E. coli* strain DH1($\lambda$) was transformed (Hanahan, 1983) using 10 ng of vector DNA per 100 $\mu$l of competent cells. Transformation mixtures were plated on Millipore HATF (0.45 $\mu$m) filters (Millipore, Bedford, Mass., USA) and layered on top of Luria broth (LB) agar plates containing 10 $\mu$g/ml of tetracycline. After propagation, the filters were placed on fresh LB-agar plates also containing 20% glycerol and stored at −20° C. In this way, a 17S mouse cDNA library of about 25,000 clones was obtained.

2. Isolation of the cDNA clones coding for the selected sequence 2.1. Isolation of the selected mouse cDNA 2.1.1. Plus-minus screening of the 17S mouse PU5-1.8 cDNA library The colonies were lysed in situ and fixed on replicas of the mouse cDNA library (Hanahan and Meselson, 1980). Two sets of replicas were screened by differential hybridization: the plus probe being a $^{32}$P-labelled cDNA from LPS-induced PU5-1.8 17S mRNA, the minus probe being $^{32}$P-labelled cDNA from uninduced PU5-1.8 17S MRNA. This cDNA was synthesized essentially as previously described (see 1.3.) except that only 15 $\mu$M of dCTP was used, to which $\alpha$($^{32}$P) dCTP (6000 Ci/mmole, Amersham) was added to a concentration of 2 $\mu$M. Colony hybridization was carried out at 42° C. for 40 h in 20% deionised formamide, 5×SSC, 5×Denhardt solution, 25 mM sodium phosphate buffer pH 6.5, 20 $\mu$g/ml of sonicated and denaturated *E. coli* DNA and $^{32}$P-labelled CDNA probe (10$^6$ cpms/ml) after an overnight prehybridization in the same buffer but without labelled cDNA.

Before autoradiography, the filters were washed three times for 30 minutes in 2×SSC, 0.1% SDS at 42° C.

The clones that showed preferential hybridization with the plus probe were picked up, grown individually, and streaked on new filters for a second round of plus/minus hybridization. Those clones that were consistently positive in both rounds of hybridization were retained. They are referred to as "LPS-induced" clones.

2.1.2. Characterization of a selected LPS-induced cDNA fragment from the PU5-1.8 cDNA library Of all the LPS-induced mouse clones isolated by plus-minus screening, DNA was prepared using the Triton X100-lysozyme lysis method essentially as described (Kahn et al., 1979). The length of the cDNA insert was assessed by digestion with the restriction enzyme PstI and by separating the insert from the pAT153 vector by agarose gel electrophoresis.

The selected LPS-induced clone has an insert of 446 bp, divided into two subfragments of 332 bp and 114 bp by an internal PstI site.

This clone was characterized with respect to its degree of LPS inducibility, its macrophage cell-type specificity, and its gene expression in other cells of the immune system (T cells and B cells) by Northern blot analysis. The selected LPS-induced gene fragment hybridized only with a MRNA of an approximate length of 1475 base pairs present in uninduced or LPS-induced mouse macrophage cells and not with MRNA of uninduced or LPS-induced EL-4, and NSo cells, and very weakly with MRNA of uninduced or LPS-induced L929 cells. Hence, the selected gene fragment behaved as LPS-induced and as being dominantly expressed in macrophage.

2.1.3. Construction of a LPS-induced PU5-1.8 cDNA library in $\lambda$ZAP II

In order to obtain the full-size cDNA information of the selected LPS-induced PU5-1.8 cDNA fragment, a cDNA library was constructed in the $\lambda$ZAP II vector system (Stratagene, La Jolla, Calif., USA). To this end, mRNA was prepared from PU5-1.8 cells induced for 3 hours with LPS (see section 1.1.). The synthesis of cDNA was performed as described (section 1.3.) except that it was not tailed with dGTP or dCTP but rather was methylated by dissolving the cDNA pellet in a solution of 100 mM Tris-HCl, 10 mM EDTA, pH 8.0, 80 $\mu$M S adenosyl-methionine (Sigma, St. Louis, Mo., USA) and 1.5 U/mil of RI methylase (Promega, Madison, Wis., USA) for 60 minutes at 37° C. The enzyme was inactivated by heat treatment (10 minutes at 70° C.) and, after cooling to room temperature, $MgCl_2$, DTT, dXTPs and T4 DNA polymerase (Boehringer Mannheim, FRG) were added up to a final concentration of 7 mM, 5 mM, 0.2 mM and 125 units/ml, respectively. The reaction was performed at 18° C. for 1.5 hours.

The enzyme was heat-inactivated and the reaction mixture was phenol-extracted and precipitated as above.

Phosphorylated EcoRI linkers (Pharmacia, Uppsala, Sweden) were ligated to the blunt-ended dsDNA at 13° C. for 48 hours at a ratio of 40:1 for the 3 hours LPS-induced PU5-1.8 cDNA libraries constructed in $\lambda$ZAP II in a ligation buffer containing 1 mM ATP, 50 mM Tris-HCl pH 7.4, 10 mM DTT, 8 mM $MgCl_2$ and, 0.5 U/ml T4 ligase (Boehringer-Mannheim, FRG). The mixture was subsequently heat-treated (10 minutes at 70° C.) and, after cooling to room temperature, Tris-HCl, pH 7.4, NaCl, $MgCl_2$, DTT, and EcoRI enzyme were added to final concentrations of 50 mM, 100 mM, 10 mM, 10 mM, and 3000 U/ml, respectively. Digestion was performed for at least 2 hours at 37° C. The material was then phenol-extracted, ethanol-precipitated, and fractionated by gel filtration over Biogel A 50-m (Biorad, Richmond Calif., USA). All DNA fragments larger than ±400 bp were pooled, freeze dried, and redissolved in 50 mM Tris-HCl, pH 7.4, 12 mM $MgCl_2$, 12 mM $MgCl_2$, 10 mM ATP, 1 mM DTT. To this end , a solution of T4-ligase (Boehringer-Mannheim, FRG) was added to a concentration of 0.5 U/$\mu$l and ligation was performed for at least 3 hours at 16° C. at a molar ratio of 1:2 of insert versus vector for the 3-hour LPS-induced PU5-1.8 cDNA libraries constructed in $\lambda$ZAP II. Packaging of the ligation mixture into phage particles was performed using a packaging mix from Promega (Madison, Wis., USA) according to the protocol recommended by the supplier, except that the chloroform treatment was omitted. The cDNA library constructed in the $\lambda$ZAP II cloning vector was amplified on XL-1 blue cells (Stratagene) and contained 1.8×10$^6$ independent plaques.

2.1.4. Screening for the full-size mouse cDNA corresponding to the LPS-induced gene fragment from the PU5-1.8. cDNA library.

The corresponding full-size mouse sequence was picked up by screening the LPS-induced PU5-1.8. $\lambda$ZAP II cDNA library (section 2.1.3.). Therefore, the library was plated out and plaque-lifted in duplo, using 5- and 8-minute adsorption times, respectively, on Hybond-N membranes (Amersham). The DNA was denatured by alkaline treatment (0.2N NaOH, 1.5M NaCl) neutralized in a Tris HCl buffer (1M Tris-HCl, pH 7.5; 1.5 M NaCl) followed by a frnal wash in 2×SSC and fixed on the membranes by incubation for 2 hours at 80° C. under vacuum. The filters were screened by hybridization using both PstI cDNA fragments of the selected LPS-induced mouse clone cDNA fragment as radioactive probe. The cDNA fragment was labelled to high specific activity ($\pm 8\times10^8$ cpm/$\mu$g) with $\alpha$($^{32}$P)dCTP (3000 Ci/mmol; 10 mCi/ml; Amersham) using a multiprime DNA labelling procedure as provided by Amersham. The filters were prehybridized for 20–24 hours at 50° C. in a solution containing 50% deionized formamide, 4×SSPE, 1% SDS, 0.5% milk powder and 500 $\mu$g/ml denaturated salmon sperm DNA. Hybridization was allowed to proceed for at least 48 hours at 50° C. in 47% deionized formamide, 10% dextrane sulfate, 3×SSPE, 1% SDS, 0.5% milk powder using 0.5-1×$10^6$ cpms of probe/ml.

A first wash was performed in 2×SSC, 0.1% SDS at 30° C. followed by different washes in 1×SSC, 0.1% SDS at 50° C. or at a higher temperature until the background was acceptable. After autoradiography, plaques showing positive hybridization on both filters were further plaque-purified.

Purified plaques were excised in vivo and recircularized by infecting with f1-helper phage to generate the pBluescript phagemids as described by the supplier (Stratagene, La Jolla, Calif., USA). Using these phagemids, DNA was prepared, the cDNA inserts were characterized by partial restriction mapping, and inserts were sequenced.

The combined data allow depiction of the mouse nucleotide sequence coding for the protein corresponding to the selected LPS-induced gene (FIG. 3).

The sequence, numbered from nucleotide 1 to 1362, contains an ATG initiation signal at nucleotide position 187, opening a reading frame of 933 bp that codes for a protein of 311 amino acids (TGA stop codon on nucleotide position 1120). The 3'-end sequence is 243 nucleotides long and contains the 3'-TTATTAT (position 1329), resembling the cytokine consensus sequence 3'-TTATTTAT (Caput et al., 1986), and a short poly A stretch of 11 A residus. However, this part of the cDNA will most propably not be complete as no AATTAAA polyadenylation signal is present at the end of the sequence. The derived amino acid sequence encodes a protein with a calculated molecular weight of 34.5 kDa that contains a computer-predicted N-terminal signal peptide of around 40 amino acids with a hydrophobic core of Pro and Leu residues, preceeded by a rather basic N-terminal region. Algorithms to detect membrane-spanning or membrane-associated amino acid sequences show negative results. Furthermore, the sequence contains a putative N-glycosylation signal (Asn-Leu-Thr; amino acid position 103) and 10 Cys residues.

2.2. Isolation of the cDNA clone encoding the human homologue of the selected mouse polypeptide of the invention 2.2.1. Induction of the human THP-1 cell line for the selected gene product The human monocytic THP-1 cell line (ATCC TIB202) was chosen for the screening of a human cDNA library to pick up the human sequence corresponding to the mouse sequence of the selected LPS-induced gene. However, other human pre-monocytic cell lines (e.g. J111 or HL60), macrophage cell lines (U937 or Mono Mac6), or human macrophage cells isolated from placenta or alveolar fluid can be used although it should be understood that for each of these human cells or cell lines a specific induction scheme for the optimal production of the product may be required. For the production of our polypeptide, the THP-1 cells were seeded at $2\times10^5$ cells/ml in roller bottles in RPMI-1640 enriched with 10% fetal calf serum. Three days later, at a cell density of $8\times10^5$ cells/ml, the cells were centrifuged and concentrated to a cell density of $10^6$ cells/ml in RPMI-1640-10% FCS enriched with 400 IU/ml of human recombinant interferon-gamma (h-rIFN-γ).

Twenty-four hours later, the cells were washed twice with serum-free medium and induced for 6 hours at a cell density of $10^6$ cells/mnl in serum free-medium with 10–15 $\mu$g/ml of LPS. Thereafter, the cells were collected by centrifugation, washed twice with icecold PBS and stored as a dry cell pellet at −70° C. until preparation of the mRNA.

2.2.2. Preparation of THP-1 mRNA and construction of a human LPS-induced, h-rIFN-γ-activated THP-1 cDNA library and screening of the library for the full-size human sequence homologous to the selected mouse cDNA fragment The in vitro induced THP-1 cells prepared as described above were used as a source of human monocytic mRNA. The polyadenylated RNA was extracted from the cells as described in section 1.2. for the PU5-1.8. cells. After quality control by sucrose gradient centrifugation, this mRNA was used for the construction of a human macrophage cDNA library in the λ ZAP II phagemid.

The human THP-1 cDNA library was constructed essentially as described in section 2.1.3. for the PU5-1.8. λZAP II cDNA library. Starting from 0.5 $\mu$g THP-1 mRNA, a human macrophage cDNA library was constructed in λZAP II of $1.5\times10^6$ independent plaques. After amplification, the library had a titer of $10^9$ pfu/ml and was stored at −70° C. in the presence of 7% DMSO.

Next, $5\times10^5$ pfu of the LPS-induced h-IFN-γ-activated THP-1 cDNA λZAP II library was screened using the $^{32}$P-labelled 990 bp EcoRI restriction fragment of the previously isolated selected mouse cDNA as radioactive probe. The cDNA was labelled to high specific activity ($\pm 8\times10^8$ cpm/$\mu$g) with $\alpha$($^{32}$P)dCTP (300 Ci/mmol; 10 mCi/ml; Amersham) using a multiprime DNA labelling procedure as provided by Amersham. The plaque lifts were prepared as described for the screening of the mouse cDNA libraries (see section 2.1.4.). The filters were prehybridized for 20–24 hours at 42° C. in a solution containing 50% deionized formamide, 4×SSPE, 1% SDS, 0.5% milk powder and 0.5 mg/ml denaturated salmon sperm DNA. Hybridization was allowed to occur for at least 48 hours at 42° C. in 47% deionised formamide, 10% dextran sulfate, 3×SSPE, 1% SDS, 0.5% milk powder using 0.5-1×$10^6$ cpms of radiolabelled probe/ml. After hybridization, a first wash was performed in 2×SSC, 0.1% SDS at room temperature for 15 minutes followed by a second wash in 1×SSC, 0.1% SDS for 20 minutes at 50° C. and a final wash in 2×SSC, 0.1% SDS for 20 minutes at 55° C. After autoradiography, phages showing positive hybridization on both plaque lifts were further plaque-purified. The longest clone we isolated contains an insert of 1487 bp (FIG. 2) and predicts an open reading frame starting from the first ATG at position 6 to position 938, specifying a polypeptide of 311 amino acids. Unlike the analogously selected LPS-induced mouse clone, the human sequence does not contain an internal EcoRI site. The 5'-end is 5 nucleotides long and will most propably be incomplete. The 3'-untranslated region is 548 nucleotides long and may be complete since an AATAAA polyadenylation signal (position 1466) is present at the end of the sequence. The 3' end region also contains the 5-TATTAT sequence resembling the cytokine consensus sequence (Caput et al., 1987), conserved between the selected human and mouse clone. The nucleotide sequence of both human and mouse share 73.8% homology (data not shown). The sequence predicted by the human clone encodes for a polypeptide with a calculated MW of 34 kDa and shows 77.4% homology with the amino acid sequence of the selected mouse clone (FIG. 5). The ten Cys residues are conserved in both sequences indicating that they may be important in the folding of the polypeptide. The absence of the putative N-glycosylation signal in the human sequence in contrast to the Asn-Leu-Thr code in the mouse sequence suggests that the human cDNA product is not glycosylated. Furthermore, the hydrophilicity plots of the human and mouse clone (FIG. 6) are very similar and, in both sequences, an eukaryotic secretory signal sequence is predicted with the most probable cleavage site between amino acid position 45 and 46. For both human and mouse, a mature product of ±30 kDa should then be found upon translocation.

3. Determination of the macrophage-specificity and LPS-inducibility of the PU5-1.8. mRNA hybridizing with the selected LPS-induced cDNA To define the degree of the LPS-inducibility of the selected gene, mRNA of uninduced and LPS-induced PU5-1.8 cells was prepared after 3 hours or 24 hours of induction. The macrophage-cell type specificity of the selected LPS-induced mouse cDNA was assessed by preparing mRNA of uninduced cells and cells treated with LPS according to the protocol followed for PU5-1.8. induction. As cell lines were selected (mouse macrophage hybridoma cells; Patent Application Innogenetics N.V. Analytical Utilisation of Phagocyte Cell Lines. 19.09.90. EP 0 159 653 B1.), EL4 cells (mouse T cell lymphoma; ATCC TIB39), mouse NSo (non-secreting mouse B cell myeloma, Kearney et al., 1979), and L929 cells (mouse fibrosarcoma, ATCC CCL1).

To this end, the cells were grown batch-wise ($10_9$ cells/batch) for 40 hours in RPMI-1640 medium enriched with 10% fetal calf serum, washed twice with serum-free medium and incubated for another 3 hours (for the LPS-induction of PU5-1.8 cells) or 24 hours in serum-free RPMI 1640, in the absence (-LPS) or in the presence of 10–15 $\mu$g/ml of LPS (+LPS). Thereafter, the cells were washed twice with icecold PBS and stored at −70° C. until preparation of the mRNA. mRNA was prepared using the NP-40 method as described in section 1.2.

All mRNA preparations were run on a denaturating formaldehyde/formamide–1.5% agarose gel (2.5 $\mu$g poly $A^+$RNA/lane) as described by Maniatis et al., (1982.) and blotted on a Nylon membrane (Hybond-N, Amersham) in 10×SSC by Northern blotting (Fourney et al. 1988). These blots were subsequently screened by hybridization using restriction fragments of the selected clone as radioactive probe (FIG. 7).

The degree of the LPS-induction of the selected gene in mouse cells was evaluated by comparison of the strength of the hybridization signals obtained with the different mRNA preparations using β-actin as internal standard. Hybridization to a mRNA of 1475 bp was detected in uninduced mouse macrophage cells, but mRNA levels were slightly increased upon in vitro treatment of the cells with LPS for three hours.

4. Isolation of the human gene containing the human cDNA of the invention

Starting from high quality genomic DNA, isolated from human spleen tissue (Maniatis et al., 1982), a human genomic library (6–8×$10^6$ independent plaques (pfu)) was constructed in the GEM11 vector (Promega) essentially as described by the supplier. From this library which has a titer of ±$10^{10}$ pfu/ml after amplification, 1.2×$10^6$ pfus were plated on MB406 (Promega) and screened for the human gene of the invention by hybridization using the full-size human cDNA insert as radioactive probe. The preparation of the filters and the pre- and hybridization conditions were as described for the homologous screening of LPS-induced PU5-1.8. λZAP II cDNA library for the isolation of the full-size mouse cDNA of the invention (section 2.1.4.). Ten positively hybridizing plaques were picked, plaque-purified, and grown for the preparation of the recombinant phage DNA. Upon further restriction mapping and Southern blotting analysis using either the full-size insert or cDNA restriction fragments located near the 5' or 3' end of the human cDNA of the invention as radioactive probe, three genomic clones (clones a, b and c) were retained for subcloning of the different SacI-fragments in the pBluescript SK(+) (Stratagene) and partially nucleotide sequencing. The 5000 bp SacI subclone of the genomic clone b contains the 5' exon fragment of the human cDNA sequence of the invention, including the ATG initiation site and extends this information until position 175 of the human cDNA were it transits in the first intron sequence by the use of a classical splice donor acceptor site. The 1500 bp SacI-subclone, present in all three isolated genomic clones, contains the second exon of the human gene of the invention from position 176 to position 561 of the human cDNA. Finally, the 3500 bp SacI-subclone contains the third and fourth exon of the gene, respectively ranging from position 562 to 621 and from position 622 to the end of the human cDNA including the 3'-end-located AATAAA polyadenylation site.

5. Expression of the mouse polypeptide of the invention in *E. coli* cells

The DNA sequence coding for a polypeptide, or part of it, can be linked to a ribosome binding site which is part of the expression vector, or can be fused to the information of another protein or peptide already present in the expression vector.

In the former case, the information is expressed as such and hence devoid of any foreign sequences (except possibly for the amino terminal methionine which is not always removed by *E. coli*). In the latter case the expressed protein is a hybrid or a fusion protein.

Various methods and materials for preparing recombinant vectors, either of plasmid, bacteriophage or cosmid nature, the procedures for transformation or infection in different host cells and expressing polypeptides and proteins are described by Panayatos (1981) and by Old and Primrose (1981) and are well known to those skilled in the art.

A suitable vector is plasmid pmTNF-MPH (Innogenetics). It contains the tetracycline resistance gene and the origin of replication of pAT153 (Twigg and Sherratt (1980) (obtainable from Biores B. V., Woerden, The Netherlands), the PL promoter up to the MboII site in the N gene 5' untranslated region, followed by a synthetic ribosome binding site (see sequence data) and the information encoding the first 25 amino acids of mTNF (except for the initial Leu which is converted to Val). This sequence is, in turn, followed by a polylinker sequence encoding six consecutive His residues downstream of which several proteolytic sites (formic acid, CNBr, kallicrein and *E. coli*, protease VII sensitive sites) are incorporated. Each of these proteolytic sites is at the DNA level accessible by a unique restriction site. The presence of the $[His]_6$ sequence in the fusion peptide allows $Ni^2$+-imrobilized metal affinity chromatography (IMAC) based purification of the recombinant protein of interest. Downstream from the polylinker, translational stop codons are present ib the three possible reading frames which in turn are followed by the *E. coli* trp terminator of transcription (synthetic) and the rrnBT1T2 terminator of transcription (originating from pKK223-3; Pharmacia). The restriction and genetic map of this plasmid is represented in FIG. 8*a*. The total nucleic acid sequence of this plasmid is represented in FIG. 8*b*.

DNA of the pmTNF-MPH-PU1280-Eco47III containing the mouse nucleotide sequence of the invention from the Eco47III restriction site at position 318 to the EcoRI cloning site (position 1364), cloned in the proper orientation into the StuI site of the pmTNF-MPH, a technique well known to those skilled in the art, was transformed into *E. coli* strain K12Λ A H (ATCC 33767) using standard transformation procedures. However, the growth temperature of the cultures is reduced to 28° C. and the heat shock temperature is raised to 42° C. A culture of K12D H harbouring pmTNF-MPH-PU1280-Eco47III, grown overnight in Luria broth a 28° C. with rigorous shaking in the presence of 10 μg/ml tetracycline, was inoculated into fresh Luria broth containing tetracycline (10 μg/ml) and grown to an optical density of 0.2 measured at 600 nm under the same conditions as for the overnight culture. At this density of bacterial growth, half of the culture was shifted to 42° C. to induce expression while the other half remained at 28° C. as a control. At several time intervals aliquots were taken which were extracted with one volume of phenol equilibrated against M9 salts (0.1% ammonium chloride, 0.3% potassium dihydrogen phosphate, 1.5% disodium hydrogen phosphate, 12 molecules of water) and 1 % SDS. At the same time the optical density at 600 nm of the culture is measured. The proteins are precipitated from the phenol phase by addition of two volumes of acetone and storage overnight at −20° C. The precipitate is pelleted (Biofuge A, 5 min, 13000 rpm, room temperature), air dried, and dissolved in a volume of Laemnli (1970) sample buffer (+β-mercaptoethanol) according to the optical density of the culture sample and boiled for 3 minutes. Samples were then run on a SDS polyacrylamide gel (12.5%) according to Laemmli (1970). Temperature induction of pmTNF-MPH-PU1280-Eco47III was monitored by both Coomassie Brilliant Blue (CBB) staining and immunoblotting.

For CBB staining, the gel was first treated for at least 1 hour at 4° C. with a 10% trichloroacetic acid (TCA) solution and subsequently immersed in a 1/10 diluted CBB staining solution (0.5 g CBB-R250 (Serva) in 90 ml of methanol: $H_2O$ (1:1 v/v) and 10 ml glacial acetic acid) and left for about one hour on a gently rotating platform. After destaining in 30% methanol-7% glacial acetic acid (two to three washes of about 30 min each), protein bands were visualized and scanned with a densitometer (for instance Ultroscan XL Enhanced Laser sensitometer, Pharmacia LKB).

For immunoblotting the proteins were transferred onto Hybond C membranes as described by Towbin et al. (1979). After blotting, proteins on the membrane were temporarily visualized with Ponceau S (Serva) and the position of the molecular weight markers was indicated. The stain was then removed by washing in $H_2O$.

Aspecific protein binding sites were blocked by incubating the blots in 10% non-fat dried milk for about 1 hour on a gently rotating platform. After washing twice with NT buffer (25 mM Tris Cl pH 8.0; 150 mM NaCl) blots were incubated with monoclonal anti-hTNF antibody (1/10) which cross-reacts with mTNF (Innogenetics No. 17F5D10) for at least 2 hours on a rotating platform. After washing twice with NT buffer +0.02% Triton X100, blots were incubated for at least 1 hour with the secondary antiserum which was alkaline phosphatase-conjugated rabbit anti-mouse immunoglobulins (1/500; Sigma). Blots were washed again twice with NT buffer +0.02% Triton-X100 and then visualized with nitro blue tetrazolium (NBT) and 5-bromo-4-chloro-3-indolyl-phosphate (BCIP) from Promega under conditions recommended by the supplier.

After induction of K12 H cells transformed with pmTNF-MPH-PU1280-Eco47III, a band of about 34 kDa appeared on CBB stained gels, which represents about 15% of total synthesis (FIG. 9). The fusion product between TNF and the selected gene product reacts clearly with anti-hTNF-monoclonal antibody (No. 17F5D10) on immunoblot.

6. Transient expression of the mouse and the human sequences in COS1 cells

The mouse cDNA of the invention was introduced into an expression vector comprising the SV40 origin of replication and part of the SV40 late region containing the strong SV40 late promoter and enhancer sequence followed by a multilinker sequence which is flanked by donor and acceptor splice sites of the late 16S mRNA and the polyadenylation signal of the SV40 region (pSVL)(Fig. 10). This type of expression vector was originally described by Gheysen et al. (1982).

The mouse cDNA sequence of the invention was introduced according to methods known to those skilled in the art into the multicloning site of this expression plasmid as a HindIII-EcoRV (multicloning site of pSP73) DNA fragment isolated from the so-called plasmid pSP73-PU1280 which contains the mouse cDNA sequence as a SphI-EcoRI fragment. Transfection of the COS1 cells (Gluzman et al., 1981)(ATCC CRL 1650) with the resulting plasmid pSV-PU1280-HdIII was done according to an optimized DEAE-transfection protocol (McCutchan and Pagano, 1968). In case of in vivo labelling of the cells with $^{35}$S-methionine, the transfection of the cells was followed by two washes with methionine-free medium (DMEM or RPMI-1640) without serum, a starvation period of one hour in the same medium, and subsequent incubation in 1 ml medium per $10^6$ cells supplemented with $^{35}$S-methionine for 24 hours (100 μCi/ml $^{35}$S-methionine; 1150 Ci/mM/ml; 10m Ci/ml).

Proteins secreted in conditioned medium of transfected cells were TCA-precipitated and analyzed on 12.5% Tricine-SDS-polyacrylamide gels (Schägger and von Jagow, 1987) or by 2-dimensional nonequilibrium pH gel electrophoresis (NEPHGE) as described by Van Fleteren et al. (1992). Production of the protein of the invention was demonstrated by either CBB staining (as recommended by the supplier, Serva), immunoblotting, or fluorography (Enhance-Dupont). For immunoblotting, proteins were electroblotted onto nitrocellulose membranes (Sartorius) and, after blocking of aspecific protein binding sites with Tween-20 (Sigma) and 3% BSA (Sigma), the membranes were incubated with polyclonal antiserum raised against the mTNF-MPH-cDNA fusion protein (1/500) (section 9.). As a second antibody, alkaline phosphatase-conjugated mouse anti-rabbit immunoglobulin (1/1000, Sigma) was used and subsequent visualization was performed with nitro blue tetrazolium (NBT) and 5-bromo-4-chloro-3-indolyl-phosphate (BCIP) (Promega).

Transfection of COS1 cells with the pSV-PU1280-HdIII expression plasmid results in production and secretion of an extra protein with a molecular weight (MW) of approximately ±30 kDa (non-reduced) or ±34 kDa (reduced). The reduced form of the protein (±34 kDa) was only detectable by immunoblotting with mTNF-MPH-mcDNA antiserum, because a COS1 cell-specific protein masks the position of the 34 kDa protein. The calculated MW of the mature polypeptide coded for by the cDNA of the invention is 29.9 kDa. The higher MW of the protein produced in COS1 cells is due to glycosylation of the mouse protein as indicated by in vitro transcription-translation experiments (results not shown) and from results of the Vaccinia expression (see below).

On 2D-NEPHGE (non-reduced) the protein appears as a triple peptide spot (due to secondary modifications) with a MW of ±30 kDa and a pI of approximately 5.5 to 6.0 (FIG. 11).

To allow amino acid sequence confirmation of the 30 kDa protein secreted by pSV-PU1280-HdIII transfected COS1 cells, preparative amounts (±2 liters) of the COS1 conditioned medium were prepared and the ±30 kDa triple protein spot was excised from preparative Coomassie R stained non-reducing 2D-NEPHGE gels. The different spots were concentrated according to Rasmussen et al. (1991) and digested with 2% formic acid at 110° C. for 4 hours (Van Fleteren et al., 1992). Peptides were separated on an aquapore butyl 7 $\mu$ (Brownlee-10 cm×2.1 mm) column and peptides AH20 and AH27 (FIG. 12) were sequenced using an Applied Biosystem 477A protein sequencer. The resulting sequences were 100% homologous to the polypeptide sequence predicted from the mouse cDNA sequence of the invention.

In an analogous manner to the construction of the vector containing the mouse sequence, the human homologue was inserted into the vector pSVL as an EcoRI (cDNA cloning sites) DNA fragment. Transfection of COS1 cells with the resulting pSV-T1200 expression plasmid results in production and secretion of a protein with a MW of ±27 kDa (non-reduced) or +30 kDa (reduced). On non-reducing 2D-NEPGHE the protein appears as a protein spot with a MW of ±27 kDa and a pI of ±6.0 to 7.0, without apparent indication of secondary modifications, consistent with the lack of a N-glycosylation site in the human amino acid sequence (FIG. 13).

7. Expression of the selected mouse cDNA of the invention in a baculovirus expression system The baculovirus expression vector system is a highly efficient eukaryotic expression vector for producing large amounts of selected polypeptides in a suitable environment for posttranslational modifications. This helper-independent recombinant virus vector has produced recombinant protein at levels ranging from 1 to 500 mg/liter (Smith et al., 1983; Smith et al., 1985).

The mouse cDNA of the invention was inserted into the intermnediate transplacement vector pACYM1 (Matsuura et al., 1987) according to methods known to those skilled in the art.

The mouse cDNA of the invention was introduced as a BamHI fragment, derived from pSV-PU1280-HdIII, into the BamHI insertion site of the pACYM1 vector downstream from the strong baculoviral polyhedrin promoter. The resulting transfer vector was cotransfected with wild type baculovirus DNA (*Autographa californica* (mono) nuclear polyhedrosis virus AcMNPV) into *Spodoptera frugiperda* cells (Sf9 ATCC 1711) using a modification of the calcium phosphate precipitation technique (Graham, 1973) adapted for insect cells. Recombinant virus was selected visually.

Infection of Sf9 cells with recombinant baculovirus containing the mouse cDNA of the invention results in production and secretion of an extra protein with a MW of ±28 kDa (non-reduced) or ±32 kDa (reduced) as determined by SDS-PAGE (fluorography and/or innmunoblotting) (FIG. 14). Upon analysis of condition medium on 2D-NEPGHE, the protein appears as a spot with MW ±28 kDa (non-reduced), ±32 kDa (reduced) and pI ±5.5 to 6.0. The difference in MW between the polypeptide of the invention produced and secreted by either transient expression in COS1 cells or by recombinant baculovirus-infected Sf9 cells is due to differences in secondary modifications (glycosylation) of the polypeptide in the two expression systems, as could be shown by glycosylation pattern analysis using different glycosidases (results not shown).

8. Expression of the mouse and human cDNA of the invention in a vaccinia expression system The vaccinia virus expression system is considered one of the more promising ways of producing significant amounts of correctly processed and modified eukaryotic proteins in manmmalian cells. The wide host range of the virus and its ability to infect a variety of vertebrate cell lines including macrophages makes it an especially interesting tool to express macrophage-specific proteins (Moss and Flexner, 1987).

Both the mouse and human cDNA of the invention were introduced into the vaccinia genome using the intermediate transplacement vector pATA18 (Stunnenberg et al., 1988). The cDNA of the invention was introduced as a BamHI fragment, derived from pSV-PU1280-HdIII or pSV-T1200, into the BamHI insertion site of the pATA18 vector (Stunnenberg et al., 1988) downstream from the vaccinia 11 K late promoter according to methods well-known to those skilled in the art. The resulting transfer vectors (pATA-PU1280-HdIII for the mouse cDNA, pATA-T1200 for the human cDNA) were transfected by the calcium phosphate method into RK13 cells (ATCC CCL 37.) defective for the TK gene (TK-) after prior infection with wild-type vaccinia virus. Recombinant progeny virions containing the cDNA of the invention were chosen using deoxyuridine selection (BrDU). The technology used is well-known to those skilled in the art.

In comparison with wild-type virus infected HeLa cells (ATCC CCL 2.), infection with recombinant vaccinia virus containing the mouse cDNA of the invention results in production and secretion of an extra protein with a MW of +30 kDa (non-reduced) and ±34 kDa (reduced) as determined by SDS-PAGE. Upon analysis of the conditioned medium produced by these cells on reducing 2D-NEPHGE the protein appears as a triple peptide spot with MW of +34 kDa and a pI of 5.5 to 6.0 (FIG. 15).

Infection of cells (HeLa) with recombinant vaccinia virus containing the human cDNA of the invention results in the secretion of a protein with a MW of ±27 kDa (non-reduced) and ±30 kDa (reduced). On 2D-NEPHGE, the protein migrates as a peptide spot with a MW of ±30 kDa and a pI of 6.0–7.0 (FIG. 16).

9. Production of polyclonal antibodies against the mouse and human polypeptides of the invention A bacterially produced fusion protein between mTNF and the mouse polypeptide of the invention containing 6 histidine residues at the fusion position (see section 5.) was prepared by starting from one liter culture of transformed bacteria (pmTNF-MPH-PU1280-Eco47III). Bacterial expression products were sulfonated prior to separation by incubating the bacterial pellet in 8M urea, 20 mM Tris-HCl pH 7.0, 1 mM $CuSO_4$, 130 mM $Na_2S_2O_8$ and 610 mM $Na_2SO_3$. Twenty-four hours later the mixture was dialyzed against 7 M urea, 30 mM Tris-HCl pH 7.2 and loaded on a MONO Q-Sepharose column (Pharmacia) in the same buffer. The material was eluted from the matrix using a linear salt gradient up to 1M NaCl and resulting fractions were tested by SDS-PAGE and immunoblotting using anti-TNF antiserum. The fractions containing the fusion protein of interest (fractions 48 to 53) eluting from the column between 250 and 350 mM NaCl were pooled and further purified by $Ni^{2+}$-immobilized metal affinity chromatography (IMAC), according to the manufacturer's instructions. After elution with 100 mM imidazol the anti-TNF immunoreactive fusion protein was dialyzed against 7M urea, 30 mM Tris-HCl pH 7.2 and subsequently used for immunization of rabbits. Technology used is well known to those skilled in the art.

The resulting antiserum (anti-mTNF-MPH-mcDNA) was tested for specific (cross-) reaction with the mouse and human polypeptide of the invention both by immnunoblotting (detection of the denatured form of the polypeptide) and immunoprecipitation (detection of the native soluble form of the polypeptide). Several examples of the detection by immunoblotting have already been demonstrated (see above). For immunoprecipitation, 850 $\mu$l of $^{35}$S-methionine-labelled conditioned medium of COS1 cells transfected with pSV, pSV-PU1280-HdIII, or pSV-T1200 was incubated with 30 $\mu$l of antiserum. After reaction, the immunoglobulins were selectively precipitated with 30 $\mu$l of a 50% suspension of proteinA glass beads using the procedure recomnmended by the supplier (Porton). After binding, the supernatant was discarded and the beads were washed with PBS/0.05% Tween 20/0.01% BSA to remove the aspecific binding proteins. Subsequently, specific antibody binding proteins were eluted by boiling for 5 min in 30 $\mu$l 1.5×Laemili sample buffer and analyzed by SDS-PAG-fluorography.

By immunoblotting the anti-mTNF-MPH-mcDNA antiserum recognizes the polypeptide of the invention produced in COS cells (30 kDa/34 kDa), recombinant baculovirus-infected Sf9 cells (28 kD a/32 kDa) as well as a 30 kDa/ 34 kDa protein secreted in the conditioned medium of the macrophage cell line PU5-1.8 (FIG. 17). The antiserum also cross-reacts with the human analogue of the polypeptide of the invention produced and secreted by COS1 cells. In addition the antiserum is also able to immunoprecipitate the native form of the mouse polypeptide of the invention as produced in COS1 cells upon transfection with pSV-PU1280-HdIII (FIG. 18).

Based upon computer prediction of the antigenicity of different peptides coded for by the human cDNA of the invention, a C-terminal peptide of 29 amino acids (position 283 to 311: GCAPRFKDFQRMYRDAQERGLNPCEVGTD) was chemically synthesized according to methods known to those skilled in the art (Atherton et al., 1989), coupled to hemocyanin essentially as described (Harlow, 1988), and injected into rabbits using classical immunization schemes. The resulting antiserum was tested in immunoprecipitation and immunoblotting experiments mainly as described earlier. It recognizes the human polypeptide of the invention secreted by pSV-T1200-transfected COS1 cells (see above) as well as the product of the human macrophage cell line Mono Mac 6 either secreted constitutively or after activation. Furthermore, the antiserum was also able to imnmunoprecipitate the native form of the protein as it recognizes the polypeptide of the invention secreted by pSV-T1200-transfected COS1 cells.

10. N-glycosylation pattern of the recombinant and native mouse polypeptide of the invention In order to study the N-glycosylation patterns of the recombinant mouse polypeptide of the invention produced in different expression systems with the native polypeptide secreted by PU5-1.8 cells, studies using the enzymatic removal of glycosylic residues by N-glycosidase F (E.C. 3.2.1.96) were performed. Therefore, conditioned medium (CM) of cells secreting the mouse polypeptide of the invention or their respective negative controls were treated with N-glycosidase F under the optimal conditions as described by the manufacturer. Condition medium was then analyzed by Western blotting using the anti-mTNF-MPH-mcDNA fusion protein polyclonal antiserum.

As was described, the glycosylated form of the protein of the invention has the same MW (±34 kDa-reduced) when secreted by PU5-1.8 cells, COS1 cells, or recombinant vaccinia virus-infected cells. The recombinant baculoviral produced protein has a slightly lower MW (±32 kDa-reduced).

After N-deglycosylation, both the native protein and the three eukaryotic expression systems described, shift to an apparent MW of ±29 kDa (reduced), corresponding to the theoretical MW calculated for the mature unglycosylated polypeptide of the invention (FIG. 19). These data demonstrate that the lower MW of the protein produced by insect cells results from a less complex N-glycosylation pattern of the protein. According to the literature, insect cells can carry out N-glycosylation, but the addition of high mannose to complex N-linked oligosaccharides does not appear to take place (Luckow and Summers, 1988).

Analogous studies were performed on the human analogue of the protein of the invention. No evidence for any N-glycosylation event was demonstrated in accordance with the lack of a N-glycosylation consensus sequence in the human protein sequence.

11. Purification of the mouse recombinant protein of the invention Conditioned medium (600 ml) of COS1 cells transfected with the cDNA of the invention as described in section 6. was collected after 48 h and filtered over a 0.22 $\mu$m filter to remove cell debris. A typical purification started from 600 to 1000 ml of COS1 transfection medium. To this mgCl2 and dextranesulphate 500.000 (Pharmacia, Uppsala, Sweden) was added to a final concentration of 60 mM and 0.02%, respectively. After 1 h incubation at 4° C. the precipitate was pelleted by centrifugation (12.000 g, 30 min., 4° C.). The supernatant fraction, containing the mouse polypeptide of the invention was dialysed against 50 mM Hepes pH 7.0, 4 mM EDTA, adjusted to pH 8.0 and located at a flowrate of 0.5 ml/minute on a 4 ml Phenylboronate agarose (PBA 30, Amicon, Mass., USA) column equilibrated in 50 mM Hepes pH 8.5. The mouse polypeptide of the invention was eluted from the matrix by 100 mM Sorbitol.

The Sorbitol eluated peak (±25 ml) is then passed at a flowrate of 0.5 ml/minute over a 1 ml FPLC Mono Q anion exchange column (Pharmacia) equilibrated in Hepes pH 8.5 and eluted with a linear salt gradient of 0 to 1M NaCl at a flowrate of 1 ml/minute. The mouse polypeptide of the invention eluted at 125 mM NaCl in a total volume of ±10 ml.

The eluate was concentrated about 40 fold by Centricon 10.000 (Amicon) and loaded batchwise (3 times 0.25 ml) on a SMART Superdex 75 gelfiltration column (Pharmacia) equilibrated against PBS. The highly purified mouse polypeptide of the invention (>98% pure) eluted at a molecular weight of 34 kDa, well resolved from a higher molecular weight peak containing aggregated mouse polypeptide of the invention and higher molecular weight contaminants.

TABLE III

| purification steps | sample volume (ml) | protein conc. ($\mu$g) |
|---|---|---|
| COS1 conditioned medium | 600 | 23.000 |
| $Mg^{++}$/dextranesulphate precipitate | 600 | N.D. |
| PBA Sorbitol eluate | 25 | 750 |
| Mono Q eluate | 10 → 0.25 | 45 |
| Superdex 75 gelfiltration | 3 × 0.25 or 0.75 | 15 |

12. Biological activities of the mouse recombinant protein of the invention 12.1. Proliferative effect of the mouse polypeptide of the invention on mouse thymocyte populations Thymocytes were isolated from 3-week-old C3H mice (IFFA CREDO, France), and seeded in microtiter wells at $5 \times 10^5$ cells per well in RPMI-1640 5% FCS, 2 $\mu$g/ml PHA, and two-fold serial dilutions of the polypeptide of the invention alone or in combination with two-fold serial dilutions of the mouse cytokines IL-1, IL-2, IL4 or IL-6, or combinations of these (start concentration in the first well being 400 U/ml). Seventy-two hours later the cells were labelled with $^3$H-thymidine (1 $\mu$Ci/well) and harvested after 24 hours for counting in a liquid scintillation counter. The mouse polypeptide of the invention when added alone elicits a thymocyte growth-proliferative effect in the presence of the lectin PHA. When tested in combination with the different cytokines, especially in the presence of IL-4, a growth-enhancing effect towards control values (counts incorporated in the presence of IL-4 alone) could be observed (FIG. 20). When testing combinations of IL-4 with other T-cell interacting cytokines (IL-1, IL-2 or IL-6) and serial dilutions and/or constant concentrations of the mouse polypeptide of the invention, a similar invention- specific growth-proliferative effect could be observed in varying degrees for the combinations of IL-4 and IL-1 or IL-2, but not with IL-6.

12.2. In vitro activity of the polypeptide of the invention on the mitogenic and allogeneic responses of lymph node and splenic cell populations When properly activated, macrophages secrete monokines such as TNF-α, IL-1-α, IL-1-β and IL-6 that provide accessory signals for the stimulation of peripheral T cells. Similarly, certain T-cell derived lymphokines such as IFN-γ also play an accessory role in the activation of T cells. The mouse polypeptide of the invention was tested for its function as an accessory signal in T-cell activation either alone or in combination with other cytokines (IL-1, IL-6 or IFN-γ) always in the presence of the lectin PHA or ConA.

When tested on ConA activation of lymph node cells (LNC) with and without IL-1, IL-6 or IFN-γ (each time 100 U/ml), the polypeptide of the invention exhibits an additive growth-stimulating effect and this effect is significantly increased when tested in combination with IFN-γ. This effect is not observed with the accessory molecules IL-1 and IL-6.

When the growth proliferative effect of the polypeptide of the invention was tested on the same cell populations (LNC and SPC) but now combined with the lectin PHA instead of with ConA, a similar growth- proliferative activity was recorded upon adding the polypeptide of the invention. This effect also synergized with IFN-γ.

T cells were depleted of accessory cells by fractionation on a nylon-wool column, well known to those skilled in the art. The nonadherent cell fraction represents the T-cell population while the accessory are retained by the matrix. CD4+ and CD8+ T cell subpopulations are isolated from the nylon-wool non-adherent fraction by magnetic cell sorting (MACS) separation using either anti-CD4+ or anti-CD8+ antibodies, a technique well known to those skilled in the art. The total LNC T-cell population, the nylon-wool nonadherent T cells, CD4+T cells and CD8+ T cells were stimulated with ConA either as such or supplemented with 5% accessory cells (mice peritoneal exudate cells). The combined effect of the mouse polypeptide of the invention with IFN-γ was tested on the ConA-induced proliferations of the total unfractionated lymph node cell population or the nylon-wool nonadherent fraction or MACS purified CD4+ or CD8+T-cell subpopulations (Table II). On the total LNC population, a significant enhancement of the proliferative response by the combined action of the mouse polypeptide of the invention and IFN-γ could be measured, while no effect on growth stimulation could be observed on the nylon-wool nonadherent T-cell population, or on the MACS-purified CD4+ or CD8+ T cells. However, upon addition of an accessory cell population (5% of peritoneal exudate cells (PEC)) to the nylon wool nonadherent subpopulation, the proliferative effect of the mouse polypeptide of the invention was partially restored. The restoration of the enhancing effect was not observed when supplementing the purified CD4+ or CD8+ T cells with 5% PEC.

Similar experiments were performed with spleen (SPC) cell populations except that in these experiments the MACS-purified CD4+ and CD8+ T-cell populations were not included. The mouse polypeptide of the invention again demonstrated a co-stimulatory effect on the T-cell growth proliferation that requires the presence of accessory cells.

On both cell populations (LNC and SPC), similar results could be recorded when using the lectin PHA instead of ConA.

The polypeptide of the invention together with IFN-γ enhances the mitogenic response of T cells. This enhancing effect requires the presence of accessory cells such as macrophages.

Table II hereunder relates to the effect of the mouse polypeptide of the invention and IFN-γ on the ConA-induced proliferation of LNC populations. T cells were depleted of accesory cells by fractionation on nylon wool column (nonadherent fraction represents the T-cell population), essentially as described by Julius et al. (1973). CD4+ and CD8+ T cell subpopulations were isolated by magnetic cell sorting (Miltenyl et al., 1990). T cells, CD4+ T cells and CD8+ T cells (at a cell concentration of $2 \times 10^5$ cells/ml) were stimulated for 24 hours with 2.5 $\mu$g/ml of ConA either as such or supplemented with 5% accessory cells (peritoneal exudate cells). The latter were prepared by injecting mice intraperitoneally with 5 ml of DMEM-5% glucose followed by recuperation of the injected material together with the peritoneal cell population. Twenty-four hours later the cells were pulsed with $^3$H-thymidine (1 $\mu$Ci/ml) for another 18 hours and harvested. The combined effect of the conditioned medium of the COS1 -expressed mouse polypeptide of the invention (rec prot) or of the CM of pSVL-transfected COS1 cells (pSVL) with 100 IU of IFN-γ was tested on the ConA-induced proliferations of unfractionated LNC populations or nylon wool nonadherent CD4+ or CD8+ subpopulations. The ratio 1/10 or 1/2 represent a one-to-ten or one-to-two dilution of the gel filtration purified material (see section 6) in the bioassay test medium.

TABLE II

| | ConA-induced proliferation | | |
|---|---|---|---|
| Cell population | cpms | Δcpms (-control) | Δcpms (-control-IFN-γ) |
| LNC(total) | 20 | — | — |
| +IFN-γ | 46 | 26 | — |
| +IFN-γ+ pSVL (1/10) | 57 | 37 | 11 |
| +IFN-γ + rec prot (1/10) | 71 | 51 | 25 |
| +IFN-γ + pSVL (1/2) | 84 | 64 | 38 |
| +IFN-γ + rec prot (1/2) | 110 | 90 | 64 |
| LNC(nylon nonadherent) | 2 | — | — |
| +IFN-γ | 17 | 15 | — |
| +IFN-γ + pSVL (1/10) | 17 | 15 | 0 |
| +IFN-γ + rec prot (1/10) | 18 | 16 | 1 |
| LNC(nylon nonadherent) + PEC | 11 | — | — |
| +IFN-γ | 11 | 0 | — |
| +IFN-γ + pSVL (1/10) | 18 | 7 | 7 |
| +IFN-γ + rec prot (1/10) | 31 | 20 | 20 |
| LNC(CD4+) | 4 | — | — |
| +IFN-γ | 7 | 3 | — |

TABLE II-continued

| Cell population | ConA-induced proliferation cpms | Δcpms (-control) | Δcpms (-control-IFN-γ) |
|---|---|---|---|
| +IFN-γ + pSVL (1/10) | 8 | 4 | 1 |
| +IFN-γ + rec prot (1/10) | 10 | 6 | 3 |
| Effect of the mouse polypeptide of the invention and IFN-γ on the ConA-induced proliferation of LNC subpopulations. | | | |
| LNC(CD4+) + PEC | 27 | — | — |
| +IFN-γ | 24 | 0 | — |
| +IFN-γ + pSVL (1/10) | 24 | 0 | 0 |
| +IFN-γ + rec prot (1/10) | 26 | 0 | 0 |
| LNC(CD8+) | 0.3 | — | — |
| +IFN-γ | 1.2 | 0.9 | — |
| +IFN-γ + pSVL (1/10) | 2.2 | 1.9 | 1 |
| +IFN-γ + rec prot (1/10) | 2.6 | 2.3 | 1.4 |
| LNC(CD8+) + PEC | 16 | — | — |
| +IFN-γ | 12 | 0 | — |
| +IFN-γ + pSVL (1/10) | 14 | 0 | 0 |
| +IFN-γ + rec prot (1/10) | 11 | 0 | 0 |

12.3. Effect of the polypeptide of the invention on the acetyl-LDL uptake of mouse foam cells J774 (ATCC TIB 76) are mouse monocytic cells that can be differentiated in vitro to mouse foam cells by treatment with acetylated low density lipoproteins (acetyl-LDL), a process that can be followed by measuring the intracellular acetyl-LDL content and the cholesterol esterification. Preincubation or co-incubation of the mouse monocytic J774 cell line with the mouse polypeptide of the invention before of during treatment with acetyl-LDL had an effect on the uptake of acetyl-LDL by the cells. Treatment of the J774 cells for 24 hours with the mouse polypeptide of the invention either before or during the treatment with acetyl-LDL increases the amount of total cholesterol in the cells. This can no longer be observed after 4 hours treatment indicating that the mouse polypeptide of the invention modulates the speed of cell uptake of acetyl-LDL. This effect could be due to an up-regulation of the expression of the acetyl-LDL scavenger receptor on the J774 cells or by another interaction of the mouse polypeptide of the invention with acetyl-LDL or with the J774 cell membrane. Other cytokines such as IL-1, GM-CSF and M-CSF have been described to have an effect on the cholesterol metabolism of the macrophages (Ishibashi et al., 1990). For M-CSF it has been demonstrated that the preincubation of the macrophage cells with this cytokine enhanced the uptake and degradation of acetyl-LDL in a dose-dependent manner. The polypeptide of the invention could act either directly on the macrophage cell or indirectly by inducing M-CSF or another of the above-mentioned cytokines or another yet unknown cytokine having a direct effect on the acetyl-LDL uptake of the macrophage cell.

12.4. Growth inhibitory effect of the mouse polypeptide of the invention on the colony stimulating activity of Wehi-3 conditioned medium Colony-stimulating activity of bone marrow cells can be tested in vitro using a standard CFU-GEMM agarose assay (Metcalf and Johnson, 1978) well known to those skilled in the art. When enriched with the suitable growth factor (IL-3, GM-CSF, G-CSF, M-CSF, erythropoietin), this assay system allows the proliferation of a large variety of clonal cell populations from a total bone marrow cell mixture including colonies of granulocytes, macrophages, megakaryocytes, eosinophils, basophils, mast cells and, if the assay is conducted in the presence of erythropoietin, even normoblasts and red cells (Bazil et al., 1983). When the mouse polypeptide of the invention is added to the bone marrow cell mixture, no cell colonies are formed using the CFU-GEMM assay either in the absence or presence of erythropoietin indicating that the protein itself does not have any intrinsic colony- stimulating activity on this cell population. When combined with conditionned medium of Wehi-3 (ATCC TIB68) cells, described as containing an active concentration of mouse IL-3 (Lee et al., 1982) (among other cytokines such as GM-CSF, G-CSF, IL-1, etc.) allowing the growth of all the different cell colonies mentioned above, the CSF activity of the conditioned medium was significantly reduced. This demonstrates that the mouse polypeptide of the invention exerts an inhibitory or antagonistic effect on the CSF potential of the conditioned medium of Wehi-3 cells by interacting either indirectly or directly with a single cytokine or a mixture of synergizing cytokines present in the protein mixture.

12.5. Osteoblast growth-promoting effect of the mouse polypeptide of the invention using rat femur pre- and osteoblast enriched cell populations The continuous remodelling of bone occurs as a coordinated succession of cell-mediated events involving an initial period of osteoclastic resorption followed by osteoblast-mediated bone formation. This process is highly regulated by different systemic factors and by cytokines.

Osteoblast proliferative activity of the mouse polypeptide of the invention was tested using femurs of 3-week-old male WISTAR rats. Osteoblastic cells were isolated from the cleaned and flushed femur bones by 5 sequential digestions of 30 minutes each with an enzyme mixture containing collagenase (Sigma), hyaluronidase (Sigma) and DNase (Boehringer Mannheim) at final concentrations of 0.5, 0.5 and 0.1 mg/ml, respectively. Subsequently, the cell pools of the first two and the last three enzymatic digestions were treated separately and are referred to as pre-osteoblasts and osteoblasts, respectively. Cell pools were washed in Ham F12-DMEM- Hepes (1:1, v/v) (HD) and plated in HD-10% FCS for 6 days. Thereafter, the osteoblastic cells were collected by trypsinization and plated in 48-well plates at 40,000 cells per well in HD-1% FCS. Twenty-four hours later, the cells were washed and the medium was replaced by HD-1% BSA for another 24 hours after which serial dilutions of the polypeptide of the invention were added. Nineteen hours later the cells were labelled with $^3$H-thymidine (1 $\mu$Ci/well) for 6 hours and harvested for counting. The results (FIG. 21) point to a specific osteoblast proliferative-inducing activity of the composition containing the polypeptide of the invention.

12.6. Trypanocidal activity of the mouse polypeptide of the invention

The trypanocidal activity of the mouse polypeptide of the invention was measured using the following in vitro assay system: 2.10$^6$ /ml purified bloodstream forms of *Trypanosoma brucei brucei* or *T. brucei rhodesiense*, isolated 1 day before the first in vivo peak of parasitaemia, were incubated for 5 h in phosphate buffered saline (PBS), 1 % glucose, 1

% normal mouse serum (incubation medium) at 37 ° C. with various concentrations of the recombinant mouse polypeptide of the invention. After 5 h of incubation, the number of living (=moving) parasites was assessed (counting chamber) and compared to the control wells in which only incubation medium was added to the trypanosomes. The spontaneous mortality in the control wells after 5 h was always lower than 10 %. The *T. brucei brucei* AnTat 1.1 (EATRO 1125) pleomorphic bloodstream form was provided by Dr. N. Van Meirvenne of the Institute for Tropical Medicine, Antwerp, Belgium, and the *T. brucei rhodesiense* Trp11 pleomorphic bloodstream form was provided by Dr. E. Bajyana Songa (Dept. Molecular Biology, Free University of Brussels, Belgium).

Incubation of purified bloodstream forms of *T. brucei brucei* and *T. brucei rhodesiense* for 5 h with the recombinant mouse polypeptide of the invention results in the mortality of a part of the parasites: 50% of the animals are killed with 50 ng/ml of recombinant mouse polypeptide. In the same assay, 500 pg/ml of recombinant human or mouse TNF-α cause a 50% mortality of *T. brucei brucei* or *T. brucei rhodesiense* (data not shown).

12.7. The mouse polypeptide of the invention enhances the mobility of LAK cells.

Lymphocytes activated killer (LAK) cells can be generated from murine spleen cells by stimulation with IL2. The mobility of the cells can then be tested by the use of a Transwell system (3 μm membrane, Costar) wherein the migration of the cells trhough the membrane is measured after a fixed incubation method.

To test the effect of the mouse polypeptide of the invention on the mobility of LAK cells, F1 mice (Balb/c×C57b1) were sacrificed by cervical dislocation, and the spleen was removed aseptically, crushed with a syringe plunger and pressed through a syringe with 18 G and a 23 G needle into a petri-dish containing DMEM. Cell debris was removed by sedimentation, and the resulting cell suspension was depleted of B cells and macrophages by passing through a nylon wool column. Thereto, 0.4 g of nylon wool (Wako, Japan) was put in a 10 ml syringe and autoclaved. Just before applying the cells, the column was washed with DMEM-5 % FCS and incubated for 1 h at 37° C. The spleen cells were resuspended in DMEM-5% FCS at a cell concentration of $10^8$ cells/ml, loaded on the column (2 ml/run) and incubated for 45 min at 37° C. Subsequently, the nonadherent cell fraction (these are all the non-B and non-macrophages cells) was recuperated from the column by washing the matrix with 10 ml DMEM-5% FCS. The cells were collected by centrifugation, wasged and resuspended at $10^6$ cells/ml in RPMI1640-10% FCS-50 μM β-mercaptoethanol in the presence of 1000 U/ml of IL2 and 25 ng/ml of the mouse polypeptide of the invention (LAK+IL2+30 kDa) for 7 days. Northern blotting analysis as well as cPCR studies demonstrated that the mRNA of the mouse polypeptide of the invention was induced around day 5 and that the expression was linked with the generation of the cytotoxic LAK cell (data not shown).

After 7 days, the non-adherent cell population was washed away and the adherent LAK cells were removed from the plates by a short incubation with 0.01% EDTA in PBS, washed and resuspended in RPMI1640 at a cell concentration of $10^6$ cells/ml. The LAK mobility assay was performed using a 24 well size Transwell cell culture chamber (Costar Europe, Badhoevedorp, The Netherlands) essentially as described by the supplier. In the cluster well, 600 μl of RPMI1640 alone (negative control) or enriched with 50, 25, 12.5, 6.25, or 3.12 ng of the mouse polypeptide of the invention was added. In the Transwell, 100 μl of the LAK cell suspension (=$10^5$ cells) either generated with IL2 alone (LAK) or with IL2 and 50 ng/ml of the mouse polypeptide of the invention (LAK+30 kDa) was added. After 4 h incubation at 37° C., those cells which migrated through the membrane to the cluster well, were counted. The results of such an experiment are given in Table IV and clearly demonstrate that the LAK cells generated in the presence of the mouse polypeptide of the invention in the cluster well also enhances the mobility of the LAK cells.

TABLE IV

| | LAK + IL2 | | LAK + IL2 + 30KDa | |
|---|---|---|---|---|
| concentration[a] | 30kDa | — | 30kDa | — |
| 50 ng/ml | 86 | 66 | 143 | 104 |
| 25 ng/ml | 105 | 96 | 167 | 139 |
| 12.5 ng/ml | 111 | 58 | 162 | 183 |
| 6.25 ng/ml | 118 | 48 | 187 | 138 |
| 3.12 ng/ml | 79 | 79 | 201 | 136 |
| 0 ng/ml | | 58 | | 137 |

[a]concentration of the mouse polypeptide of the invention (30 kDa) in the cluster well during the mobility assay.

12.8. Intrafootpath (I. fp.) injection of the mouse polypeptide of the invention enhances the immunoresponsiveness of lymph node cells in mice.

To test the in vivo effect of the mouse polypeptide of the invention, F1 (Balb/c ×C57b1) mice were injected intrafootpath (i.fp.) with 50 ng of the mouse polypeptide of the invention in 50 μl of RPMI1640, or the equivalent volume of PBS in 50 μl RPMI1640/mouse. Twenty four hours later, the popliteal lymph node cells were isolated and resuspended in RPMI1640–50 μM β-mercaptoethanol–1% normal mouse serum (NMS) at a cell concentration of $2.10^6$ cells/mnl.

Subsequently, the cells were plated in a 96-well microtiter plate at $4.10^5$ cells/200 μl/well in the same medium and stimulated for 24–48 h with 3 μg/ml ConA (T-Cell stimulation), or 10 μg/LPS (B-Cell stimulation). $^3$H-Thymidine was added (1 μCi/well) for another 18 h and the cells were harvested and counted. The results are expressed in counts per minute (cpm) incorporated and are given in Table V.

TABLE V

ConA LPS stimulated LNC proliferation is enhanced after the in vivo ifp injection of the mouse polypeptide of the invention.

| | LNC proliferation ($cpm \times 10^{-3}$) | |
|---|---|---|
| | ConA | LPS |
| experiment 1 | | |
| -PBS treated | 63 | 2 |
| -rec prot treated | 141 | 5 |

TABLE V-continued

ConA LPS stimulated LNC proliferation is enhanced after the in vivo ifp injection of the mouse polypeptide of the invention.

| | LNC proliferation (cpm × $10^{-3}$) | |
|---|---|---|
| | ConA | LPS |
| experiment 2 | | |
| -PBS treated | 9 | N.D. |
| -rec prot treated | 153 | N.D. |

The results clearly demonstrate that the LNC from mice treated with the mouse polypeptide of the invention are sensitized to respond more efficiently towards T- and B-cell mitogens. The mouse polypeptide of the invention might therefore function directly as a costimulatory factor for T- and B-cells or more indirectly induce a T- and B-cell stimulatory factor.

12.9 Intraperitoneal injection of the mouse polypeptide of the invention augments the generation of suppressive macrophages.

To test the effect of the mouse polypeptide of the invention on peritoneal macrophages, F1 mice (Balb/c×C57b1) were injected intraperitoneal (i.p.) with either 50 ng of the mouse plypeptide of the invention in 200 μl RPMI1640 or the equivalent volume of PBS in RPMI1640. Twenty four hours later, the peritoneal exudate cells (PEC) were isolated by an i.p. wash with 10 ml of RPMI1640 per mouse, collected by centrifugation and resuspended at a concentration of $2.10^6$ cells/ml in RPMI1640–50 μM β-mercaptoethanol–1% NMS. PEC batches contaminated with erythrocytes were discarded.

$10^4$, $2.10^4$, or $3.10^4$ PEC were cocultured for 24 hours with normal lymph node cells from normal F1 mice that were seeded in 96 microtiter plates at a cell concentration of $4.10^9$ cells/200 μl/well in RPMI1640–1% NMS–3 μg/ml ConA in the absence (experiment 1) or in the presence of 10 μg/ml Indomethacin. After an additional 18 h pulse with $^3$H-thymidine (1 μCi/well), the cells were harvested and counted.

The results summarised in table VI are expressed as % suppression relative to the proliferation of LNC without PEC.

TABLE VI

The ConA induced proliferation of LNC is reduced by coculture with PEC isolated from mice injected interperitoneal with the mouse polypeptide of the invention.

| | % suppression of LNC ConA proliferation | | |
|---|---|---|---|
| | 2.5% PEC | 5% PEC | 7.5% PEC |
| experiment 1 | | | |
| -PBS treated | 0 | 38 | 97 |
| -rec prot treated | 60 | 99 | 99 |
| experiment 2 (+ indomethacin) | | | |
| -PBS treated | 0 | 0 | 0 |
| -rec prot treated | 0 | 0 | 84 |

From these results the following conclusions can be drawn:

(i) PECs from PBS and the mouse recombinant protein of the invention treated animals are suppressive on LNC. The suppressive activity of the PECs of the animals treated with the mouse polypeptide in the invention is, however, more pronounced when compared with the control animals.

(ii) The suppressive activity of PECs may be mediated via Prostaglandin (PG) release of macrophages presence in the cell mixture. To test this possibility, the PECs were cocultured with ConA stimulated LNC in the presence of PG synthesis inhibitor Indomethacin (experiment 3). From these results it is clear that the PECs from the control animals as well as from the animals treated with the mouse polypeptide of the invention mediate their suppressive activity via PG release. However, the mouse polypeptide of the invention specifically modulates PECs that mediate a part of their suppressive activity via a PG-independent mechanism.

We claim:

1. An isolated and purified nucleic acid selected from the group consisting of:

a) a nucleotide sequence consisting of SEQ ID No: 1 and SEQ ID No: 2 and SEQ ID No: 3 and SEQ ID No: 5 which codes for polypeptides having at least one of the following properties;

promoting the incorporation of $^3$H-thymidine in thymocytes, splenic cells or lymph node cells, promoting the activation or cytotoxicity or mobility of lymphocytes activated killer cells, promoting the recruitment and/or suppressive activity of suppressive peritoneal exudate cells, promoting the generation of immunocompetent lymph node cells, b) a nucleotide sequence coding for the polypeptides containing the 311 amino acids of SEQ ID No: 7 or SEQ ID No: 9 and which codes for polypeptides having at least one of the said properties, c) the above-indicated nucleotide seqences wherein T is replaced by U.

2. A vector selected from the group consisting of a plasmid, cosmid, and virus comprising vector DNA and a recombinant nucleic acid of claim 1.

3. A unicellular host containing a vector of claim 2.

4. A unicellular host of claim 3, wherein said cellular host is chosen from the group consisting of *Escherichia coli*, COS cells, Sf9 cells, RK13 cells and Hela cells.

5. A nucleotide acid of claim 1 wherein the nucleotide sequence codes for polypeptides having the amino acid sequences of pep1 (m) (SEQ ID No: 11 and SEQ ID No: 12) or pep1 (h) (SEQ ID No: 17 and SEQ ID No: 18), or pep2 (m) SEQ ID No: 13 and SEQ ID No: 14) or pep2 (h) (SEQ ID No: 19 and SEQ ID No: 20), or pep3 (m) (SEQ ID No: 15 and SEQ ID No: 16 or pep3 (h) (SEQ ID No: 21 and SEQ ID No: 22).

* * * * *